US011590202B2

(12) United States Patent
Bromberg et al.

(10) Patent No.: US 11,590,202 B2
(45) Date of Patent: Feb. 28, 2023

(54) INHIBITORS OF LTβR-NFκB SIGNALING PATHWAYS FOR TREATING INFLAMMATION AND CANCER

(71) Applicant: University of Maryland, Baltimore, Baltimore, MD (US)

(72) Inventors: Jonathan Bromberg, Baltimore, MD (US); Wenji Piao, Catonsville, MD (US); Yanbao Xiong, Timonium, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/604,674

(22) PCT Filed: Apr. 11, 2018

(86) PCT No.: PCT/US2018/027049
§ 371 (c)(1),
(2) Date: Oct. 11, 2019

(87) PCT Pub. No.: WO2018/191348
PCT Pub. Date: Oct. 18, 2018

(65) Prior Publication Data
US 2020/0085912 A1    Mar. 19, 2020

Related U.S. Application Data

(60) Provisional application No. 62/484,029, filed on Apr. 11, 2017.

(51) Int. Cl.
*C07K 14/715* (2006.01)
*C07K 19/00* (2006.01)
*A61K 38/17* (2006.01)
*C07K 14/435* (2006.01)
(Continued)

(52) U.S. Cl.
CPC ...... *A61K 38/1793* (2013.01); *A61K 38/1767* (2013.01); *C07K 14/43581* (2013.01); *C07K 14/7151* (2013.01); *A61P 29/00* (2018.01); *A61P 35/00* (2018.01)

(58) Field of Classification Search
None
See application file for complete search history.

(56) References Cited

U.S. PATENT DOCUMENTS

2002/0127615 A1    9/2002    Lederman
2003/0004112 A1    1/2003    Potter
2005/0272633 A1    12/2005   Wallach
(Continued)

OTHER PUBLICATIONS

Chiang et al., Targeted depletion of lymphotoxin-a-expressing TH1 and TH17 cells inhibits autoimmune disease, Nat. Med. 15(7): 766-773, 2009.*
(Continued)

*Primary Examiner* — Claire Kaufman
(74) *Attorney, Agent, or Firm* — Riverside Law LLP

(57) ABSTRACT

The present invention provides compositions and methods for selective inhibition of the classical or non-classical LTβR-NFκB signaling pathway. In some embodiments, the compositions and methods of the present invention are useful for treating or preventing tissue graft rejection, inflammation, contact hypersensitivity, and cancer by decreasing cell motility.

3 Claims, 43 Drawing Sheets

Specification includes a Sequence Listing.

(51) Int. Cl.
*A61P 29/00* (2006.01)
*A61P 35/00* (2006.01)

(56) References Cited

U.S. PATENT DOCUMENTS

2006/0099275 A1 5/2006 Lin
2012/0282245 A1 11/2012 Lukashev

OTHER PUBLICATIONS

Piao et al., LTβR signaling controls lymphatic migration of immune cells, Cells, 10(4), 747, 10.3390/cells10040747, 17pages, 2021.*
Matusumoto et al., Hepatits C virus core protein interacts with the cytoplasmic tail of lymphotoxin-beta receptor, J. Virol. 71(2):1301-1309, 1997.*
Betts et al., Suppression of tumour-specific CD4+ T cells by regulatory T cells is associated with progression of human colorectal cance, Gut, 61:1163-1171, 2012.*
Heitz et al., Twenty years of cell-penetrating peptides: from molecular mechanism to therapetuics, Br. J. Pharmacol. 157:195-206, 2009:187-202, 2012.*
Sun, S., The non-canonical NF-kB pathway in immunity and inflammation, Nat. Rev. Immunol. 17:545-558, Sep. 2017.*
Dom et al., Cellular uptake of Antennapedia Penetratin peptides in a two-step process in which phase transfer precedes a tryptopha-dependent translocation, Nucl. Acids Res. 31(2): 2003.*
Alitalo, Annamari, and Michael Detmar. "Interaction of tumor cells and lymphatic vessels in cancer progression." Oncogene 31.42 (2012): 4499-4508.
Basak, Soumen, et al. "Afourth IkB protein within the NF-kB signaling module." Cell 128.2 (2007): 369-381.
Beinke, Sören, and Steven C. Ley. "Functions of NF-kB1 and NF-kB2 in immune cell biology." Biochemical Journal 382.2 (2004): 393-409.
Berlin, Cornelia, et al. "α4β7 integrin mediates lymphocyte binding to the mucosal vascular addressin MAdCAM-1 ."Cell 74.1 (1993): 185-195.
Bista, Pradeep, et al. "TRAF3 controls activation of the canonical and alternative NFkB by the lymphotoxin beta receptor." Journal of Biological Chemistry 285.17 (2010): 12971-12978.
Brinkman, C. Colin, et al. "Treg engage lymphotoxin beta receptor for afferent lymphatic transendothelial migration." Nature communications 7.1 (2016): 1-16.
Bromley, Shannon K., Seddon Y. Thomas, and Andrew D. Luster. "Chemokine receptor CCR7 guides T cell exit from peripheral tissues and entry into afferent lymphatics." Nature immunology 6.9 (2005): 895-901.
Butcher, Eugene C., and Louis J. Picker. "Lymphocyte homing and homeostasis." Science 272.5258 (1996): 60-67.
De Togni, Pietro, et al. "Abnormal development of peripheral lymphoid organs in mice deficient in lymphotoxin." Science 264. 5159 (1994): 703-707.
Dejardin, Emmanuel, et al. "The lymphotoxin-β receptor induces different patterns of gene expression via two NF-kB pathways." Immunity 17.4 (2002): 525-535.
DeNucci, Christopher C., et al. "Control ofα4β7 integrin expression and CD4 T cell homing by the β1 integrin subunit." The Journal of Immunology 184.5 (2010): 2458-2467.
Engeman, Tara M., et al. "Inhibition of functional T cell priming and contact hypersensitivity responses by treatment with anti-secondary lymphoid chemokine antibody during hapten sensitization." The Journal of Immunology 164.10 (2000): 5207-5214.
Fava, Roy A., et al. "A role for the lymphotoxin/LIGHT axis in the pathogenesis of murine collagen-induced arthritis." The Journal of Immunology 171.1 (2003): 115-126.
Fontenot, Jason D., et al. "Regulatory T cell lineage specification by the forkhead transcription factor foxp3." Immunity 22.3 (2005): 329-341.

Force, Walker R., et al. "Discrete signaling regions in the lymphotoxin-β receptor for tumor necrosis factor receptor-associated factor binding, subcellular localization, and activation of cell death and NF-κB pathways." Journal of Biological Chemistry 275.15 (2000): 11121-11129.
Fukunaga, Atsushi, et al. "Dermal dendritic cells, and not Langerhans cells, play an essential role in inducing an immune response." The Journal of immunology 180.5 (2008): 3057-3064.
Ganeff, Corinne, et al. "Induction of the alternative NF-κB pathway by lymphotoxin αβ (LTαβ) relies on internalization of LTβ receptor." Molecular and cellular biology 31.21 (2011): 4319-4334.
Hostager, Bruce S., and Gail A. Bishop. "Cutting edge: contrasting roles of TNF receptor-associated factor 2 (TRAF2) and TRAF3 in CD40-activated B lymphocyte differentiation." The Journal of Immunology 162.11 (1999): 6307-6311.
Ishimoto, Takuji, et al. "Downregulation of monocyte chemoattractant protein-1 involving short interfering RNA attenuates hapten-induced contact hypersensitivity." Molecular Therapy 16.2 (2008): 387-395.
Johnson, Louise A., et al. "An inflammation-induced mechanism for leukocyte transmigration across lymphatic vessel endothelium." Journal of experimental medicine 203.12 (2006): 2763-2777.
Mackay, Fabienne, et al. "Both the lymphotoxin and tumor necrosis factor pathways are involved in experimental murine models of colitis." Gastroenterology 115.6 (1998): 1464-1475.
Madge, Lisa A., et al. "Lymphotoxin-α1β2 and LIGHT induce classical and noncanonical NF-κB-dependent proinflammatory gene expression in vascular endothelial cells." The Journal of Immunology 180.5 (2008): 3467-3477.
Moussion, Christine, and Jean-Philippe Girard. "Dendritic cells control lymphocyte entry to lymph nodes through high endothelial venules." Nature 479.7374 (2011): 542-546.
Nakayama, Yumi, and Jonathan S. Bromberg. "Lymphotoxin beta receptor blockade induces inflammation and fibrosis in tolerized cardiac allografts." American journal of transplantation 12.9 (2012): 2322-2334.
Niessen, Carien M., et al. "Deficiency of the integrin beta 4 subunit in junctional epidermolysis bullosa with pyloric atresia: consequences for hemidesmosome formation and adhesion properties." Journal of Cell Science 109.7 (1996): 1695-1706.
Ortega Gómez, Almudena, Mauro Perretti, and Oliver Soehnlein. "Resolution of inflammation: an integrated view." EMBO molecular medicine 5.5 (2013): 661-674.
Pace, C. Nick, et al. "How to measure and predict the molar absorption coefficient of a protein." Protein science 4.11 (1995): 2411-2423.
Piao, Wenji, et al. "A decoy peptide that disrupts TIRAP recruitment to TLRs is protective in a murine model of influenza." Cell reports 11.12 (2015): 1941-1952.
Piao, Wenji, et al. "Recruitment of TLR adapter TRIF to TLR4 signaling complex is mediated by the second helical region of TRIF TIR domain." Proceedings of the National Academy of Sciences 110.47 (2013): 19036-19041.
Piguet, Pierre F., et al. "Tumor necrosis factor is a critical mediator in hapten induced irritant and contact hypersensitivity reactions." The Journal of experimental medicine 173.3 (1991): 673-679.
Rennert, Paul D., et al. "Surface lymphotoxin alpha/beta complex is required for the development of peripheral lymphoid organs." The Journal of experimental medicine 184.5 (1996): 1999-2006.
Russo, Erica, et al. "Intralymphatic CCL21 promotes tissue egress of dendritic cells through afferent lymphatic vessels." Cell reports 14.7 (2016): 1723-1734.
Schneider, Kirsten, Karen G. Potter, and Carl F. Ware. "Lymphotoxin and LIGHT signaling pathways and target genes." Immunological reviews 202.1 (2004): 49-66.
Sonnenberg, A., et al. "The alpha 6 beta 1 (VLA-6) and alpha 6 beta 4 protein complexes: tissue distribution and biochemical properties." Journal of Cell Science 96.2 (1990): 207-217.
Vigl, Benjamin, et al. "Tissue inflammation modulates gene expression of lymphatic endothelial cells and dendritic cell migration in a stimulus-dependent manner." Blood, The Journal of the American Society of Hematology 118.1 (2011): 205-215.

(56) References Cited

OTHER PUBLICATIONS

Xiong, Yanbao, et al. "T-bet regulates natural regulatory T cell afferent lymphatic migration and suppressive function." The Journal of Immunology 196.6 (2016): 2526-2540.

Xu, Liang-Guo, and Hong-Bing Shu. "TNFR-associated factor-3 is associated with BAFF-R and negatively regulates BAFF-R-mediated NF-κB activation and IL-10 production." The Journal of Immunology 169.12 (2002): 6883-6889.

Ye, Hong, et al. "The structural basis for the recognition of diverse receptor sequences by TRAF2." Molecular cell 4.3 (1999): 321-330.

Zhang, Nan, et al. "Regulatory T cells sequentially migrate from inflamed tissues to draining lymph nodes to suppress the alloimmune response." Immunity 30.3 (2009): 458-469.

Extended European Search Report for App. No. EP18785010.2, dated Mar. 3, 2021, 8 pages.

Liu H P et al: "The MYND domain-containing protein BRAM1 inhibits lymphotoxin beta receptor-mediated signaling through affecting receptor oligomerization", Cellular Signalling, Elsevier Science Ltd, GB, vol. 23, No. 1, Jan. 1, 2011 (Jan. 1, 2011), pp. 80-88, XP027415676, ISSN: 0898-6568 [retrieved on Aug. 21, 2010].

Mae M et al: "Internalisation of cell-penetrating peptides into tobacco protoplasts", BBA-Biomembranes, Elsevier, Amsterdam, NL, vol. 1669, No. 2, May 20, 2005 (May 20, 2005), pp. 101-107, XP027733892, ISSN: 0005-2736 [retrieved on May 20, 2005].

Mortier J et al: "NF-@κ13 inducing kinase (NIK) inhibitors: Identification of new scaffolds using virtual screening", BIORGANIC & Medicinal Chemistry Letters, Elsevier, Amsterdam, NL, vol. 20, No. 15, Aug. 1, 2010 (Aug. 1, 2010), pp. 4515-4520, XP027263611, ISSN: 0960-894X [retrieved on Jun. 8, 2010].

Browning Jeffrey L: "Inhibition of the lymphotoxin pathway as a therapy for autoimmune disease", Immunological Reviews, Wiley-Blackwell Publishing, Inc, US, vol. 223, No. 1, Jun. 1, 2008 (Jun. 1, 2008), pp. 202-220, XP002554450, ISSN: 0105-2896, Doi: 10.1111/J.1600-065X.2008.00633.X [retrieved on Jul. 8, 2008].

* cited by examiner

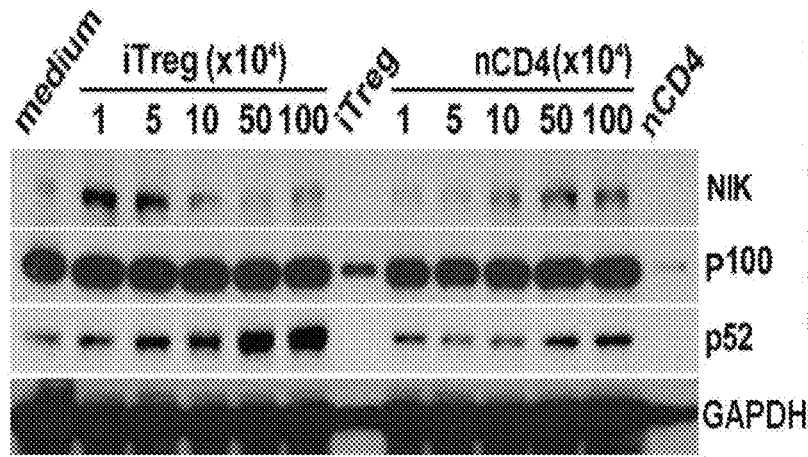
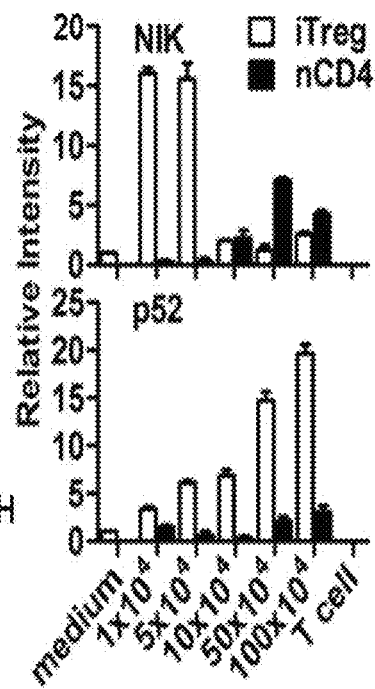
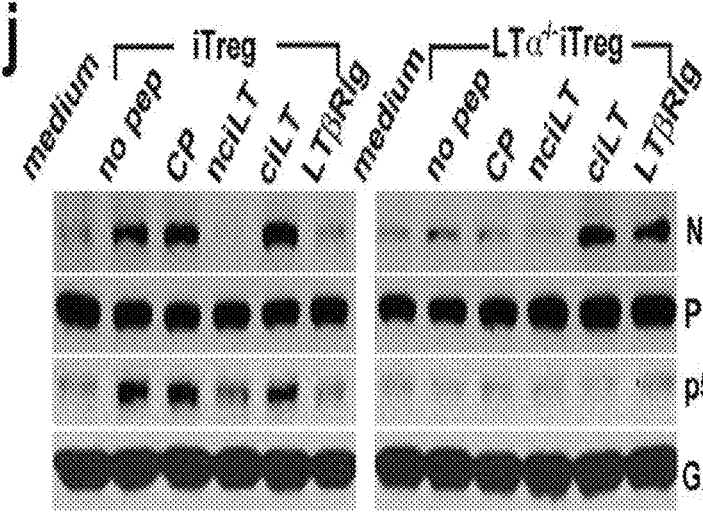
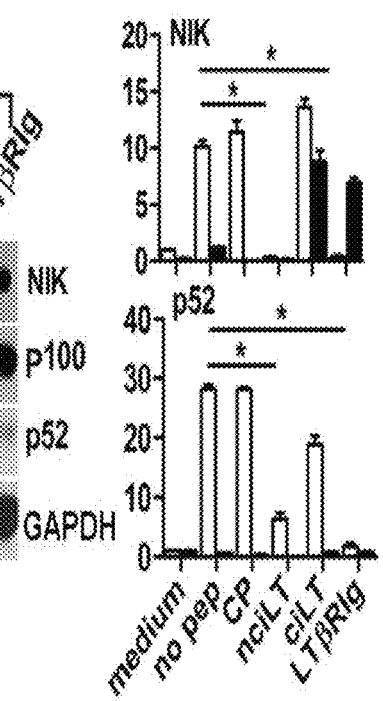
Figure 6I- Figure 6J

LEC activated with anti-LTβR/CL + nciLT vs no activation or blocking peptide treatment

Canonical Pathways

| Name | p value (Fisher test) | number of genes (% of overlap) |
|---|---|---|
| Colorectal Cancer Metastasis Signaling | 4.28E-07 | 19 (7.9) |
| Role of Macrophages, Fibroblasts and Endothelial Cells in Rheumatoid Arthritis | 7.09E-07 | 21 (7.0) |
| HMGB1 Signaling | 2.23E-06 | 13 (9.9) |
| Activation of IRF by Cytosolic Pattern Recognition Receptors | 2.73E-06 | 9 (15) |
| Role of Osteoblasts, Osteoclasts and Chondrocytes in Rheumatoid Arthritis | 3.31E-06 | 17 (7.5) |

Upstream Regulator

| Regulator | p value of overlap | number of targets | z score | Predicted activation |
|---|---|---|---|---|
| TNF | 1.32E-30 | 104 | 5.58 | activated |
| IL1B | 2.05E-26 | 69 | 5.64 | activated |
| TGFB1 | 6.34E-26 | 97 | 3.97 | activated |
| PDGF BB | 2.16E-25 | 43 | 4.09 | activated |
| IFNG | 2.07E-24 | 81 | 5.65 | activated |

Figure 10

LEC activated with anti-LTβR/CL + nciLT vs anti-LTβR/CL + control peptide treatment

Canonical Pathways

| Name | p value (Fisher test) | number of genes (% of overlap) |
|---|---|---|
| Colorectal Cancer Metastasis Signaling | 1.63E-06 | 16 (6.6) |
| HMGB1 Signaling | 4.98E-06 | 11 (8.7) |
| Role of Macrophages, Fibroblasts and Endothelial Cells in Rheumatoid Arthritis | 5.66E-06 | 17 (5.7) |
| Production of Nitric Oxide and Reactive Oxygen Species in Macrophages | 6.48E-06 | 13 (7.1) |
| ILK Signaling | 8.7E-06 | 13 (7.0) |

Upstream Regulator

| Regulator | p value of overlap | number of targets | z score | Predicted activation |
|---|---|---|---|---|
| TNF | 3.42E-34 | 95 | 4.36 | activated |
| PDGF BB | 3.68E-28 | 42 | 3.96 | activated |
| IL1B | 5.66E-27 | 62 | 3.78 | activated |
| TGFB1 | 3.19E-22 | 79 | 5.32 | activated |
| EGF | 1.43E-20 | 42 | 4.45 | activated |

Figure 11

LEC activated with anti-LTβR/CL + nciLT vs anti-LTβR/CL + ciLT treatment

| Upstream Regulator | | | |
|---|---|---|---|
| Regulator | p value of overlap | number of targets | z score | Predicted activation |
| TNF | 6.16E-17 | 39 | 3.48 | activated |
| IL1B | 1.9E-16 | 29 | 3.75 | activated |
| PDGF BB | 5.25E-14 | 18 | 2.63 | activated |
| EGRF | 2.22E-13 | 17 | 3.37 | activated |

Figure 12

SEQUENCE LISTING

```
<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Chemically Synthesized
```

```
<400> SEQUENCE: 2

Thr Gly Asn Ile Tyr Ile Tyr Asn Gly Pro Val Leu
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 3

Pro Glu Glu Gly Ala Pro Gly Pro
1               5

<210> SEQ ID NO 4
<211> LENGTH: 28
<212> TYPE: PRT
<213> ORGANISM: Artificial Sequence
<220> FEATURE:
<223> OTHER INFORMATION: Chemically Synthesized

<400> SEQUENCE: 4

Arg Gln Ile Lys Ile Trp Phe Gln Asn Arg Arg Met Lys Trp Lys Lys
1               5                   10                  15

Thr Gly Asn Ile Tyr Ile Tyr Asn Gly Pro Val Leu
            20                  25

<210> SEQ ID NO 5
<211> LENGTH: 24
<212> TYPE: PRT
<213> ORGANISM: Artificial Sequence
<220> FEATURE:
<223> OTHER INFORMATION: Chemically Synthesized

<400> SEQUENCE: 5

Arg Gln Ile Lys Ile Trp Phe Gln Asn Arg Arg Met Lys Trp Lys Lys
1               5                   10                  15

Pro Glu Glu Gly Ala Pro Gly Pro
            20

<210> SEQ ID NO 6
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 6

Cys Met His Ile Glu Ser Leu Asp Ser Tyr Thr Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 7

Cys Met Tyr Ile Glu Ala Leu Asp Lys Tyr Ala Cys
1               5                   10

<210> SEQ ID NO 8
```

```
<211> LENGTH: 29
<212> TYPE: PRT
<213> ORGANISM: Artificial Sequence
<220> FEATURE:
<223> OTHER INFORMATION: Chemically Synthesized

<400> SEQUENCE: 8

Glu Ala Ala Leu Ala Glu Ala Leu Ala Glu Ala Leu Ala Glu Ala Leu
1               5                   10                  15

Ala Glu Ala Leu Ala Glu Ala Leu Glu Ala Leu Ala Ala
            20                  25

<210> SEQ ID NO 9
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 9

Gly Asn Ala Ala Ala Ala Arg Arg
1               5

<210> SEQ ID NO 10
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 10

Cys Asp Pro Gly Tyr Ile Gly Ser Arg Cys
1               5                   10
```

INHIBITORS OF LTβR-NFκB SIGNALING PATHWAYS FOR TREATING INFLAMMATION AND CANCER

CROSS REFERENCE TO RELATED APPLICATIONS

This application is a U.S. national phase application filed under 35 U.S.C. § 371 claiming benefit to International Patent Application No. PCT/US2018/027049, filed Apr. 11, 2018, which is entitled to priority under 35 U.S.C. § 119(e) to U.S. Provisional Application No. 62/484,029, filed Apr. 11, 2017, each of which is hereby incorporated by reference herein in its entirety.

STATEMENT REGARDING FEDERALLY SPONSORED RESEARCH OR DEVELOPMENT

This invention was made with government support under Grant Number A1062765 awarded by the National Institute of Health. The government has certain rights in the invention.

SEQUENCE LISTING

The contents of the text file named "206187_0005_00US_Sequence_listing_ST25.TXT", which was created on Oct. 11, 2019, and is 2,911 bytes in size, is hereby incorporated by reference in its entirety.

BACKGROUND OF THE INVENTION

Recirculating CD4 T cells enter lymph nodes (LNs) from tissues via afferent lymphatics or from blood to LNs across high endothelial venules (HEV). Migration is dependent on cell adhesion molecules (CAMs) such as integrins, mucins, and selectins on T cells and endothelial cells. CAMs are either expressed constitutively or induced by cytokines during inflammation. Integrins bind to immunoglobulin (Ig) superfamily CAMs, such as VCAM-1, ICAMs, and MadCAM-1. Transendothelial migration (TEM) of the leukocytes from blood to LNs or non-lymphoid tissues generally requires initial coupling of integrins-CAMs, leading the migrating cells to dock and crawl on vascular endothelium, and subsequently to be activated by the CCR7/CCL21-mediated chemotaxis to promote TEM (Butcher, E. C. et al., 1996, Science, 272:60-66). However, the regulation of T cell migration from tissues to LNs via afferent lymphatics is far less well defined. Recent studies suggest that afferent lymphatic T cell migration is distinct from dendritic cell, neutrophil, or monocyte migration, and is governed by integrin-independent mechanisms, such as S1P/S1PR1-mediated homeostatic T cell trafficking (Bromley, S. K. et al., 2005, Nat Immunol, 6:895-901) and LTα1β2/LTβR-mediated regulatory T cells (Treg) entry into lymph (Brinkman, C. C. et al., 2016, Nat Commun, 7:12021).

The migration of Treg from grafts to LN via afferent lymphatics is critical for graft survival, and cannot be supplanted by Treg migration from blood through HEV into the same LN (Zhang, N. et al., 2009, Immunity, 30:458-469). Treg specifically employ several molecular mechanisms, distinct from non-Treg CD4+T cells, to migrate through afferent lymphatics (Brinkman, C. C. et al., 2016, Nat Commun, 7:12021; Xiong, Y. et al., 2016, J Immunol, 196:2526-2540). A unique mechanism employed by Treg is the high-level expression of cell surface lymphotoxin (LT), which is required for migration from the allograft to afferent lymphatics and then to the draining LN (Brinkman, C. C. et al., 2016. Nat Commun, 7:12021). This LT-dependent mechanism is not required to enter LN via the HEV, nor for egress from the LN to efferent lymphatics. Treg cell surface LT binds to and activates the LTβ receptor (LTβR) expressed on lymphatic endothelial cells (LEC), causing changes in LEC morphology that accompany Treg migration.

LT is a member of the tumor necrosis factor (TNF) superfamily that has a major role in lymphoid organogenesis (Rennert, P. D. et al., 1996, J Exp Med, 184:1999-2006; De Togni, P., et al. 1994, Science, 264:703-707). LT has two subunits (LTα and LTβ) and is found in two distinct forms: soluble homotrimer of LTα (LTα3) that binds TNF receptors, and membrane-bound heterotrimer (LTα1β) that signals via LTβ receptor (LTβR) (FIG. 1E). Unlike TNF receptors (TNFR) that activate exclusively the classical arm of NFκB, activated LTβR induces both classical (NFκB1) and non-classical (NFκB2) NFκB pathways (Beinke, S. et al., 2004, Biochem J, 382:393-409). NFκB1 activation is rapid and transient, involves the Inhibitor of kappa-B kinase (IKK)-complex mediated phosphorylation and degradation of the inhibitor IκBa, to allow p50-mediated gene transcription. In contrast, activation of NFκB2 is gradual and involves NFκB inducing kinase (NIK)-dependent processing of NFκB2/p100 into its transcription-regulatory fragment p52. Classical IKKβ-NFκB-dependent genes include inflammatory chemokines (CCL4 and CCL2) and adhesion molecules (VCAM-1, ICAM-1, and ELAM-1). In contrast, alternative IKKα-NF-κB-dependent genes include homeostatic chemokines involved in lymphoid organogenesis (CCL21, CCL19, and CXCL12) (Dejardin, E. et al., 2002, Immunity, 17:525-535; Madge, L. A. et al., 2008, J Immunol, 180:3467-3477). The Treg LTαβ-LEC LTβR interaction favors the non-classical over the classical signaling pathway (Brinkman, C. C. et al., 2016, Nat Commun, 7:12021; Basak, S. et al. 2007, Cell, 128:369-381). However, the precise nature of LTβR signaling in LEC and the consequences for LEC structure and function that regulate Treg migration remain to be fully defined and quantitated.

In resting cells, TNFR-associated factor (TRAF) 2-cellular inhibitors of apoptosis (cIAP) 1/2 and TRAF3-NIK form a persistent homeostatic complex. Newly synthesized NIK is rapidly bound by TRAF3 and targeted to TRAF-cIAP degradation to maintain an extremely low level of NIK, thereby preventing induction of p100 processing. For LTβR-mediated p100 processing, TRAF2 bridges cIAP1/2, an E3 ubiquitin ligase, to degrade TRAF3. TRAF2 and TRAF3 thus function as mediators and inhibitors of LTβR signaling, respectively (Hostager, B. S. et al., 1999, J Immunol, 162: 6307-6311; Xu, L. G. et al., 2002, J Immunol, 169:6883-6889; Bista, P. et al., 2010, J Biol Chem, 285:12971-12978), and TRAF3 deficient cells exhibit constitutive NFκB2 activation. In the absence of TRAF3, de novo synthesized NIK is accumulated and activated via trans-phosphorylation. NIK then activates IKKα, leading to p100 processing and nuclear translocation of RelB/p52.

LTβRIg, a soluble decoy fusion protein comprised of the ectodomain of LTβR fused to Fc of immunoglobulin G, blocks LT/LIGHT binding to LTβR and has shown efficacy in preclinical disease models as an anti-inflammatory treatment (Mackay, F. et al., 1998, Gastroenterology, 115:1464-1475). However, these results have not been consistent across disease models (Fava, R. A. et al., 2003, J Immunol, 171:115-126; Chiang, E. Y. et al. 2009, Nat Med, 15:766-773). As LTβRIg blocks signaling induced by both LTα1β2 and LIGHT, thus blocks both the classical and alternative NFκB pathways, it is difficult to determine which ligands and signaling pathways are important in the aforementioned models. Furthermore, it was demonstrated that treatment with LTβRIg failed to improve cardiac allograft survival (Nakayama, Y. et al., 2012, Am J Transplant, 12:2322-2334), yet LT expression by Treg was required to prolong islet allograft survival (Brinkman, C. et al., 2016, Nature Commun., 7:12021). Thus, specific targeting of either arm of LTβR signaling may reveal the pathway that is responsible for promoting Treg trafficking, and perhaps enable selective control of Treg migration.

Therefore, there is a need in the art for selective targeting of particular components of the LTβR signaling pathway for the treatment of diseases characterized by altered cell migration, including but not limited to inflammation, graft rejection, contact hypersensitivity, and cancer. The present invention addresses this unmet need.

SUMMARY OF THE INVENTION

In one aspect, the invention provides a composition for inhibiting cell motility, comprising an inhibitor of the non-classical LTβR-NFκB signaling pathway. In one embodiment, the inhibitor comprises at least one selected from the group consisting of a polynucleotide, a polypeptide, a ribozyme, an antibody, an antisense nucleic acid, a small molecule, and a combination thereof. In one embodiment, the inhibitor comprises a polypeptide comprising a cell-penetrating peptide (CPP). In one embodiment, the inhibitor comprises a polypeptide comprising a fragment of an intracellular domain of LTβR. In one embodiment, the CPP comprises the peptide sequence of the Drosophila antennapedia comprising the amino acid sequence of SEQ ID NO:1. In one embodiment, the fragment of an intracellular domain of LTβR comprises the amino acid sequence of SEQ ID NO:2. In one embodiment, the polypeptide comprises the amino acid sequence of SEQ ID NO:4.

In one aspect, the invention provides a composition comprising an inhibitor of the classical LTβR-NFκB signaling pathway. In one embodiment, the inhibitor comprises at least one selected from the group consisting of a polynucleotide, a polypeptide, a ribozyme, an antibody, an antisense nucleic acid, a small molecule, and a combination thereof. In one embodiment, the inhibitor comprises a polypeptide comprising a cell-penetrating peptide (CPP). In one embodiment, the inhibitor comprises a polypeptide comprising a fragment of an intracellular domain of LTβR. In one embodiment, the CPP comprises the peptide sequence of the Drosophila antennapedia comprising the amino acid sequence of SEQ ID NO:1. In one embodiment, the fragment of an intracellular domain of LTβR comprises the amino acid sequence of SEQ ID NO:3. In one embodiment, the polypeptide comprises the amino acid sequence of SEQ ID NO:5.

In one aspect, the invention provides a method for inhibiting cell motility, comprising administering to a subject an inhibitor of the non-classical LTβR-NFκB signaling pathway. In one embodiment, the inhibitor comprises at least one selected from the group consisting of a polynucleotide, a polypeptide, a ribozyme, an antibody, an antisense nucleic acid, a small molecule, and a combination thereof. In one embodiment, the inhibitor comprises a polypeptide comprising a cell-penetrating peptide (CPP). In one embodiment, the inhibitor comprises a polypeptide comprising a fragment of an intracellular domain of LTβR. In one embodiment, the CPP comprises the peptide sequence of the Drosophila antennapedia comprising the amino acid sequence of SEQ ID NO:1. In one embodiment, the fragment of an intracellular domain of LTβR comprises the amino acid sequence of SEQ ID NO:2. In one embodiment, the polypeptide comprises the amino acid sequence of SEQ ID NO:4. In one embodiment the subject has, or is at risk of developing, at least one condition selected from the group consisting of tissue graft rejection, inflammation, contact hypersensitivity, and cancer.

In one aspect, the invention provides a method for inhibiting the classical LTβR-NFκB signaling pathway, comprising administering to a subject an inhibitor of the classical LTβR-NFκB signaling pathway. In one embodiment, the inhibitor comprises at least one selected from the group consisting of a polynucleotide, a polypeptide, a ribozyme, an antibody, an antisense nucleic acid, a small molecule, and a combination thereof. In one embodiment, the inhibitor comprises a polypeptide comprising a cell-penetrating peptide (CPP). In one embodiment, the inhibitor comprises a polypeptide comprising a fragment of an intracellular domain of LTβR. In one embodiment, the CPP comprises the peptide sequence of the Drosophila antennapedia comprising the amino acid sequence of SEQ ID NO:1. In one embodiment, the fragment of an intracellular domain of LTβR comprises the amino acid sequence of SEQ ID NO:3. In one embodiment, the polypeptide comprises the peptide represented by SEQ ID NO:5.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1, comprising FIG. 1A depicts flow cytometry analysis of LTβR expression on murine primary LEC and SVEC4-10 cells. FIG. 1B depicts whole mount ear staining and in vitro immunohistochemistry for LTβR and NIK expression on Lyve-1 expressing mouse ear LEC and primary LEC or SVEC4-10 cells. FIG. 1C and FIG. 1F depicts mouse primary LEC or SVEC4-10 stimulated with 2 μg/mL 3C8 anti-LTβR mAb, cross-linked (CL) anti-LTβR mAb, 20 ng/mL TNFα, or 25 μM AT406. For cross-linking, cells were incubated with anti-LTβR mAb at 4° C., washed, and then cross linked with 2 μg/mL mouse anti-rat IgG1 for the indicated times. Total cell lysates were immunoblotted with anti-p100/p52, NIK,phosphorylated IKKα/β, IκBα, and GAPDH expression. The bar graphs represent the relative band intensities (mean±SD) from three independent experiments. Representative of three independent experiments. FIG. 1D depicts nuclear translocation of RelA/p65 in LEC stimulated with 2 μg/ml anti-LTβR for 10 min. Magnification 60×; scale bar 4 μm. FIG. 1E depicts diagram of TNFα and LTβR-mediated classical and non-classical NFκB signaling.

FIG. 2, comprising FIG. 2A depicts qRT-PCR of the indicated genes induced by agonistic anti-LTβR mAb or isotype rat IgG with or without CL in LEC at the indicated times. Relative gene expression was normalized to HPRT. FIG. 2B depicts flow cytometry analysis of VCAM-1 expression on LEC after treatment with anti-LTβR mAb plus CL with or without NFκB inhibitor (BAY11-7085) or NIKi for 3 hours. FIG. 2C depicts secretion of CCL2 and CCL21 by anti-LTβR mAb stimulated LEC with or without BAY11-7085 or NIKi measured at the indicated times. FIG. 2D depicts LTβR-induced CXCL12 and VCAM-1 expression on SVEC4-10 treated with 2 μg/mL anti-LTβR mAb for 3 hours. FIG. 2A and FIG. 2C depict means±SEM of three independent experiments. FIG. 2B and FIG. 2D are representative of three independent experiments. *p<0.05 by one-way ANOVA.

FIG. 3, comprising FIG. 3A depicts a diagram of peptide selective blockade of separate arms of LTβR signaling. FIG. 3B depicts immunoprecipitation of LTβR complex with anti-LTβR in lysates of LEC pretreated with the indicated peptides and then stimulated with anti-LTβR mAb for 10 minutes. Complexes were run on SDS-PAGE, and immune blotted with anti-TRAF2, anti-TRAF3, and anti-LTβR, and whole cell lysates were run on SDS-PAGE, and immune blotted with anti-TRAF2, and anti-TRAF3, and anti-LTβR. FIG. 3C and FIG. 3D depict LEC and SVEC4-10 pretreated with indicated peptides or inhibitors and then stimulated with anti-LTβR for 10 minutes (FIG. 3C). Cell lysates were immune blotted for IKKα/β, and IκBα phosphorylation and degradation, with GAPDH as loading control (FIG. 3C) and immunohistochemistry of RelA (FIG. 3D). FIG. 3E, FIG. 3F and FIG. 3G depict cells pretreated with indicated peptides or inhibitors and then stimulated with anti-LTβR for 6 hours. mLEC lysates immune blotted for p100/p52, NIK, TRAF2, and TRAF3 expression (FIG. 3E). Immunohistochemistry of LTβR and NIK in SVEC4-10 (FIG. 3F); CCL21 and RelB in mLEC (FIG. 3G). For FIG. 3B, FIG. 3C, and FIG. 3E, data are representative of relative band intensities (mean±SD) from three independent experiments. *p<0.05 by one-way ANOVA.

FIG. 4, comprising FIG. 4A depicts qRT-PCR for VCAM-1, CCL2, CXCL12, CCL19, and CCL21. FIG. 4B depicts ELISA for CCL2 and CCL21 in the LEC supernatants after 4 or 16 hours stimulation, respectively. FIG. 4C depicts expression of CXCL12 and VCAM-1 in LEC after 3 hours stimulation (magnification 40×; scale bar 20 μm). FIG. 4D depicts whole mount staining of ear pinnae for CCL21 and Lyve-1. C57BL/6 mice injected with 0.1 nM/ear in 10 μL of control peptide (CP), nciLT or ciLT; after 3 hours ears fixed and stained. Magnification 20×; scale bar 50 μm. FIG. 4E depicts qRT-PCR of VCAM-1 in LEC stimulated with TNFα for 1 hour. FIG. 4F and FIG. 4G depict mount ear staining of NIK and CCL21 in Proxl-Cre-ERT2×LTβR$^{fl/fl}$ mice 10 days after tamoxifen treatment. BV, blood vessel (magnification 6×; scale bar 10 μm). FIG. 4A, FIG. 4B, and FIG. 4E show means±SEM of at least 4 independent experiments. FIG. 4C and FIG. 4D are representative of two independent experiments. *p<0.05 by one-way ANOVA.

FIG. 5, comprising FIG. 5A depicts results from pretreating LEC cells or T cells with the indicated peptides (20 μM) for 30 minutes at 37° C. and then loading Foxp3+CD4+CD25+iTregs, Foxp3-CD25-CD4+ Teff, or naïve CD4 cells into the upper chamber and allowing cell migration toward CCL19 for 3 hours. FIG. 5B depicts LEC incubated with 20 μM nciLT or ciLT peptides for 3 hours without or with stimulation with anti-LTβR mAb, measuring cell viability as determined by MTT incorporation assay. FIG. 5C depicts time-course monitoring of 0.75% albumin/Evans Blue diffusion across LEC cell layer in Boyden chamber treated as indicated. FIG. 5D depicts LEC cell layers pretreated with anti-LTβR mAb or isotype rat IgG for 30 minutes at 4° C., washed and CL for 30 minutes at 37° C., followed by a 16 hour incubation, then naïve CD4 cells were loaded into the upper chamber and migrated toward CCL19 for 3 hours. FIG. 5E and FIG. 5F depict results from the footpad-popliteal LN migration assay; naïve CD4 T cells were stained with CFSE, then mixed with 20 μM control peptide (CP) or nciLT or 1004 ciLT peptide without (FIG. 5E) or with anti-LTβR mAb (FIG. 5F), were pair injected into the footpads of each mouse. 16 hours post injection, popliteal LN was collected and analyzed with flow cytometry. FIG. 5G depicts whole mount staining and migration of ear; CFSE-naïve CD4 T cells were injected into ear pinnae pretreated with peptides, and collected after 16 hours post injection. Images of T cells and Lyve-1$^+$ lymphatic vessels are shown on the left, (magnification 20×; scale bar 50 μm). Center position and on the right distance T cells with respect to lymphatic vessels are shown. FIG. 5A, FIG. 5B, FIG. 5C, FIG. 5D, FIG. 5E, and FIG. 5G depict the means±SEM of at least 3 independent experiments. *p<0.05 by one-way ANOVA (FIG. 5A, FIG. 5B, FIG. 5C, FIG. 5D); by Student's t test (FIG. 5E, FIG. 5F, and FIG. 5G).

FIG. 6, comprising FIG. 6A through FIG. 6J, depicts the results of example experiments demonstrating that inhibition of the NIK pathway enhances T cell binding to LEC through integrin β4 and VCAM-1. FIG. 6A depicts time-lapse, 2-D microscopy of CD4 T cell migration across LEC. LEC layers in Boyden chambers were treated with control peptide or nciLT for 30 minutes at 37° C., washed and naïve CD4 CFSE-labeled T cells were loaded and monitored for 3 hours of live imaging during migration to CCL19 placed in bottom chamber. FIG. 6B depicts binding of naïve CD4 T cells to LEC pretreated with the indicated peptides with or without anti-integrin mAbs (2 μg/mL) or anti-VCAM-1 Ab (3 μg/mL) for 30 minutes at 37° C. FIG. 6C depicts LEC layers in Boyden chambers which were treated as in FIG. 6B, then naïve CD4 T cells migrated across LEC toward CCL19. FIG. 6D depicts LEC layers in Boyden chambers treated with the indicated peptides and blocking mAbs for 30 minutes at 37° C., washed, and naïve CD4 CFSE-labeled T cells loaded to migrate toward CCL19, and monitored for 3 hours of live imaging. Tracked image length (left); velocity (right). FIG. 6E depicts whole ear mount migration assay; pinnae injected with nciLT (10 nmol/ear) with or without anti-integrin β4 (5 μg) or anti-VCAM-1 Ab (15 μg) 30 minutes before transfer of naïve CSFE-labeled CD4 T cells (1×10$^6$/ear). After 16 hours, ears were stained for Lyve-1. Images of T cells and Lyve-1+lymphatic vessels (left). Magnification 20×; scale bar 50 Position (center) and distance (right) of T cells with respect to lymphatic vessels. FIG. 6F depicts footpad popliteal LN migration assay; hind footpads injected with the same doses of peptide or antibodies as in FIG. 6E, then 2×10$^6$ naïve CSFE-labeled CD4 T cells transferred. After 16 hours, popliteal LN collected and analyzed with flow cytometry. FIG. 6G depicts immunohistochemistry of cell surface integrins on primary LEC; LEC treated with 20 μM nciLT with or without anti-integrin β4 (2 μg/mL) prior to co-culture with naïve CD4-CFSE for 3 hours. Magnification 60×; scale bar 10 µm. FIG. 6H depicts expression of LTβR and NIK in primary LEC pretreated with 20 µM nciLT or 2 mg/ml LTβRIg for 30 minutes at 37° C., and co-cultured with iTreg-CFSE for 6 hours. 60×; scale bar 5 µm. FIG. 6H, FIG. 6I, and FIG. 6J depicts immunoblot of NIK activation in LEC incubated with various doses of purified iTreg or naïve CD4 T cells (FIG. 6I) or 5×10$^5$ wild type or LTα-deficient iTreg for 6 hours, after pretreatment with the indicated peptides (20 µM) or LTβRIg (2 µg/ml) (FIG. 6J). The bar graphs represent the relative band intensities (means±SD) from 3 independent experiments. *p<0.05 by one-way ANOVA.

FIG. 7A depicts flow cytometric analysis for LTα1β2 expression on naïve CD4, iTreg, IL-2-activated iTreg or LTα-deficient iTreg. FIG. 7B depicts an immunoblot of non-classical NFκB-NIK activation induced by co-culture of LEC with purified iTreg or LTα-deficient iTreg for 6 hours.

FIG. 8A through FIG. 8D, depicts the results of example experiments demonstrating that classical and non-classical inhibitors differentially affect gene expression. qRT-PCR of LTβR-induced VCAM-1 (FIG. 8A), CCL2 (FIG. 8B), CXCL12 (FIG. 8C), and CCL2 (FIG. 8D) in SVEC4-10 treated with indicated peptides (20 µM), NIKi (50 µM), or BAY11 (25 µM) and stimulated with anti-LTβR plus CL, as described in FIG. 4A. Means±SEM of 2 independent experiments. *p<0.05 by one-way ANOVA.

FIG. 10 depicts the results of example experiments as part of the Ingenuity Pathway Analysis, LEC activated with anti-LTβR/CL+nciLT vs no activation or blocking peptide treatment. Transcripts were analyzed using QIAGEN's Ingenuity® Pathway Analysis (IPA®, QIAGEN Redwood), with a focus on the top five (by p value) Canonical Pathways and Upstream Regulators. The upstream regulator analysis allows identification of potential regulators of genes belonging to a given set. IPA settings were—direct/indirect interaction and concordance of observed change of expression with reported change of expression in the IPA Knowledge database. Activation or inhibition status of upstream regulators (IPA) was determined by the z-score (>2, absolute value), based on the direction of fold change for transcripts in a given set.

FIG. 11 depicts the results of example experiments as part of the Ingenuity Pathway Analysis, LEC activated with anti-LTβR/CL+nciLT vs anti-LTβR/CL+control peptide treatment. Transcripts were analyzed as described for FIG. 10.

FIG. 12 depicts the results of example experiments as part of the Ingenuity Pathway Analysis, LEC activated with anti-LTβR/CL+nciLT vs anti-LTβR/CL+ciLT treatment. Transcripts were analyzed as described for FIG. 10.

FIG. 22, comprising FIG. 22A depicts in vitro DC migration to CCL21 through LEC treated with the indicated peptides. FIG. 22B depicts in vivo DC migration assay. i.d. injection of the indicated peptides to the shaved abdomen, followed 30 minutes later by FITC painting. After 16 hours, inguinal and axillary LNs collected and analyzed with flow cytometry. FIG. 22C depicts experimental design schematic 20 nmol of indicated peptides was injected i.d. in the abdomen (100 µl, day 0) or in each ear (30 µl, day 5 or day 7) 30 minutes before DNFB painting. FIG. 22D and FIG. 22E depicts CHS analyzed by ear swelling (FIG. 22D), or immunohistochemistry for CD11c$^+$ DC and CD3$^+$ T cells (FIG. 22E). Magnification 20×; scale bar 100 µm. Data represents three independent experiments with 3 mice/group. *p<0.05 by one-way ANOVA.

FIG. 23, comprising FIG. 23A depicts immunohistochemistry of cell surface integrins on primary LEC pretreated with or without nciLT (20 µM). Magnification 60×; scale bar 10 µm.

FIG. 23B depicts whole mount staining of wild type C57BL/6 ear pinnae for the indicated integrins. BV, blood vessel; LV, lymphatic vessel. Magnification 20×; scale bar 100 µm. FIG. 23C depicts flow cytometric analysis of integrin expression on primary LEC and purified naïve CD4 T cells. FIG. 23D depicts binding of naïve CD4 T cells to LEC pretreated with nciLT with (filled bars) or without anti-integrin mAbs (white bars) (2 µg/ml) for 30 minutes at 37° C. FIG. 23E and FIG. 23F depicts LEC layers treated as in (FIG. 23D); naïve CD4 T cells migrated across LEC toward CCL19. Migrated cells in lower chamber counted (FIG. 23E) or monitored for 3 hours of live imaging for track length (left) and velocity (right). Data representative of 3 independent experiments.

FIG. 24, comprising FIG. 24A depicts Flow cytometric analysis for LTα1β2 expression on naïve CD4, iTreg, or LTα-deficient iTreg. (b)

Immunohistochemistry of VCAM-1 and CCL21 in primary LECs were pretreated with nciLT (20 μM) or LTβRIg (2 mg/ml) for 30 minutes at 37° C., and co-cultured with iTreg-CFSE for 6 hours. Magnification 60×; scale bar 5 μm.

Figure 25:
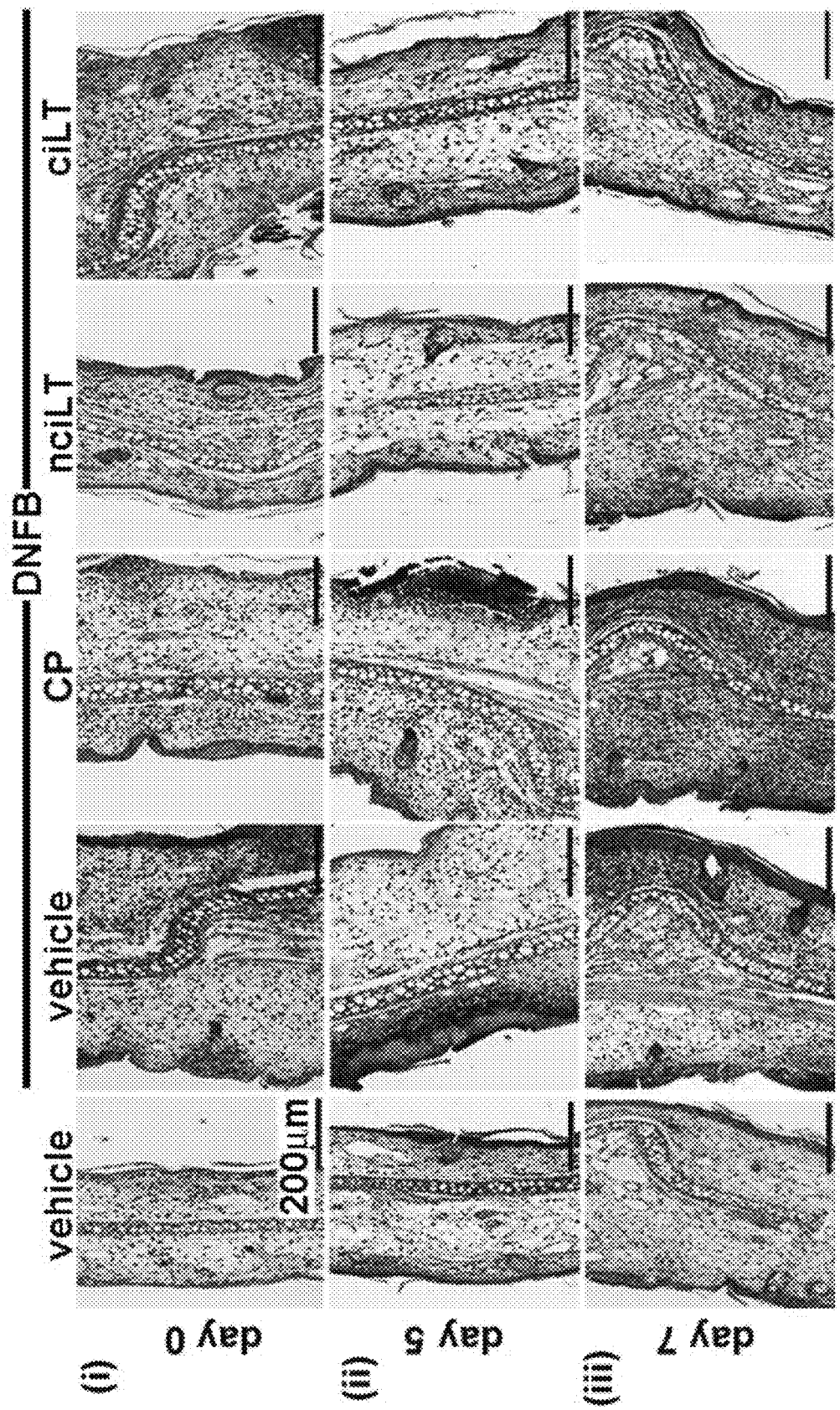

FIG. 25 depicts the results of example experiments demonstrating histological analysis of CHS. H&E images of ear pinnae CHS responses of the indicated groups, treatments and times. Data is representative of three independent experiments with 3 mice/group for each experiment. Magnification 20×, scale bar 200 μm.

Figures 3A, 3B, 3C:
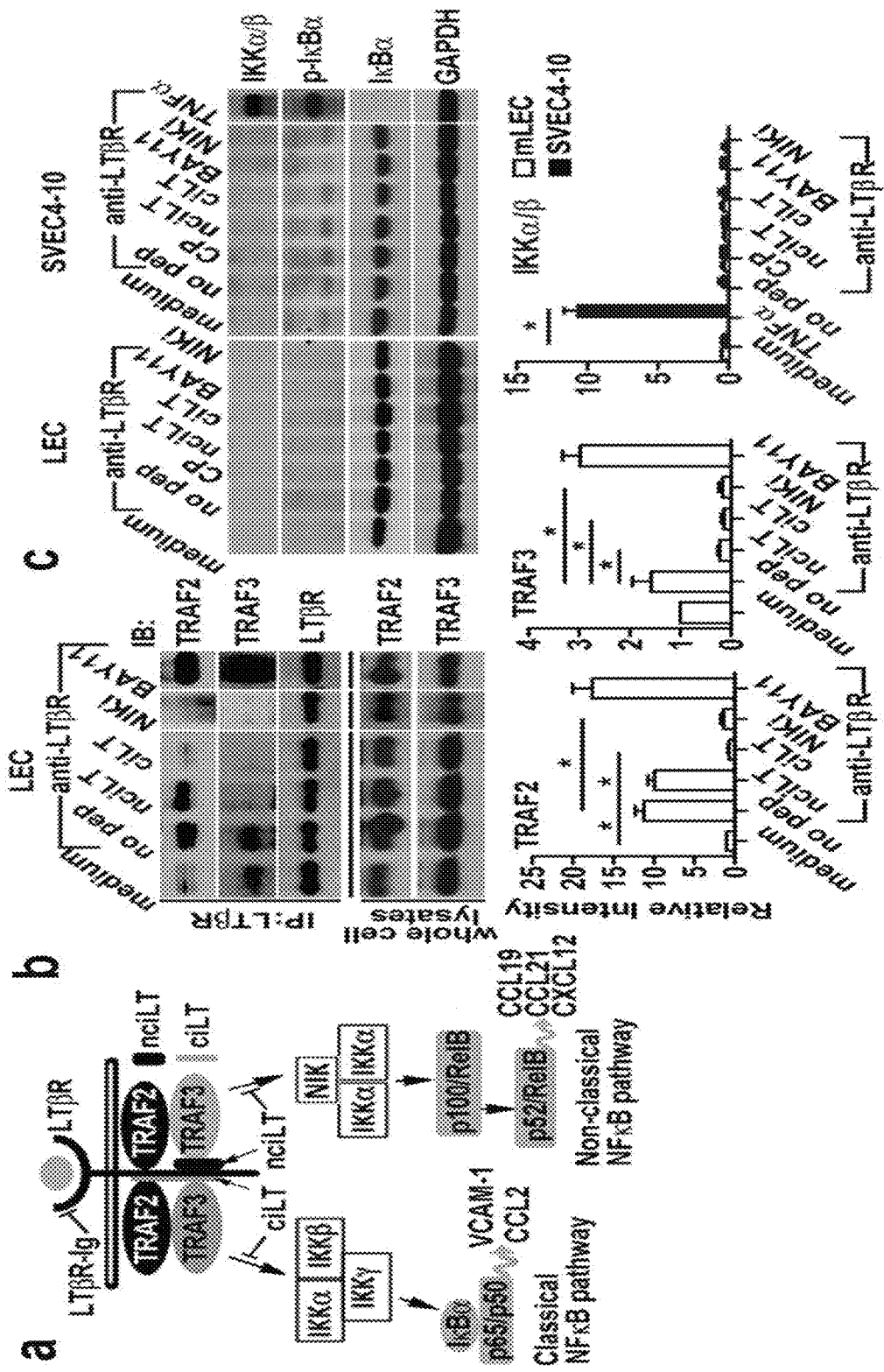
FIG. 3A through FIG. 3G, depicts the results of example experiments demonstrating the targeting of LTβR-mediated classical and non-classical NF-κB signaling pathways by LTβR-specific peptides.
Figures 3D, 3E:
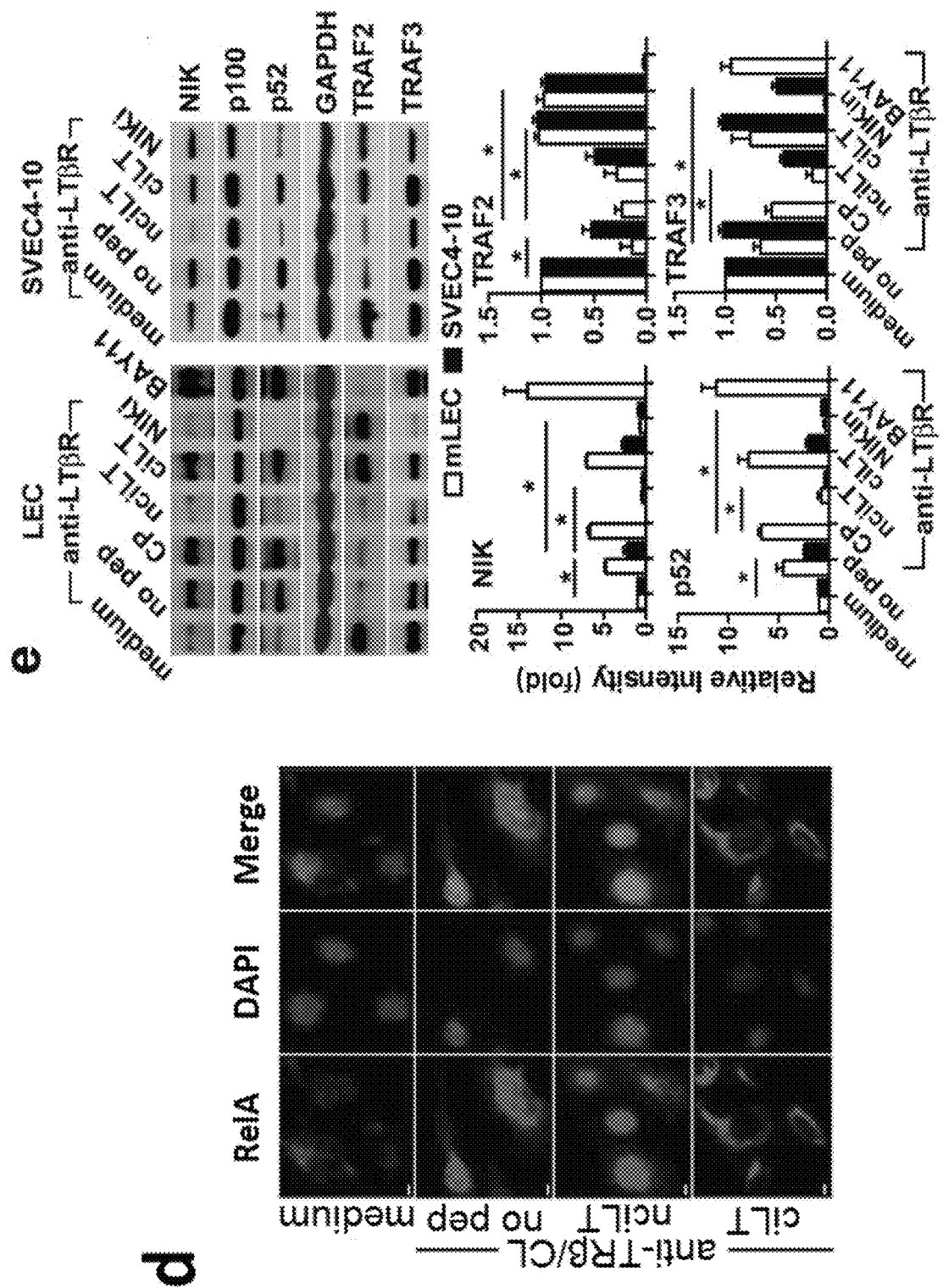
Figure 26:
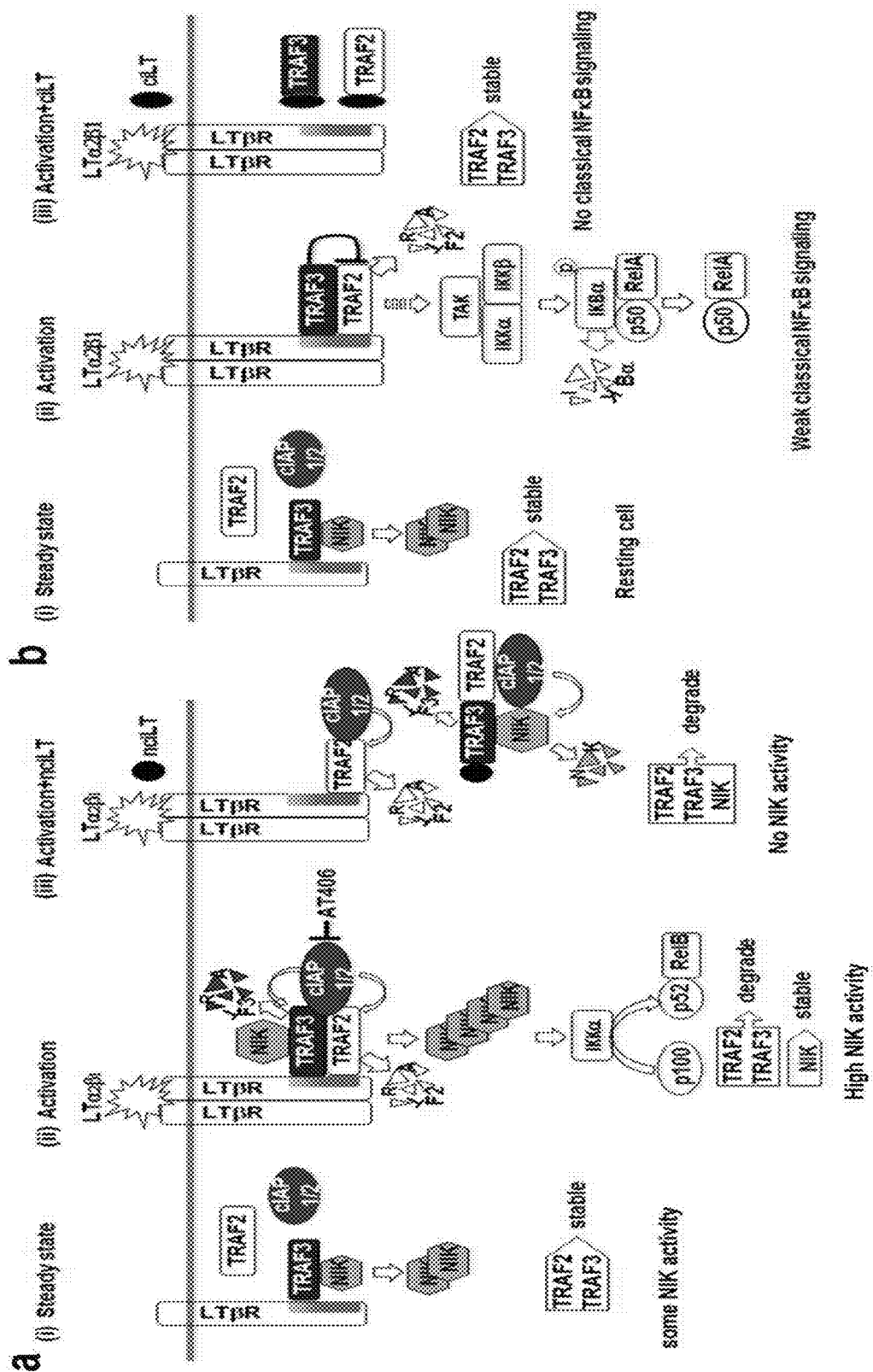

FIG. 26, comprising FIG. 26A through FIG. 26B, depicts the results of example experiments demonstrating a proposed model of TRAF regulation by the blocking peptides in LTβR-mediated NFκB pathways. FIG. 26A depicts non-classical NIK pathway predominates in LEC. FIG. 26B(i) depicts that in steady state, TRAF3 constitutively binds LTβR and is stabilized from degradation (FIG. 3B, FIG. 3C, and FIG. 3E). FIG. 26B (ii) depicts LTβR activation recruits TRAF2 and cIAP1/2, which together with TRAF3 and NIK form a signal complex; both TRAF2 and TRAF3 degraded by ubiquitination by cIAP1/2, leading to release of NIK from the complex. NIK activates IKKa which converts p100 to p52 (FIG. 1F). FIG. 26B(iii) depicts nciLT sequesters TRAF3 but not TRAF2 from the activated receptor, causing TRAF2 and TRAF3 degradation and preventing NIK activation (FIG. 3B, FIG. 3C, and FIG. 3E). (FIG. 26B) (i) depicts that in steady state, the classical pathway is not activated by LTβR (FIG. 1C and FIG. 3C). FIG. 26B(ii) depicts that with LTβR activation, TRAF2 recruited and activates TGFβ activating kinase 1 (TAK1) and the LTβR-classical NFκB pathway. TAK1 activates IKKα and IKKβ, which phosphorylate and degrade IκBα to release p50 and RelA into the nucleus (FIG. 1D and FIG. 1E). FIG. 26B (iii) depicts ciLT sequesters both TRAF2 and TRAF3 from LTβR (FIG. 3B), stabilizes TRAF3 and inhibits TRAF2 activation to block RelA nuclear translocation (FIG. 3D and FIG. 3E).

Figures 4A, 4B:
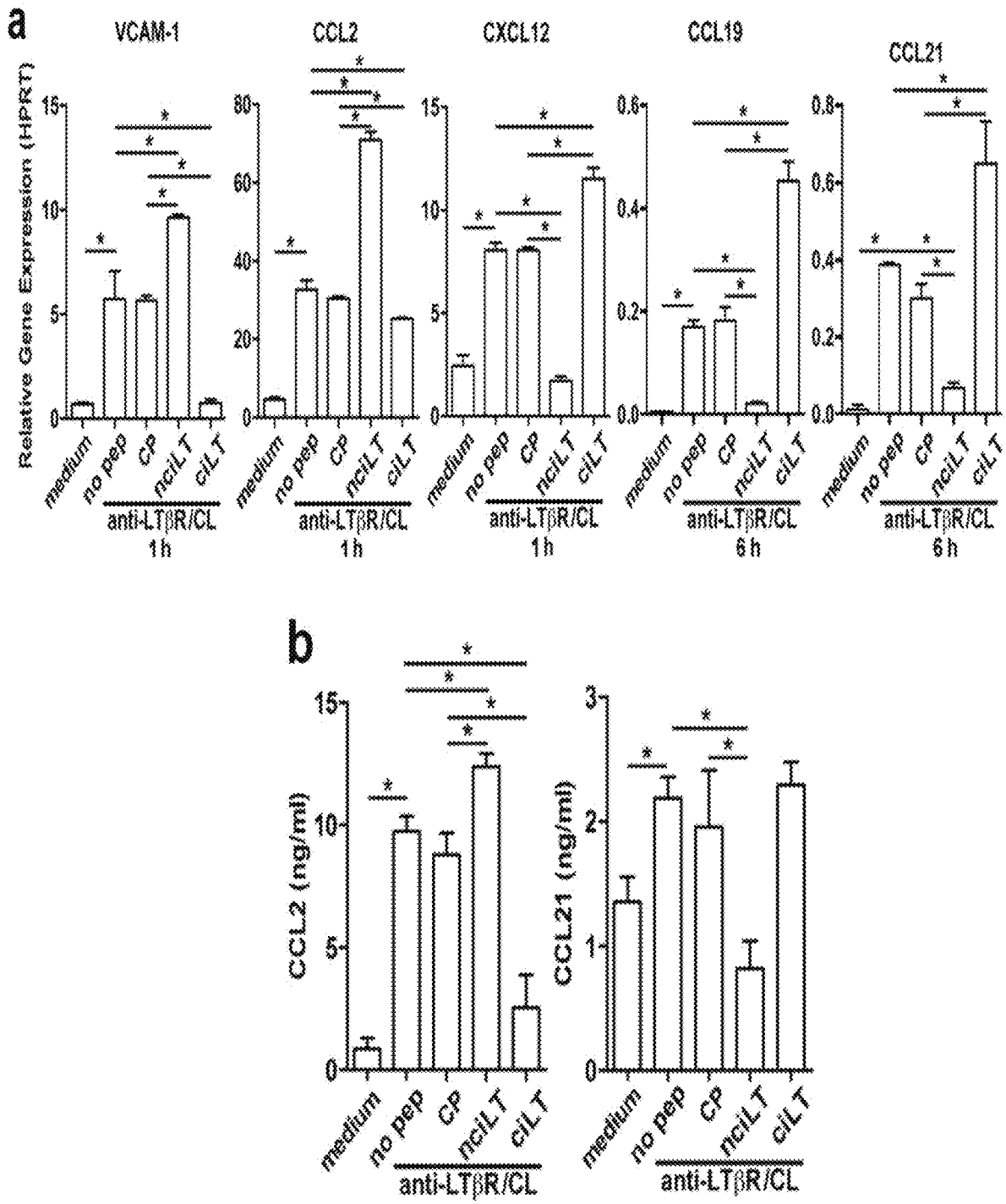
FIG. 4A through FIG. 4G, depicts the results of example experiments demonstrating the regulation of gene profiles by the LTβR-NFκB blocking peptides. LEC were stimulated with (FIG. 4A, FIG. 4B, and FIG. 4C) anti-LTβR mAb plus CL for the indicated times or (FIG. 4E) TNFα for 1 hour.
Figure 4C:
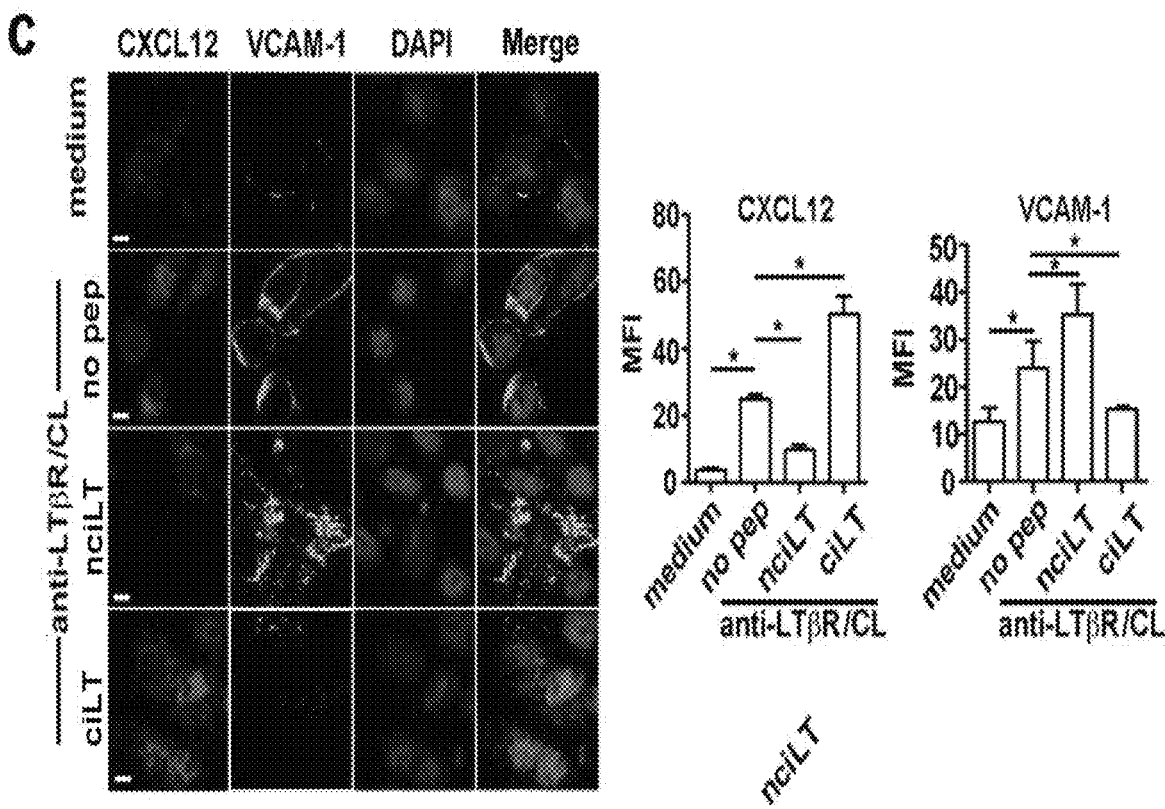
Figure 27:
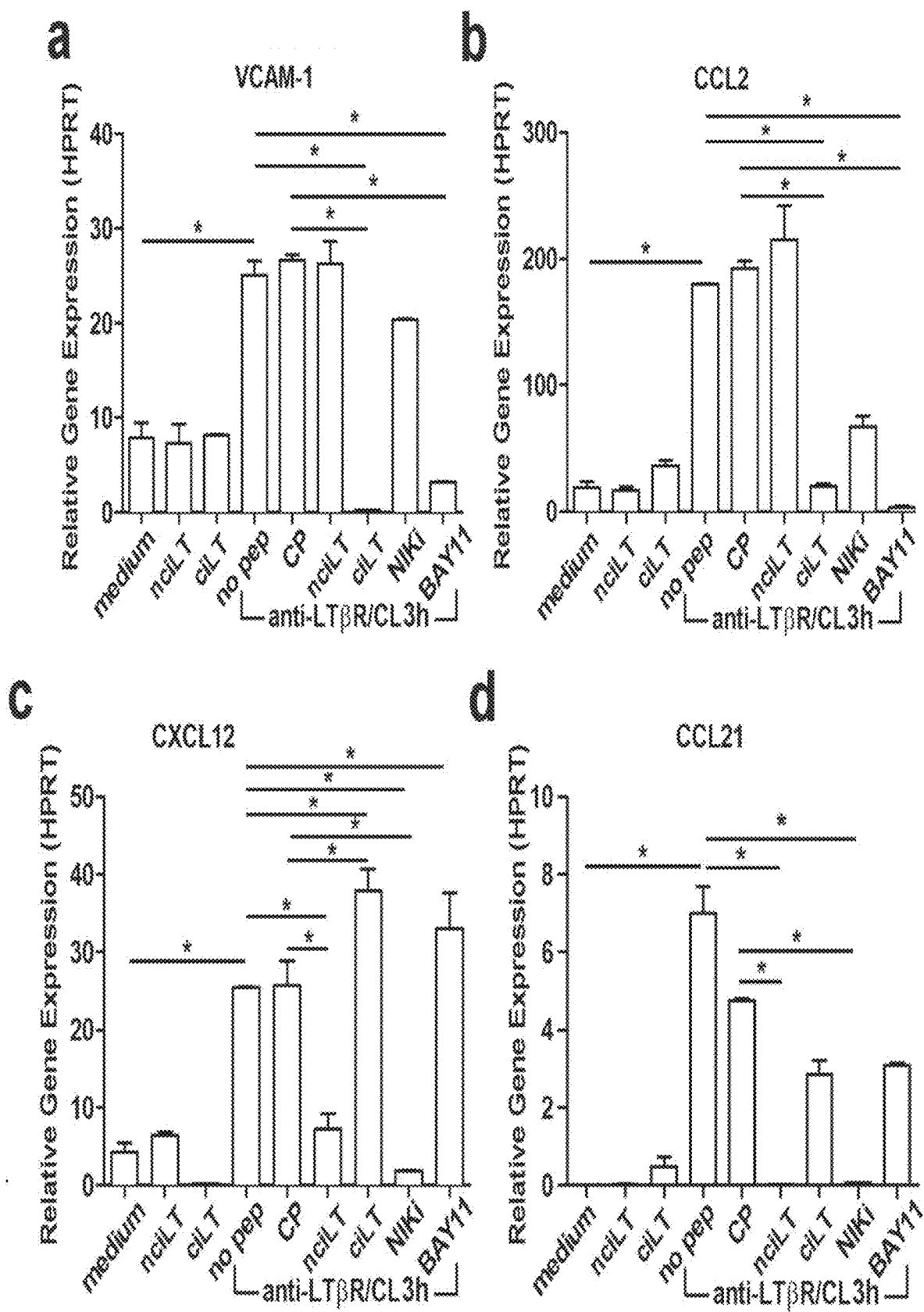

FIG. 27, comprising FIG. 27A through FIG. 27D, depicts the results of example experiments demonstrating qRT-PCR of LTβR-induced VCAM-1 (FIG. 27A), CCL2(FIG. 27B), CXCL12 (FIG. 27C), and CCL21(FIG. 27D) in SVEC4-10 treated with indicated peptides (20 μM), NIKi (50 μM), or BAY11 (25 μM) and stimulated with anti-LTβR plus CL, as described in FIG. 4A. Means±SEM of 2 independent experiments. *$p<0.05$ by one-way ANOVA.

DETAILED DESCRIPTION

The present invention relates to compositions and methods for modulating the LTβR-NFκB signaling pathway. In some embodiments, the invention provides compositions and methods for the selective inhibition of the classical LTβR-NFκB pathway or the non-classical LTβR-NFκB pathway. In some embodiments, the compositions and methods of the invention inhibit the non-classical LTβR-NFκB signaling pathway. In some embodiments, the compositions and methods of the invention inhibit the classical LTβR-NFκB signaling pathway. In some embodiments, the compositions and methods of the invention inhibit both the classical and non-classical LTβR-NFκB signaling pathways.

In some embodiments, the invention provides compositions and methods for decreasing cell motility by inhibiting the expression, activity, or both of one or more components of the non-classical LTβR-NFκB signaling pathway. In one embodiment, non-classical LTβR-NFκB signaling is decreased in lymphatic endothelial cells. In one embodiment, non-classical LTβR-NFκB signaling is decreased in cancer cells.

In some embodiments, the compositions comprise a polypeptide that inhibits LTβR-NFκB signaling. In some embodiments, the polypeptide comprises a cell-penetrating peptide (CPP) domain fused to a decoy peptide domain. In various embodiments, the decoy peptide is derived from an intracellular portion of LTβR. In one embodiment, the fusion peptide inhibits the expression, activity, or both of one or more components of the non-classical or classical LTβR-NFκB signaling pathway. In one embodiment, the peptide inhibits non-classical LTβR-NFκB signaling by inhibiting TRAF3 binding to LTβR. In one embodiment, the peptide inhibits classical LTβR-NFκB signaling by inhibiting TRAF2 and TRAF3 binding to LTβR.

In one aspect, the present invention provides compositions and methods for treating or preventing diseases and disorders in which decreased cell motility is desired. In various embodiments, the invention relates to compositions and methods for the treatment of tissue graft rejection, inflammation, contact hypersensitivity, and cancer. In one aspect, the present invention provides compositions and methods for increasing tissue graft survival and decreasing tissue graft rejection. In one aspect, the present invention provides compositions and methods for decreasing inflammation. In one aspect, the present invention provides compositions and methods for reducing tumor growth, reducing tumor cell invasion, reducing tumor cell metastasis, and reducing cancer recurrence. In various embodiments, the present invention provides compositions and methods for modulating an immune response.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

The term "antigen" or "Ag" as used herein is defined as a molecule that provokes an immune response and/or is capable of being bound by an antibody. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be synthesized or can be derived from a biological sample. Such a biological sample can include, but is not limited to a tissue sample, a tumor sample, a cell or a biological fluid.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, at least about 60% or at least about 80% of corresponding positions in each of the molecules are occupied by nucleotides which normally base pair with each other (e.g., A:T and G:C nucleotide pairs).

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, stomach cancer, prostate cancer, ovarian cancer, cervical cancer, skin cancer, pancreatic cancer, colorectal cancer, bladder cancer, renal cancer, liver cancer, brain cancer, lymphoma, leukemia, lung cancer and the like.

As used herein, "allogeneic" refers to a biological material derived from a genetically different individual of the same species as the individual into whom the material will be introduced.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

The term "cell penetrating peptide" refers to a peptide that, when contacted with the extracellular side of the cell membrane or cell wall of a cell, enters the intracellular region of the cell.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound which is sufficient to provide a beneficial effect to the subject to which the compound is administered. These terms may refer to an amount that is sufficient or effective to prevent or treat (delay or prevent the onset of, prevent the progression of, inhibit, alleviate, decrease or reverse) at least one sign or symptom of a disease or disorder.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein "endogenous" refers to any material from or produced inside an organism, cell, tissue or system.

As used herein, the term "exogenous" refers to any material introduced from or produced outside an organism, cell, tissue or system.

The term "fusion polypeptide" refers to a chimeric protein containing a protein of interest (e.g., luciferase) joined to a heterologous sequence (e.g., a non-luciferase amino acid or protein).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Inflammation" as used herein generally refers to acute or chronic accumulation of blood and/or immune cells in at least one area or portion of a subject's body.

"Graft" refers to a cell, tissue, organ or otherwise any biological compatible substrate for transplantation.

"Allograft" as used herein refers to a graft from a donor of the same species as the recipient, wherein the genetic background of the donor and recipient are different.

"Xenogeneic" refers to a biological substance, such as a graft, derived from an animal of a different species.

"Transplant" refers to a biocompatible substrate or a donor tissue, organ or cell, to be transplanted. An example of a transplant may include but is not limited to a tissue, a stem cell, a neural stem cell, a skin cell, bone marrow, and solid organs such as heart, pancreas, kidney, lung and liver.

"Allograft rejection" as used herein refers to the biological or immunological rejection of an allograft by the recipient of the allograft.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some versions contain an intron(s).

The terms "patient," "subject," "individual," and the like are used interchangeably herein, and refer to any animal, or cells thereof whether in vitro or in situ, amenable to the methods described herein. As used herein, a subject is a mammal such as a non-primate (e.g., cows, pigs, horses, cats, dogs, rats, etc.) and a primate (e.g., monkey and human), for example, a human. In some non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods. A host cell that comprises a recombinant polynucleotide is referred to as a "recombinant host cell." A gene which is expressed in a recombinant host cell wherein the gene comprises a recombinant polynucleotide, produces a "recombinant polypeptide."

As used herein, a "recombinant cell" is a host cell that comprises a recombinant polynucleotide.

"Ribozymes" as used herein are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, in certain instances hammerhead-type ribozymes may be more useful compared to tetrahymena-type ribozymes for inactivating specific mRNA species, and 18-base recognition sequences may be more useful compared to shorter recognition sequences which may occur randomly within various unrelated mRNA molecules. Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053).

By the term "specifically binds," as used herein, is meant a molecule, such as an antibody or peptide, which recognizes and binds to another molecule or feature, but does not substantially recognize or bind other molecules or features in a sample.

The phrase "inhibit," as used herein, means to reduce a molecule, a reaction, an interaction, a gene, an RNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an RNA stability, expression, function and activity, e.g., antagonists.

As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

Conventional notation is used herein to portray polypeptide sequences: the left-hand end of a polypeptide sequence is the amino-terminus; the right-hand end of a polypeptide sequence is the carboxyl-terminus.

"LTβR-derived peptide" refers to a peptide that comprises at least partial homology with lymphotoxin β receptor (LTβR) or a fragment thereof. In certain aspects, the LTβR-derived peptide is a fusion peptide or chimeric peptide having a domain comprising at least partial homology with lymphotoxin β receptor (LTβR) or a fragment thereof.

As used herein, a "peptidomimetic" is a compound containing non-peptidic structural elements that is capable of mimicking the biological action of a parent peptide. A peptidomimetic may or may not comprise peptide bonds.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "promoter" as used herein is defined as a DNA sequence recognized by the synthetic machinery of the cell, or introduced synthetic machinery, required to initiate the specific transcription of a polynucleotide sequence.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide that encodes or is specified by a gene, causes the gene product to be produced in a cell substantially only if the cell is a cell of the tissue type corresponding to the promoter.

A "therapeutic" treatment is a treatment administered to a subject who exhibits signs or symptoms of a disease or disorder, for the purpose of diminishing or eliminating those signs or symptoms.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods for modulating the LTβR-NFκB signaling pathway. In some embodiments, the invention provides compositions and methods for the selective inhibition of the classical LTβR-NFκB pathway or the non-classical LTβR-NFκB pathway. The present invention is based in part upon the development of peptide inhibitors that specifically inhibit each arm of the LTβR-NFκB signaling pathway (classical or non-classical).

In various embodiments, the invention provides compositions and methods for decreasing cell motility in the treatment of graft rejection, inflammation, contact hypersensitivity, and cancer. For example, in certain aspects, the present inventions provide compositions for increasing graft survival, reducing inflammation, reducing tumor growth, reducing contact hypersensitivity, reducing tumor cell invasion, reducing cancer metastasis, reducing cancer recurrence, and the like. The present invention is based in part upon the discovery, presented herein, that the non-classical NFκB signaling pathway (NIK-p100 arm of the LTβR signaling pathway; "non-classical LTβR-NFκB signaling pathway" as used herein) mediates immune cell migration and cancer cell migration.

In various embodiments, the compositions of the present invention comprise peptide inhibitors of the LTβR-NFκB pathway. In some embodiments, the peptide inhibitors provide selective inhibition of either the non-classical or classical LTβR-NFκB pathway. It is demonstrated herein that polypeptides comprising a TRAF-binding motif in LTβR (TGNIYIYNGPVL; SEQ ID NO:2, or PEEGAPGP; SEQ ID NO:3), can selectively inhibit either the non-classical (e.g., SEQ ID NO:2) or the classical (e.g., SEQ ID NO:3) LTβR-NFκB pathway.

In various embodiments, the compositions comprise a polypeptide that comprises a fragment of LTβR required for TRAF3 recruitment to the activated LTβR complex (non-classical pathway). In one embodiment, a peptide inhibitor that selectively inhibits the non-classical LTβR-NFκB pathway comprises TGNIYIYNGPVL; SEQ ID NO:2. In one embodiment, the peptide inhibitor is a fusion peptide comprising a cell-penetrating domain and a decoy domain. For example, in some embodiments, the decoy domain comprises SEQ ID NO:2. In one embodiment, the cell-penetrating domain comprises the N-terminal cell-penetrating sequence of the Drosophila antennapedia peptide (RQIKIWFQNRRMKWKK; SEQ ID NO:1). In one embodiment, the fusion peptide comprises the amino acid sequence of RQIKIWFQNRRMKWKKTGNIYIYNGPVL (SEQ ID NO:4), referred to herein as "nciLT." It is further demonstrated herein that a polypeptide comprising a domain of LTβR that binds TRAF3 (e.g., SEQ ID NO:2) is useful for inhibiting cell motility in models of immune cell and cancer cell migration.

In various embodiments, the compositions comprise a polypeptide that comprises a fragment of LTβR required for TRAF3 and TRAF2 recruitment to the activated LTβR complex (classical pathway). In one embodiment, a peptide inhibitor that selectively inhibits the classical LTβR-NFκB pathway comprises PEEGAPGP; SEQ ID NO:3. In one embodiment, the peptide inhibitor is a fusion peptide comprising a cell-penetrating domain and a decoy domain. For example, in some embodiments, the decoy domain comprises SEQ ID NO:3. In one embodiment, the cell-penetrating domain comprises the N-terminal cell-penetrating sequence of the Drosophila antennapedia peptide (RQIKIWFQNRRMKWKK; SEQ ID NO:1). In one embodiment, the fusion peptide comprises the amino acid sequence of RQIKIWFQNRRMKWKKPEEGAPGP (SEQ ID NO:5), referred to herein as "ciLT." It is further demonstrated herein that a polypeptide comprising a domain of LTβR that binds TRAF3 and TRAF4 (e.g., SEQ ID NO:3) is useful for inhibiting the classical LTβR-NFκB signaling pathway.

In one aspect, the present invention provides methods for reducing cell motility. In some embodiments, the method comprises administering to a cell, tissue, or subject a composition comprising a polypeptide comprising SEQ ID NO:2. In one embodiment, the method comprises administering the polypeptide to a lymphatic endothelial cell. In one embodiment, the method comprises administering the polypeptide to a cancer or tumor cell.

In one embodiment, the invention provides a method for reducing inflammation, reducing tissue graft rejection, reducing contact hypersensitivity, or reducing cancer cell migration, or metastasis. For example, in one embodiment, the method comprises administering to a subject in need thereof a composition comprising a polypeptide comprising SEQ ID NO:2.

In one embodiment, the invention provides a method for reducing classical LTβR-NFκB signaling. For example, in one embodiment, the method comprises administering to a subject in need thereof a composition comprising a polypeptide comprising SEQ ID NO:3.

Compositions

In one aspect, the present invention provides compositions for modulating the LTβR-NFκB signaling pathway.

In one aspect, the present invention provides compositions for inhibiting the non-classical arm of the LTβR-NFκB signaling pathway for decreasing cell motility. The compositions may be used, for example, to decrease inflammation, inhibit or prevent allograft rejection, inhibit or prevent cancer cell metastasis, and modulate an immune response. Exemplary agents include, but are not limited to, isolated nucleic acids, vectors, isolated peptides, peptidomimetics, antibodies, small molecules, and the like.

An agent that decreases non-classical LTβR-NFκB signaling is any agent that decreases the normal endogenous activity associated with one or more components of the non-classical LTβR-NFκB signaling pathway. In some embodiments, the agent modulates the level or activity of a non-classical LTβR-NFκB signaling pathway component by modulating the transcription, translation, splicing, degradation, enzymatic activity, binding activity, or combinations thereof, of one or more non-classical LTβR-NFκB signaling pathway components. In some embodiments, the agent negatively modulates an activator of non-classical LTβR-NFκB signaling. For example, in some embodiments the agent interferes with TRAF3 recruitment to LTβR.

In various embodiments, the composition that inhibits the non-classical LTβR-NFκB signaling pathway comprises a LTβR-derived peptide. For example, in some embodiments, the composition comprises a LTβR-derived peptide that is derived from the intracellular portion of LTβR and inhibits TRAF3 association with endogenous LTβR. In some embodiments, the LTβR-derived peptide is a fusion peptide comprising a cell-penetrating domain fused to a decoy domain, wherein the decoy domain is derived from an intracellular portion of LTβR. In one embodiment, the fusion peptide enters the cell and binds and sequesters TRAF3.

In one aspect, the present invention provides compositions for inhibiting the classical arm of the LTβR-NFκB signaling pathway. An agent that decreases classical LTβR-NFκB signaling is any agent that decreases the normal endogenous activity associated with one or more components of the classical LTβR-NFκB signaling pathway. In some embodiments, the agent modulates the level or activity of a classical LTβR-NFκB signaling pathway component by modulating the transcription, translation, splicing, degradation, enzymatic activity, binding activity, or combinations thereof, of one or more classical LTβR-NFκB signaling pathway components. In some embodiments, the agent negatively modulates an activator of classical LTβR-NFκB signaling. For example, in various embodiments, the agent interferes with TRAF3 and TRAF2 recruitment to LTβR.

In various embodiments, the composition that inhibits the classical LTβR-NFκB signaling pathway comprises a LTβR-derived peptide. For example, in some embodiments, the composition comprises a LTβR-derived peptide that is derived from the intracellular portion of LTβR and inhibits TRAF3 and TRAF2 association with endogenous LTβR. In some embodiments, the LTβR-derived peptide is a fusion peptide comprising a cell-penetrating domain fused to a decoy domain, wherein the decoy domain is derived from an intracellular portion of LTβR. In one embodiment, the fusion peptide enters the cell and binds and sequesters TRAF2 and TRAF3.

In one embodiment, the composition of the present invention comprises an isolated peptide comprising a cell-penetrating domain (CPD), or biologically functional fragment thereof. In one embodiment, the CPD is a cell-penetrating peptide (CPP). The composition may comprise, for example, the N-terminal cell-penetrating sequence of the Drosophila antennapedia peptide (RQIKIWFQNRRMKWKK; SEQ ID NO:1).

In one embodiment, the isolated peptide comprising a CPP further comprises a fragment or portion of LTβR, for example, a portion of LTβR required for TRAF3 binding to LTβR (TGNIYIYNGPVL; SEQ ID NO:2), creating, for example, the fusion peptide ("nciLT") (RQIKIWFQNRRMKWKKTGNIYIYNGPVL; SEQ ID NO:4). In another embodiment, the isolated peptide comprising a CPP further comprises a fragment or portion of LTβR, for example, a portion of LTβR required for TRAF3 and TRAF2 binding to LTβR (PEEGAPGP; SEQ ID NO:3), creating, for example, the fusion peptide ("ciLT") (RQIKIWFQNRRMKWKKPEEGAPGP; SEQ ID NO:5). However, the present invention is not limited to these particular sequences. Rather the present invention encompasses any CPP from any source, combined with any peptide that modulates one or more of the classical or non-classical LTβR-NFκB signaling pathways.

Exemplary CPPs include but are not limited to, the HIV transactivator (TAT) protein, EGF (epidermal growth factor)-derived peptides, such as CMHIESLDSYTC (SEQ ID NO:6) and CMYIEALDKYAC (SEQ ID NO:7); TGF-beta (transforming growth factor beta)-derived peptides; peptides derived from PDGF (platelet-derived growth factor) or PDGF-2; peptides derived from IGF-I (insulin-like growth factor), IGF-II; FGF (fibroblast growth factor)-derived peptides, and mastoparan, or fragments thereof. In various embodiments, the CPD comprises one or more peptides for receptor-mediated transcytosis, including, but not limited to, a histone, insulin, transferrin, basic albumin, prolactin and insulin-like growth factor I (IGF-I), insulin-like growth factor II (IGF-II) or other growth factors.

The cell penetrating peptide (CPP) may translocate across the cell membrane by any mechanism. One mechanism involves pH-dependent membrane binding. For a CPP that assumes a helical conformation at an acidic pH, the cell penetrating peptide acquires the property of amphiphilicity, e.g., it has both hydrophobic and hydrophilic interfaces. More specifically, within a pH range of approximately 5.0-5.5, a cell penetrating peptide forms an alpha-helical, amphiphilic structure that facilitates insertion of the moiety into a target membrane. An alpha-helix-inducing acidic pH environment may be found, for example, in the low pH environment present within cellular endosomes. Such cell penetrating peptides can be used to facilitate transport of LTβR-derived peptides, taken up by an endocytic mechanism, from endosomal compartments to the cytoplasm.

One pH-dependent membrane-binding cell penetrating peptide includes a high percentage of helix-forming residues, such as glutamate, methionine, alanine and leucine. In addition, a cell penetrating peptide sequence may include ionizable residues having pKa's within the range of pH 5-7, so that a sufficient uncharged membrane-binding domain will be present within the peptide at pH 5 to allow insertion into the target cell membrane.

A particular pH-dependent membrane-binding cell penetrating peptide in this regard is aa1-aa2-aa3-EAALA (EALA)4-EALEALAA—amide (SEQ ID NO:8), which represents a modification of the peptide sequence of Subbarao et al. (Biochemistry 26:2964, 1987). Within this peptide sequence, the first amino acid residue (aa1) may be a unique residue, such as cysteine or lysine, that facilitates chemical conjugation of the cell penetrating peptide to a targeting protein conjugate. Amino acid residues 2-3 may be selected to modulate the affinity of the cell penetrating peptide for different membranes. For instance, if both residues 2 and 3 are lys or arg, the cell penetrating peptide will have the capacity to bind to membranes or patches of lipids having a negative surface charge. If residues 2-3 are neutral amino acids, the cell penetrating peptide will insert into neutral membranes.

Yet other cell penetrating peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary cell penetrating peptides may be modified through attachment of substituents that enhance the alpha-helical character of the cell penetrating peptide at acidic pH.

Yet another class of cell penetrating peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such cell penetrating peptides may be modeled after sequences identified in, e.g., Pseudomonas exotoxin A, clathrin, or Diphtheria toxin.

Pore-forming proteins or peptides may also serve as cell penetrating peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of a cell penetrating peptide may be sufficient for translocation of the peptide, across cell membranes. However, translocation may be improved by attaching to the cell penetrating peptide a substrate for intracellular enzymes (i.e., an "accessory peptide"). It is exemplary that an accessory peptide be attached to a portion(s) of the cell penetrating peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (SEQ ID NO:9) (Eubanks et al., in: Peptides, Chemistry and Biology, Garland Marshall (ed.), ESCOM, Leiden, 1988, pp. 566-69) In this construct, a cell penetrating peptide would be attached to the C-terminus of the accessory peptide, since the N-terminal glycine is critical for the accessory moiety's activity. This hybrid peptide, upon attachment to an E2 peptide or peptidomimetic at its C-terminus, is N-myristylated and further anchored to the target cell membrane, e.g., it serves to increase the local concentration of the peptide at the cell membrane.

To further illustrate use of an accessory peptide, a phosphorylatable accessory peptide is first covalently attached to the C-terminus of a cell penetrating peptide and then incorporated into a fusion protein. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) Ann. Rev. Biochem. 56:63-87). Accessory peptides that comprise the sequence x-NLT-x thus will enhance target cell retention of corresponding polypeptide.

In another embodiment of this aspect of the invention, an accessory peptide can be used to enhance interaction of the LTβR-derived peptides with the target cell. Exemplary accessory peptides in this regard include peptides derived from cell adhesion proteins containing the sequence "RGD", or peptides derived from laminin containing the sequence CDPGYIGSRC (SEQ ID NO:10). Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type I, lambda receptor of *E. Coli*, fibrinogen and Sindbis coat protein (E. Ruoslahti, Ann. Rev. Biochem. 57:375413, 1988). Cell surface receptors that recognize RGD sequences have been grouped into a superfamily of related proteins designated "integrins". Binding of "RGD peptides" to cell surface integrins will promote cell-surface retention, and ultimately translocation, of the polypeptide.

As described above, the internalizing and accessory peptides can each, independently, be added to the LTβR-derived peptides by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, such as an RGD sequence, it may be necessary to include a secretion signal sequence to direct export of the fusion protein from its host cell. In exemplary embodiments, the secretion signal sequence is located at the extreme N-terminus, and is (optionally) flanked by a proteolytic site between the secretion signal and the rest of the fusion protein.

In the generation of fusion polypeptides including the subject LTβR-derived peptides, it may be necessary to include unstructured linkers in order to ensure proper folding of the various peptide domains. Many synthetic and natural linkers are known in the art and can be adapted for use in the present invention, including the (Gly$_3$Ser)$_4$ linker.

The peptides of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The invention should also be construed to include any form of a fusion peptide having a decoy portion having substantial homology to a LTβR-derived peptide disclosed herein. In some embodiments, a peptide which is "substantially homologous" is about 50% homologous, or about 70% homologous, or about 80% homologous, or about 90% homologous, or about 95% homologous, or about 99% homologous to the amino acid sequence of a LTβR-derived peptide disclosed herein.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (e.g., a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, for example, different from the original sequence in less than 40% of residues per segment of interest, different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence. The present invention includes amino acid sequences that are at least 60%, 65%, 70%, 72%, 74%, 76%, 78%, 80%, 90%, 91%, 92%, 93%, 94%, 95%, 96%, 97%, 98%, or 99% similar or identical to the original amino acid sequence. The degree of identity between two peptides is determined using computer algorithms and methods that are widely known for the persons skilled in the art. The identity between two amino acid sequences may be determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of the LTβR-derived peptide.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulfide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides comprising a LTβR-derived peptide fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue or cell type (e.g., lymphatic endothelial cells, immune cells, cancer cells). A targeting domain may target the peptide of the invention to a cellular component.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins comprise the LTβR-derived peptide fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad. Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

In some embodiments, the composition increases the expression of a biologically functional fragment of LTβR. For example, in one embodiment, the composition comprises an isolated nucleic acid sequence encoding a biologically functional fragment of LTβR. As would be understood in the art, a biologically functional fragment is a portion or portions of a full length sequence that retain all or part of the biological function of the full length sequence. Thus, a biologically functional fragment of LTβR comprises a peptide that retains at least the function of binding TRAF3 or binding TRAF2 and TRAF3.

In one embodiment, the isolated nucleic acid sequence encodes a functional fragment of LTβR. In various embodiments, the isolated nucleic acid sequence encodes a LTβR-derived peptide comprising an amino acid sequence selected from SEQ ID NOs: TGNIYIYNGPVL (SEQ ID NO:2), and PEEGAPGP (SEQ ID NO:3).

Further, the invention encompasses an isolated nucleic acid encoding a peptide having substantial homology to SEQ ID NO: 2, SEQ ID NO: 3, SEQ ID NO: 4, or SEQ ID NO: 5 or a peptide derived from either or both of these sequences. In some embodiments, the isolated nucleic acid sequence encodes LTβR or a LTβR peptide mimetic having at least 75%, 80%, 85%, 90%, 91%, 92%, 93%, 94%, 95%, 96%, 97%, 98%, or 99% sequence homology with an amino acid sequence selected from SEQ ID NO: 2, SEQ ID NO: 3, SEQ ID NO: 4, OR SEQ ID NO: 5.

The isolated nucleic acid sequence encoding the LTβR-derived peptide can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding a LTβR-derived peptide, or functional fragment thereof. In one embodiment, the composition comprises an isolated RNA molecule encoding a LTβR-derived peptide, or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In some backbone-modified ribonucleotides the phosphoester group connecting to adjacent ribonucleotides is replaced by a modified group, e.g., of phosphothioate group. In some sugar-modified ribonucleotides, the 2' OHgroup is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In some embodiments, a nucleic acid molecule of the invention can have enhanced resistance to nucleases. For increased nuclease resistance, a nucleic acid molecule can include, for example, 2'-modified ribose units and/or phosphorothioate linkages. For example, the 2' hydroxyl group (OH) can be modified or replaced with a number of different "oxy" or "deoxy" substituents. For increased nuclease resistance, the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example, as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, e.g., different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding a LTβR-derived peptide, or a functional fragment thereof is typically achieved by operably linking a nucleic acid encoding the LTβR-derived peptide, or a functional fragment thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

In some embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulate expression of the gene contained therein. Typically, enhancers are bound with protein factors to enhance the transcription of a gene. An enhancer may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a LTβR-derived peptide, or a functional fragment thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the present invention provides a delivery vehicle comprising a LTβR-derived peptide, or a functional fragment thereof, or a nucleic acid molecule encoding a LTβR-derived peptide, or a functional fragment thereof. Exemplary delivery vehicles include, but are not limited to, microspheres, microparticles, nanoparticles, polymerosomes, liposomes, and micelles. For example, in some embodiments, the delivery vehicle is loaded with a LTβR-derived peptide, or a functional fragment thereof, or a nucleic acid molecule encoding a LTβR-derived peptide, or a functional fragment thereof. In some embodiments, the delivery vehicle provides for controlled release, delayed release, or continual release of its loaded cargo. In some embodiments, the delivery vehicle comprises a targeting moiety that targets the delivery vehicle to a treatment site.

The present invention also provides pharmaceutical compositions comprising one or more of the compositions described herein. Formulations may be employed in admixtures with conventional excipients, i.e., pharmaceutically acceptable organic or inorganic carrier substances suitable for administration to the subject. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, intratumoral, subcutaneous, intramuscular, or intraperitoneal injection, or by infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to about 5.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly exemplary preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Useful antioxidants for some compounds are BHT, BHA, alpha-tocopherol and ascorbic acid in the exemplary range of about 0.01% to 0.3%, BHT in the range of 0.03% to 0.1% by weight by total weight of the composition. In one embodiment, the chelating agent is present in an amount of from 0.01% to 0.5% by weight by total weight of the composition. In some embodiments, chelating agents include edetate salts (e.g. disodium edetate) and citric acid in the weight range of about 0.01% to 0.20% or in the range of 0.02% to 0.10% by weight by total weight of the composition. The chelating agent is useful for chelating metal ions in the composition that may be detrimental to the shelf life of the formulation. While BHT and disodium edetate are the exemplary antioxidant and chelating agent respectively for some compounds, other suitable and equivalent antioxidants and chelating agents may be substituted therefore as would be known to those skilled in the art.

The relative amounts of the active ingredient (e.g., an inhibitor of the invention as described elsewhere herein), the pharmaceutically acceptable carrier, and any additional ingredients in a pharmaceutical composition of the invention will vary, depending upon the identity, size, and condition of the individual treated and further depending upon the route by which the composition is to be administered. By way of example, the composition may comprise between 0.1% and 100% (w/w) active ingredient. In various embodiments, the composition comprises at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% (w/w) active ingredient.

The pharmaceutical compositions useful for practicing the invention may be administered to deliver a dose of the active ingredient of at least about 1 ng/kg, at least about 5 ng/kg, at least about 10 ng/kg, at least about 25 ng/kg, at least about 50 ng/kg, at least about 100 ng/kg, at least about 500 ng/kg, at least about 1 µg/kg, at least about 5 µg/kg, at least about 10 µg/kg, at least about 25 µg/kg, at least about 50 µg/kg, at least about 100 µg/kg, at least about 500 µg/kg, at least about 1 mg/kg, at least about 5 mg/kg, at least about 10 mg/kg, at least about 25 mg/kg, at least about 50 mg/kg, at least about 100 mg/kg, at least about 200 mg/kg, at least about 300 mg/kg, at least about 400 mg/kg, and at least about 500 mg/kg of body weight of the subject. In one embodiment, the invention administers a dose of the active ingredient which results in a concentration of the active ingredient of at least about 1 pM, at least about 10 pM, at least about 100 pM, at least about 1 nM, at least about 10 nM, at least about 100 nM, at least about 1 µM, at least about 2 µM, at least about 3 µM, at least about 4 µM, at least about 5 µM, at least about 6 µM, at least about 7 µM, at least about 8 µM, at least about 9 µM and at least about 10 µM in an individual. In another embodiment, the invention envisions administration of a dose of the active ingredient which results in a concentration of the active ingredient of between at least about 1 pM, at least about 10 pM, at least about 100 pM, at least about 1 nM, at least about 10 nM, at least about 100 nM, at least about 1 µM, at least about 2 µM, at least about 3 µM, at least about 4 µM, at least about 5 µM, at least about 6 µM, at least about 7 µM, at least about 8 µM, at least about 9 µM and at least about 10 µM in the plasma of an individual.

In some embodiments, the pharmaceutical compositions useful for practicing the invention may be administered to deliver a dose of the active ingredient of no more than about 1 ng/kg, no more than about 5 ng/kg, no more than about 10 ng/kg, no more than about 25 ng/kg, no more than about 50 ng/kg, no more than about 100 ng/kg, no more than about 500 ng/kg, no more than about 1 µg/kg, no more than about 5 µg/kg, no more than about 10 µg/kg, no more than about 25 µg/kg, no more than about 50 µg/kg, no more than about 100 µg/kg, no more than about 500 µg/kg, no more than about 1 mg/kg, no more than about 5 mg/kg, no more than about 10 mg/kg, no more than about 25 mg/kg, no more than about 50 mg/kg, no more than about 100 mg/kg, no more than about 200 mg/kg, no more than about 300 mg/kg, no more than about 400 mg/kg, and no more than about 500 mg/kg of body weight of the subject. In one embodiment, the invention administers a dose of the active ingredient which results in a concentration of the active ingredient of no more than about 1 pM, no more than about 10 pM, no more than about 100 pM, no more than about 1 nM, no more than about 10 nM, no more than about 100 nM, no more than about 1 µM, no more than about 2 µM, no more than about 3 µM, no more than about 4 µM, no more than about 5 µM, no more than about 6 µM, no more than about 7 µM, no more than about 8 µM, no more than about 9 µM and no more than about 10 µM in an individual. In another embodiment, the invention envisions administration of a dose of the active ingredient which results in a concentration of the active ingredient between no more than about 1 pM, no more than about 10 pM, no more than about 100 pM, no more than about 1 nM, no more than about 10 nM, no more than about 100 nM, no more than about 1 µM, no more than about 2 µM, no more than about 3 µM, no more than about 4 µM, no more than about 5 µM, no more than about 6 µM, no more than about 7 µM, no more than about 8 µM, no more than about 9 µM and no more than about 10 µM in the plasma of an individual. Also contemplated are dosage ranges between any of the doses disclosed herein.

Typically, dosages which may be administered in a method of the invention to a subject, in some embodiments a human, range in amount from 0.5 µg to about 50 mg per kilogram of body weight of the subject. While the precise dosage administered will vary depending upon any number of factors, including but not limited to, the type of subject and type of disease state being treated, the age of the subject and the route of administration. In some embodiments, the dosage of the compound will vary from about 1 µg to about 10 mg per kilogram of body weight of the subject. In other embodiments, the dosage will vary from about 3 µg to about 1 mg per kilogram of body weight of the subject.

Liquid suspensions may be prepared using conventional methods to achieve suspension of the composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para hydroxybenzoates, ascorbic acid, and sorbic acid.

In some embodiments, the composition comprises a pharmaceutical composition suitable for topical administration. An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions.

Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Treatment Methods

The present invention provides methods for treating or preventing a disease or disorder in a subject in need thereof, in which decreased cell motility would be beneficial. Exemplary diseases and disorders treated or prevented by way of the present invention include, but are not limited to graft rejection, inflammation, contact hypersensitivity, and cancer. In some embodiments, the methods of treatment or prevention include inhibiting cell motility by administering to the subject an of the non-classical LTβR-NFκB signaling pathway. In some embodiments, the methods of treatment or prevention include inhibiting the classical LTβR-NFκB signaling pathway, comprising administering to a subject an inhibitor of the classical LTβR-NFκB signaling pathway.

The method is not limited to a particular type of graft transplantation. The transplant graft may be any suitable cell, tissue, or organ to be transplanted into a recipient subject, including, but not limited to, lung, heart, kidney, liver, pancreas, intestine, multivisceral transplant (e.g., liver, stomach, duodenum, pancreases and small bowel), and portions thereof.

The present invention provides method for improving survival of transplanted grafts and organs comprising (a) pretreating (e.g., ex vivo) transplant graft with one or more LTβR-derived peptides, or (b) post-treating (e.g., in vivo) transplant graft or transplant recipient with one or more LTβR-derived peptides to increase graft survival and decrease biological or immune rejection of the graft.

In one embodiment, the method comprises contacting transplant graft with a composition comprising one or more LTβR-derived peptides, or nucleic acids encoding one or more LTβR-derived peptides. In one embodiment, the method comprises administering to the transplant graft recipient a composition comprising one or more LTβR-derived peptides, or nucleic acids encoding one or more LTβR-derived peptides.

The present invention encompasses the use of LTβR-derived peptides or LTβR-derived peptide mutants, fragments, homologs, or fusion peptides that retain the function of improving transplant graft viability.

In some embodiments, the LTβR-derived peptides have an amino acid sequence comprising at least one of SEQ ID NO:2 and SEQ ID NO:3. In some embodiments, the LTβR-derived peptides have an amino acid sequence comprising at least one of SEQ ID NO:4 and SEQ ID NO:5.

In some embodiments, the transplant graft is allogeneic. For example, in some embodiments, where the recipient is a human, the donor from which the graft transplant is harvested is a human. For example, in some embodiments, the donor is characterized by brain death. In some embodiments, "brain death" is defined as the total cessation of brain function, including brain stem function, e.g., wherein there is no oxygen or blood flow to the brain, or wherein the brain no longer functions in any manner and will never function again.

In some embodiments, the donor is not diagnosed as having a chronic, transmissible, or infectious physical ailment, e.g., for which pharmacological intervention is or would have been suitable. In some embodiments, the donor is not currently and/or has not been diagnosed with diabetes, cancer, high blood pressure, kidney disease, or cardiovascular disease, e.g., atherosclerosis or heart disease.

In some embodiments, the transplant graft is xenogeneic. For example, in some embodiments, where the recipient is a human, the donor is a non-human animal. For example, the donor may be a pig or primate, such as a genetically altered animal. In some such embodiments, the donor is an animal that has been genetically modified such that proteins on the surface of the animal's organs and/or cells are recognized as compatible by a human immune system. For example, the donor may be an animal that has been genetically modified such that proteins on the surface of the animal's organs and/or cells are recognized as human by the human immune system, so the transplant graft is not attacked when transplanted.

In some embodiments, the method comprises contacting the transplant graft with a preservation solution wherein the preservation solution comprises a LTβR-derived peptide, or variant thereof; a nucleic acid molecule encoding a LTβR-derived peptide, or variant thereof; or a cell expressing a LTβR-derived peptide, or variant thereof. In some embodiments, the preservation solution comprises a LTβR-derived peptide, or a variant thereof at a concentration of 0.1 ng/mL to 1 gram/mL. In some embodiments, the method comprises administering to the transplant graft recipient a preservation solution wherein the preservation solution comprises a LTβR-derived peptide, or variant thereof; a nucleic acid molecule encoding a LTβR-derived peptide, or variant thereof; or a cell expressing a LTβR-derived peptide, or variant thereof. In some embodiments, the preservation solution comprises a LTβR-derived peptide, or a variant thereof at a concentration of 0.1 ng/mL to 1 gram/mL.

In some embodiments, the organ preservation solution further comprises potassium, sodium, magnesium, calcium, phosphate, sulphate, glucose, citrate, mannitol, histidine, tryptophan, alpha-ketoglutaric acid, lactobionate, raffinose, adenosine, allopurinol, glutathione, glutamate, insulin, dexamethasone, hydroxyethyl starch, bactrim, trehalose, gluconate, or combinations thereof. In some embodiments, the preservation solution comprises sodium, potassium, magnesium, or combinations thereof. In some embodiments, the preservation solution is free or substantially free of cells, coagulation factors, nucleic acids such as DNA, and/or plasma proteins. In some embodiments, the preservation solution is sterile. In some embodiments, organ preservation solution comprises an aqueous solution. In some embodiments, the preservation solution comprises a perfluorocarbon, such as a perfluoro hydrocarbon or a perfluoroalkylamine. Exemplary perfluorocarbons are described in Transplantation, 74(12), 1804-1809, Dec. 27, 2002 and Am. Assoc. of Nurse Anesthetists Journal, 74(3): 205-211, June 2007, the compounds in which are incorporated herein by reference. The preservation solution may be any suitable preservation solution known in the art. Examples of such preservation solutions include, but are not limited to, University of Wisconsin solution, Krebs-Henseleit solution, Celsior solution, St. Thomas Hospital 2 solution, Ringer-lactate solution, Collins solution, Euro-Collins solution, Stanford solution, Ross-Marshall citrate solution, phosphate-buffered sucrose solution, Kyoto ET solution, or Bretschneider histidine tryptophan ketoglutarate (HTK) solution.

The transplant graft may be contacted with (or administered) the composition comprising a LTβR-derived peptide, or variant thereof; a nucleic acid molecule encoding a LTβR-derived peptide, or variant thereof; or a cell expressing a LTβR-derived peptide, or variant thereof at any point during the transplantation process. For example, the composition may be administered by flushing the transplant graft, continuously perfusing the transplant graft, or intermittently perfusing through the blood vessels of the transplant graft while the transplant graft is still in a donor's body, during the removal of the transplant graft from a donor's body, after the transplant graft is removed from a donor's body, while the transplant graft is being transplanted into a recipient, immediately after the transplant graft is transplanted into a recipient, or any combination thereof.

In some embodiments, the composition further comprises one or more additional agents that aid in the viability or survival of the transplant graft. Exemplary additional agents include, but is not limited to, anti-inflammatories, anti-coagulants, anti-thrombotics, thrombolytics, anti-platelets, hormones, vitamins, and the like.

The perfusion of the transplant graft may be conducted using any methodology or equipment known in the art. In some embodiments, for intestinal grafts, the superior mesenteric artery, celiac artery, or inferior mesenteric artery are cannulated and perfused with the composition described herein, and effluent is captured in a portal vein cannula or gravity drainage from an open venous system. In some embodiments, for a composite tissue graft, the arterial supply is individually cannulated and perfused with the composition described herein, and effluent captured in a vein cannula, or by gravity drainage from an open venous system.

The present invention can be used to treat or ameliorate the effects of a wide variety of diseases or disorders related to an inflammatory condition, including one or more of the following inflammation related diseases or disorders: allergies, hypersensitivity, autoimmune diabetes, autoimmune liver disease, autoimmune kidney disease, autoimmune gastrointestinal disease, autoimmune skin disease, autoimmune endocrine disease, arthritis, rheumatoid arthritis, asthma, psoriasis, systemic lupus erythematosus, inflammatory bowel syndrome, chronic obstructive respiratory diseases (COPD), fibromyalgia and the neurological diseases and disorders multiple sclerosis, Alzheimer's disease, Parkinson's disease, Huntington's disease, vascular dementia, epilepsy, migraines, stroke and trauma. However, the type of inflammation treatable by the present invention is not limited to those listed here, rather, the present invention contemplates treating any disease or disorder characterized at least in part by inflammation.

One anti-inflammatory agent of the present invention comprises an LTβR-derived peptide, designed to target either or both arms (classical, non-classical) of the LTβR-NFκB signaling pathway. Another anti-inflammatory agent of the present invention comprises a nucleic acid encoding a polypeptide comprising an LTβR-derived peptide. In one embodiment, the invention provides a method for reducing inflammation comprising administering to a subject in need thereof a composition of the invention. In one embodiment, the invention provides a method for preventing inflammation comprising administering to a subject in need thereof a composition of the invention.

In various embodiments, the present invention provides a method for modulating an immune response in a subject. For example, in some embodiments, the method provides for decreasing an immune response by inhibiting effector T cell migration towards a site of an immune response. In some embodiments, the method provides for enhancing an immune response by inhibiting effector T cell migration away from a site of an immune response.

In various embodiments, the present invention provides a method for treating or preventing cancer in a subject. The method is not limited to a particular type of cancer. Exemplary forms of cancer that is treatable by the method of the present invention include, but is not limited to, carcinomas, sarcomas, lymphomas, leukemia, blastomas, and germ cell cancers. For example, the method of the invention can treat or prevent breast cancer, lung cancer, pancreatic cancer, stomach cancer, bone cancer, ovarian cancer, prostate cancer, bladder cancer, cervical cancer, colon cancer, skin cancer, gliomas, esophageal cancer, oral cancer, gallbladder cancer, liver cancer, testicular cancer, uterine cancer, thyroid cancer, throat cancer, and the like.

In various embodiments, the present invention provides a method for treating or preventing contact hypersensitivity in a subject. Certain embodiments include the treatment or reduction of contact hypersensitivity, an inflammatory skin or mucous membrane reaction that results from exposure to sensitizing agents such as allergens (allergic contact hypersensitivity) or irritants (irritant contact hypersensitivity). Photo contact hypersensitivity occurs when the allergen or irritant is activated by sunlight Irritant hypersensitivity relates generally to inflammation that is triggered by contact with acids, alkaline materials such as soaps and detergents, solvents, adhesives, or other chemicals. The skin reaction in irritant contact hypersensitivity usually resembles a burn. Allergic contact hypersensitivity relates generally to inflammation that is triggered by exposure to a variety of different substances, typically a substance or material to which a subject is extra sensitive or allergic. The allergic reaction is often delayed, with the rash or other symptom appearing about 24-48 hours after exposure. The skin reaction in allergic dermatitis typically varies from mild irritation and redness to open sores, depending on the type of irritant, the body part affected, and the sensitivity of the individual. Certain embodiments include the treatment of conditions related to contact hypersensitivity more generally. Examples of such conditions include psoriasis (i.e., a typically chronic, recurrent skin disease in humans marked by discrete macules, papules or patches covered with lamellated silvery scales resulting from an increased turnover of epidermal cells), seborrheic dermatitis, atopic dermatitis (eczema), thermal-induced dermatitis, drug-induced dermatitis, dyshidrotic dermatitis (i.e., a type of eczema that occurs on the palms of the hands, sides of the fingers, and soles of the feet, and typically causes a burning or itching sensation and a blistering rash), urticaria (i.e., a skin condition characterized by welts that itch intensely, caused by an allergic reaction, an infection, or a nervous condition; often called "hives"), and bullous contact hypersensitivity.

The following are non-limiting examples of cancers that can be treated by the disclosed methods and compositions include, but are not limited to, acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocvtoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, wilms tumor.

In some embodiments, the method comprises administering an effective amount of a composition described herein to a subject diagnosed with, suspected of having, or at risk for developing a disease or disorder. In some aspects, the composition is contacted to a cell or tissue where immune cell motility or cancer cell motility is present or at risk for developing. In one embodiment, the composition is administered systemically to the subject.

The composition of the invention may be administered to a patient or subject in need in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of the invention or multiple applications. Administrations may be to single site or to more than one site in the individual to be treated. Multiple administrations may occur essentially at the same time or separated in time.

In some embodiments, the composition of the invention is administered during surgical resection or debulking of a tumor or diseased tissue. For example, in subjects undergoing surgical treatment of diseased tissue or tumor, the composition may be administered to the site in order to further treat the tumor or reduce metastasis.

In one embodiment, the method comprises administering to the subject a composition comprising a LTβR-derived peptide, or a functional fragment thereof.

In another embodiment, the invention provides a method to treat cancer comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compositions of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2 (TIMP-1 and -2). Small molecules, including topoisomerases such as razoxane, a topoisomerase II inhibitor with anti-angiogenic activity, can also be used.

Other anti-cancer agents that can be used in combination with the compositions of the invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

The disclosure provides isolated polypeptides and nucleic acid molecules encoding such sequences. A recombinant polypeptide or a nucleic acid molecule encoding such a polypeptide may be administered to reduce the growth, survival, or proliferation of a tumor or neoplastic cell in a subject in need thereof. In one approach, the polypeptide is administered as a naked polypeptide molecule. In another approach, it is administered in an expression vector suitable for expression in a mammalian cell.

A nucleic acid of the disclosure may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

The nucleic acids may also be administered in combination with a cationic amine such as poly (L-lysine). Nucleic acids may also be conjugated to a chemical moiety, such as transferrin and cholesteryls. In addition, oligonucleotides may be targeted to certain organelles by linking specific chemical groups to the oligonucleotide.

Polynucleotide therapy featuring a nucleic acid molecule encoding a polypeptide is another therapeutic approach for treating or preventing cancer in a subject. Expression vectors encoding the polypeptide can be delivered to cells of a subject for the treatment or prevention of cancer. The nucleic acid molecules must be delivered to the cells of a subject in a form in which they can be taken up and are advantageously expressed so that therapeutically effective levels can be achieved.

Methods for delivery of the nucleic acid molecules to the cell according to the disclosure include using a delivery system, such as liposomes, polymers, microspheres, gene therapy vectors, and naked DNA vectors.

Polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., BACs and YACs). One of skill in the art would be well equipped to construct a vector through standard recombinant techniques, which are described in Sambrook et al., 2012 and Ausubel et al., 2003, both incorporated herein by reference. Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al, Current Eye Research 15:833-844, 1996; Bloomer et al, Journal of Virology 71:6641-6649, 1997; Naldini et al, Science 272: 263-267, 1996; and Miyoshi et al, Proc. Natl. Acad. Sci. U.S.A. 94: 10319, 1997). For example, a nucleotide sequence encoding a polypeptide molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244: 1275-1281, 1989; Eglitis et al, BioTechniques 6:608-614, 1988; Tolstoshev et al, Current Opinion in Biotechnology 1: 55-61, 1990; Sharp, The Lancet 337: 1277-1278, 1991; Cornetta et al, Nucleic Acid Research and Molecular Biology 36:311-322, 1987; Anderson, Science 226:401-409, 1984; Moen, Blood Cells 17:407-416, 1991; Miller et al, Biotechnology 7:980-990, 1989; Le Gal La Salle et al, Science 259:988-990, 1993; and Johnson, Chest 107:77S-83S, 1995). Retroviral vectors are particularly well developed and have been used in clinical settings (Rosenberg et al, N. Engl. J. Med 323:370, 1990; Anderson et al, U.S. Pat. No. 5,399,346).

Other suitable methods for nucleic acid delivery to effect expression of compositions of the present disclosure are believed to include virtually any method by which a nucleic acid (e.g., DNA, including viral and nonviral vectors) can be introduced into an organelle, a cell, a tissue or an organism, as described herein or as would be known to one of ordinary skill in the art.

The administration of a nucleic acid or peptide inhibitor of the invention to the subject may be accomplished using gene therapy. Gene therapy, which is based on inserting a therapeutic gene into a cell by means of an ex vivo or an in vivo technique. Suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO94/29469; WO97/00957 or Schaper, Current Opinion in Biotechnology 7 (1996), 635-640 and the references quoted therein. The polynucleotide encoding the polypeptide of the invention can be designed for direct insertion or by insertion through liposomes or viral vectors (for example, adenoviral or retroviral vectors) in the cell. In one embodiment the cell is a cell of the germinal line, an embryonic cell or egg cell or derived from the same, or the cell is a core cell. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sci. USA, 88 (1991), 2726-2729). The standard methods for transfecting cells with recombining DNA are well known by an expert on the subject of molecular biology, see, for example, WO94/29469; see also supra. Genetic therapy can be carried out by directly administering the recombining DNA molecule or the vector of the invention to a patient or transfecting the cells with the polynucleotide or the vector of the invention ex vivo and administering the transfected cells to the patient. Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Polypeptide expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to direct gene expression in specific cell types can be used to direct the expression of a nucleic acid. The enhancers used can include, without limitation, those that are characterized as tissue- or cell-specific enhancers. For any particular subject, the specific dosage regimes should be adjusted over time according to the individual need and the professional judgment of the person administering or supervising the administration of the compositions.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are administered by i.v. injection.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1

Stimulation of the Afferent LEC LTβR Preferentially Engages the NIK Pathway, Resulting in Changes in LEC Morphology, Structure, and Gene Expression, for Promoting Graft Tolerance and Reducing Inflammation Experiments described herein were conducted using LTβR-specific cell permeable peptides targeted to the separate arms of the NF-κB pathway to reveal the molecular mechanisms of Treg migration, with an aim to develop therapeutic peptides to promote graft tolerance by avoiding unwanted immune responses. The results showed that stimulation of the afferent lymphatic endothelial cell (LEC) LTβR preferentially engages the NIK pathway, resulting in changes in LEC morphology, structure, and gene expression. These changes couple with T cell ligands and receptors to determine trans-endothelial migration (TEM) into the afferent lymphatics.

The materials and methods employed in these experiments are now described.

Animals and Cells

C57BL/6 (WT, Ltα$^{-/-}$) (7-10 weeks) were purchased from The Jackson Laboratory (Bar Harbor, Me.). Foxp3GFP (Fontenot, J. D. et al., 2005, Immunity, 22:329-341) mice on a C57BL/6 background were obtained. C57BL/6 mouse primary dermal LECs (C57-6064 L) were from Cell Biologics, Inc. (Chicago, Ill.), and were cultured according to the manufacturer's instructions in manufacturer-provided mouse endothelial cell medium supplemented with 5% FBS, 2 mM L-glutamine, 100 IU/mL penicillin, vascular endothelial growth factor, endothelial cell growth supplement, heparin, epidermal growth factor, and hydrocortisone. SVEC4-10 (CRL-2181) cells were from American Type Culture Collection, and were cultured in DMEM with 4.5 g/L glucose, containing 10% (v/v) FBS, 2 mM L-glutamine, 100 IU/mL penicillin and 100 µg/mL streptomycin.

Peptide Synthesis and Reconstitution

Peptides were synthesized by GenScript. All peptides were >95% purity, dissolved in endotoxin-free ultrapure water, and concentrations quantified by spectrophotometry (Pace, C. N. et al., 1995, Protein Sci., 4:2411-2423) after reconstitution and stored at −80° C.

Antibodies and Reagents

NF-κB2 p100/p52, NIK, phospho-IKKα/β (Ser176/180) (16A6). IκBα, TRAF2, TRAF3, and GAPDH antibodies were from Cell Signaling Technology, Inc. (Danvers, Mass.). Agonistic anti-mouse LTβR mAb (clone 3C8), functional grade anti-mouse VCAM-1 (429), anti-mouse integrin β1 (HMb1-1), and anti-mouse CD103 (integrin αE, 2E7) were from eBioscience (San Diego, Calif.). Anti-mouse LTβR (5G11b) LEAF™ purified anti-mouse integrin (16 (GoH3), LEAF™ purified anti-mouse integrin β7 (FIB27), and anti-mouse integrin β4 (346-11A) were from Biolegend (San Diego, Calif.). Azide and endotoxin were further removed from anti-mouse integrin β4 by gel filtration and Pierce™ High Capacity Endotoxin Removal Resin (ThermoFisher, Halethorp, Md.). BAY-11-7082 was from Sigma-Aldrich (St. Louis, Mo.) and anti-NIK (A-12) from Santa Cruz Biotechnologies (Dallas, Tex.). NIK inhibitor NIKi was from Enamine LLC (Monmouth Jct, N.J.). cIAP1/2 inhibitor AT406 was from Selleckchem (Houston, Tex.). LTβRIg was a gift from Biogen Idec (Durham, N.C.). Rat IgG1 (MOPC21) was from BioExCell (West Lebanon, N.H.). Carboxyfluorescein succinimidyl ester (CFSE) was from Invitrogen (Waltham, Mass.)

Mouse CD4$^+$ T Cell Purification and Culture

CD4$^+$ T cells from mouse LNs and spleens were isolated using CD4$^+$ negative selection (Stemcell Technologies, Cambridge, Mass.), and were cultured as previously described (Butcher, E. C. et al., 1996, Science, 272:60-66). Briefly CD4$^+$ CD44loCD25$^-$Foxp3GFP$^-$WT or Ltα$^{-/-}$ cells with >98% purity were sorted using a FACS Aria II (BD Biosciences). The sorted GFP$^-$ T cells (5×10$^4$) were then co-cultured with T cell-depleted, 800 rad-irradiated C57BL/6 splenocytes as stimulator cells (5×10$^4$) in U-bottom 96-well plates for 5 days at 37° C. in 5% CO$_2$, with IL-2 (20 ng/mL, eBioscience), anti-CD3c mAb (1 µg/mL, clone 145-2C11, eBioscience) for effector T cells (Teff); and human TGF-β1 (10 ng/mL, eBioscience) for induced regulatory T cells (iTreg). Cells were cultured in RPMI 1640 supplemented with 10% FBS, 1 mM sodium pyruvate, 2 mM L-glutamine, 100 IU/mL penicillin, 100 µg/mL streptomycin, non-essential amino acids and 2×10$^{-5}$M 2-ME (Sigma-Aldrich).

Flow Cytometry

LECs in PBS containing 0.2 mM calcium, 0.1 mM magnesium and 0.5% w/v BSA were treated with anti-CD16/32 (clone 93, eBioscience) to block Fc receptors, and then stained with antibodies to cell surface molecules in the same buffer. Flow cytometry antibodies used were: APC-eflour780-anti-mouse CD4 (GK1.5, eBioscience); PE-anti-mouse CD25 (PC61.5, eBioscience); APC-anti-mouse VCAM-1 (clone 647, eBioscience). For detection of LTα2β1, T cells were incubated with MOPC21 or LTβRIg at 2 µg/mL for 60 minutes at 37° C. in HBSS with 2% FBS. Cells were washed, and then stained for 45 minutes at 4° C. with BV421-rat anti-mouse IgG1 along with antibodies to other cell surface markers. Cells were then washed and fixed with 4% paraformaldehyde and run on an LSR Fortessa flow cytometer (BD Biosciences, San Jose, Calif.). Results were analyzed with software FlowJo 8.7 (Treestar).

MTT Viability Assay

LECs were plated into 24-well tissue culture plates, incubated overnight, and treated with 20 µM peptides with or without agonist anti-LTβR (2 µg/mL) for 4 hours, followed by 3 hour incubation with 0.5 mg/mL MTT (3-(4, 5-Dimethylthiazol-2-yl)-2, 5 diphenyl tetrazolium bromide) (Sigma-Aldrich). 50 µL DMSO was added to cells before reading OD at 540 nm.

Evans Blue Endothelial Permeability Assay 2.5×10$^5$ primary LEC or SVEC4-10 were plated on inverted 0.2% (w/v) gelatin-coated Boyden chamber transwell polycarbonate membranes. The cell layers were treated with various conditions as noted prior to adding 100 µL of 0.67 mg/mL Evans Blue (Sigma-Aldrich) diluted in IMDM migration medium containing fat-free BSA (40 mg/mL) (Gemini Bio-Products, Broderick, Calif.). 600 µL fresh migration medium without phenol red was added to the lower chamber. After 0.5, 1, 2, and 3 hours, lower chamber medium was collected into flat-bottom 96-well tissue culture (TC) plate, and the optical density at 650 nm was measured in a microplate reader (TECAN, San Jose, Calif.).

T Cell-LEC Binding Assay

2×10$^4$ primary LECs or SVEC4-10 were plated on 0.2% (w/v) gelatin-coated flat-bottom 96-well TC plate. The LEC layers were treated with peptides or antibodies as noted before adding with 2×10$^5$ CF SE-labelled CD4 T cells in IMDM migration buffer without phenol red indicator. After 3 hours at 37° C. in 5% $CO_2$, non-bound cells were removed by gently washing and replacing with PBS containing 0.1 mM $MgCl_2$ and $CaCl_2$. Control wells with input CFSE-CD4 T cells remain unwashed. The fluorescein intensity (FI) from the bound CFSE-CD4 T cells in the plate was measured with a microplate reader. Percentage of bound CFSE-CD4 T cells were calculated as 100×X (FI of sample-FI of plate/cell background)/FI of input CFSE-CD4 T cells.

Real-Time PCR and Microarrays

One μg of total RNA extracted using Trizol reagent (Invitrogen) was reverse-transcribed into cDNA with GoScript™ Reverse Transcription System (Promega, Fitchburg, Wis.). mRNA expression levels were quantified by real-time PCR using SYBR Green Master Mix with an ABI Prism 7900HT (Applied Biosystems, Foster City, Calif.). Values for specific gene expression were normalized to housekeeping HPRT gene expression and were calculated as: $2^{(Ct\ of\ HPRT-Ct\ specific\ gene)}$. For the microarrays, total RNA of treated mLECs was extracted with RNeasy mini kit (Qiagen, Germantown, Md.) and analyzed for purity and integrity by capillary electrophoresis on an Agilent Bioanalyzer 2100 (Agilent Technologies, Inc. Santa Clara, Calif.). 100 ng/sample was subjected to amplification, followed by labeling and hybridization to Mouse Genome 430 2.0 GeneChips (Affymetrix, Santa Clara, Calif.). Sample amplification, labeling, hybridization, and detection were performed according to the manufacturer's protocols.

ELISA $5\times10^5$ LECs or SVEC4-10 cells were plated in 12-well plates and treated with 20 μM peptides for 30 minutes at 37° C. Cells were then washed and incubated with anti-LTβR agonistic mAb (2 μg/mL) for 30 minutes at 4° C., followed by washing and then cross-linking with anti-rat IgG (2 μg/mL) for 6 or 16 hours at 37° C. The supernatants were collected and stored in −80° C. Mouse CCL2 and CCL21 were measured with ELISA kits from Biolegend, Inc. and R&D Systems (Minneapolis, Minn.), respectively.

Immunoblotting and Co-Immunoprecipitation

LECs were lysed in buffer containing 20 mM HEPES (pH 7.4), 150 mM NaCl, 10 mM NaF, 2 mM $Na_3VO_4$, 1 mM EDTA, 1 mM EGTA, 0.5% Triton X-100, 0.1 mM DTT, 1 mM PMSF and protease inhibitor cocktail (Roche, Indianapolis, Ind.). Protein in the cell extract was quantified using protein quantification kit (Bio-Rad, Philadelphia, Pa.) and 10 μg total protein was run on Novex™ WedgeWell™ 4-20% Tris-Glycine Mini Gels (Invitrogen) and transferred to an Immobilon-P membrane (Bio-Rad). Membranes were probed with anti-NF-κB2 p100/p52, NIK, phospho-IKKα/β(Ser176/180) (16A6), IκBα, TRAF2, TRAF3, and GAPDH antibodies. For co-IP assays, 500 μg total protein of cell extract was incubated with 1 μg of anti-mLTβR (5G11b) overnight, followed by 4 hour incubation with 25 μL protein G Agarose beads (Sigma-Aldrich). The beads were then washed with lysis buffer and boiled in 2× Laemmli sample buffer (Bio-Rad).

Transendothelial Migration

Transmigrations across endothelial cells were described previously (Brinkman, C. C. et al., 2016, Nat Commun, 7:12021). Briefly the inverted transwell insert (24-well, Corning International) with 5 μm pore size was coated with 0.2% (w/v) gelatin (Bio-Rad) for 1 hour at 37° C. before loading with $1.5\times10^5$ primary skin LEC or SVEC4-10 in 100 μL mLEC or cDMEM medium. After 2 days, the LEC cell layers were treated with various conditions as noted in the text and figure legends prior to adding $2\times10^5$ T cells in 100 μL to the upper chamber of transwell plate while the lower chamber contained mCCL19 (50 ng/mL, R&D systems). All cells or reagents were prepared in IMDM containing transferrin and 0.5% (w/v) fatty acid-free BSA (Gemini). T cells that migrated to the lower chamber after 3 hours at 37° C. were counted.

Time-Lapse Microscopy

Purified naïve CD4 T cells were incubated with 5 μM CFSE at 37° C. for 5 minutes, quenched with 50% FBS at 4° C. for 5 minutes and were washed in migration buffer. CFSE-labelled CD4 T cells ($5\times10^4$ cells per transwell) migrating across endothelial monolayers to CCL19 (50 ng/mL) were visualized by EVOS FL Auto Cell Imaging System (Thermo Fisher Scientific) with a ×20 objective. One image was captured every 5 minutes for 3 hours. Cell tracks were analyzed with Volocity version 6.3 software (Perkin Elmer).

Immunohistochemistry

LEC monolayers were stained for surface VCAM-1, LTβR or Lyve-1 with rat anti-mouse VCAM-1 (Clone 429, eBioscience), rat anti-mouse LTβR (Clone 3C8, eBioscience) or rabbit anti-mouse Lyve-1 (70R-LR003, Fitzgerald, Acton, Mass.), then were fixed for 20 minutes at 4° C. with 4% (w/v) paraformaldehyde (Affymetrix), permeabilized with PBS 0.2% (v/v) Triton X-100 (Sigma-Aldrich), and treated with 2% donkey serum for 10 minutes then incubated with rabbit anti-mouse CXCL12 (eBioscience), goat-anti-mouse CCL21 (Clone AF457, R&D System), or anti-NIK mouse monoclonal antibody (Clone A-12, Santa Cruz Biotechnology) overnight at 4° C. The primary antibodies were detected with Alexa Fluor 448, 647 (Cy5), or 546 (Cy3)-conjugated donkey anti-goat, donkey anti-rabbit, or donkey anti-rat secondary antibodies (Jackson ImmunoResearch, West Grove, Pa.) for 1 hour at 4° C. Transwell membranes were transferred onto glass slides and visualized by fluorescent microscopy (Zeiss LSM 510 Meta, and LSMS Duo) with a ×60 or ×20 objective. Images were analyzed with Volocity version 6.3 software.

Footpad and Whole-Mount Ear Migration Assays

Mice were anaesthetized and $1\times10^6$ $CD25^+$ Tregs or $CD4^+$ non-Tregs were injected intradermally into the footpads or ear pinnae in 20 μL PBS as previously described (Brinkman, C.C., et al. 2016, Nat Commun, 7:12021). For footpad assays, draining popliteal LN were collected 12 hours post injection and processed for flow cytometry. For ear pinnae assays, whole-mount ears were collected 4 hours post injection, fixed for 10 minutes at room temperature with 4% paraformaldehyde, then stained with anti-Lyve-1 at 5 mL (70R-LR003, Fitzgerald), anti-CCL21 (AF457, R&D Systems) at 5 μg/mL in PBS, 0.5% BSA, and 0.3% Triton X-100 overnight at 4° C.; washed with PBS, 0.5% BSA, and 0.3% Triton X-100; stained with 5 mL donkey anti-rabbit Alexa Fluor 488 and donkey anti-goat Cy3 (Jackson ImmunoResearch) for 2 hours at 4° C., washed twice in PBS, 0.5% BSA, and 0.3% Triton X-100; fixed once more as above, transferred to glass slides, and mounted with Prolong Gold (Life Technologies, Carlsbad, Calif.). Distance of T cells from lymphatic vessels calculated with minimum distance program in Volocity 6.3.

Statistical Analysis

Numerical data presented as means+/−SEM. Significance of differences evaluated using 1 way ANOVA and Prism 5 software. Asterisks mark data statistically different from the controls, with p-values noted. Number of replicates noted.

The results of the experiments are now described.

Figure 1A:
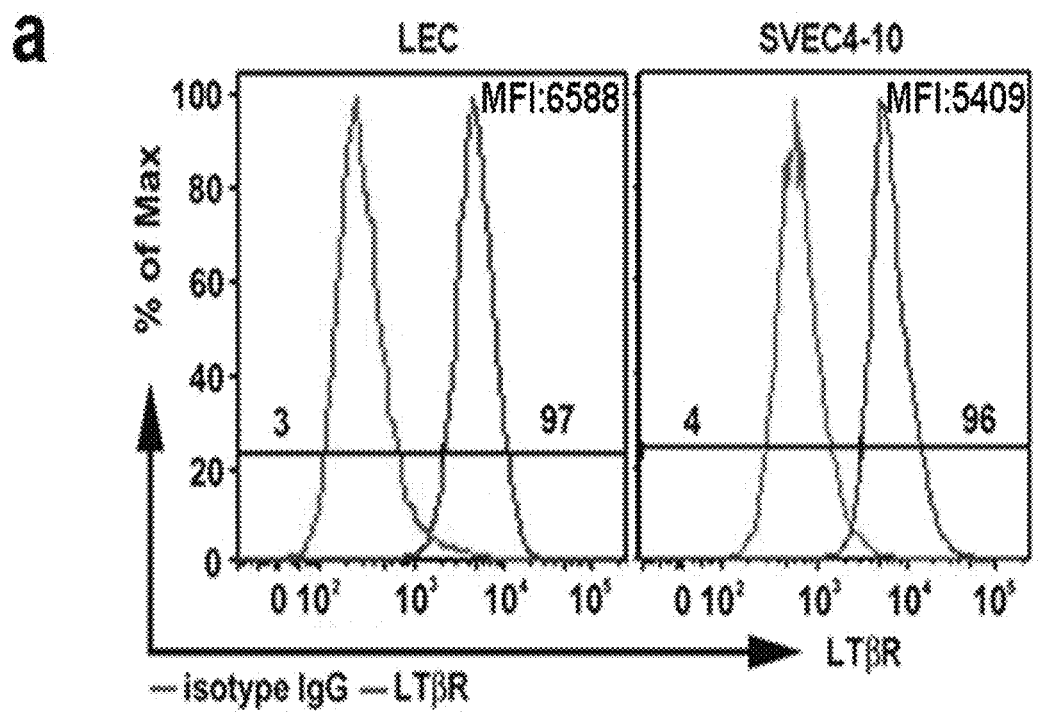
FIG. 1A through FIG. 1F, depicts the results of example experiments demonstrating that non-classical NF-κB signaling is preferentially induced by LTβR activation in lymphocyte endothelial cells (LEC).
Figure 1B:
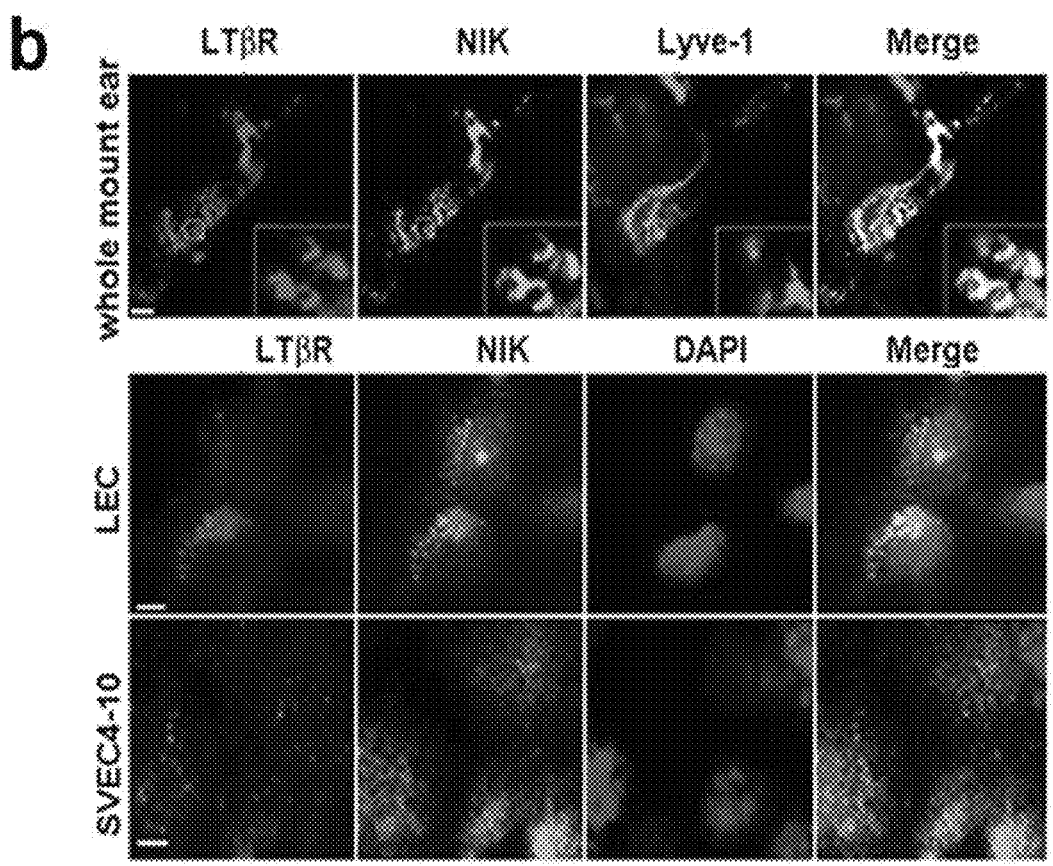
Figures 1C, 1D:
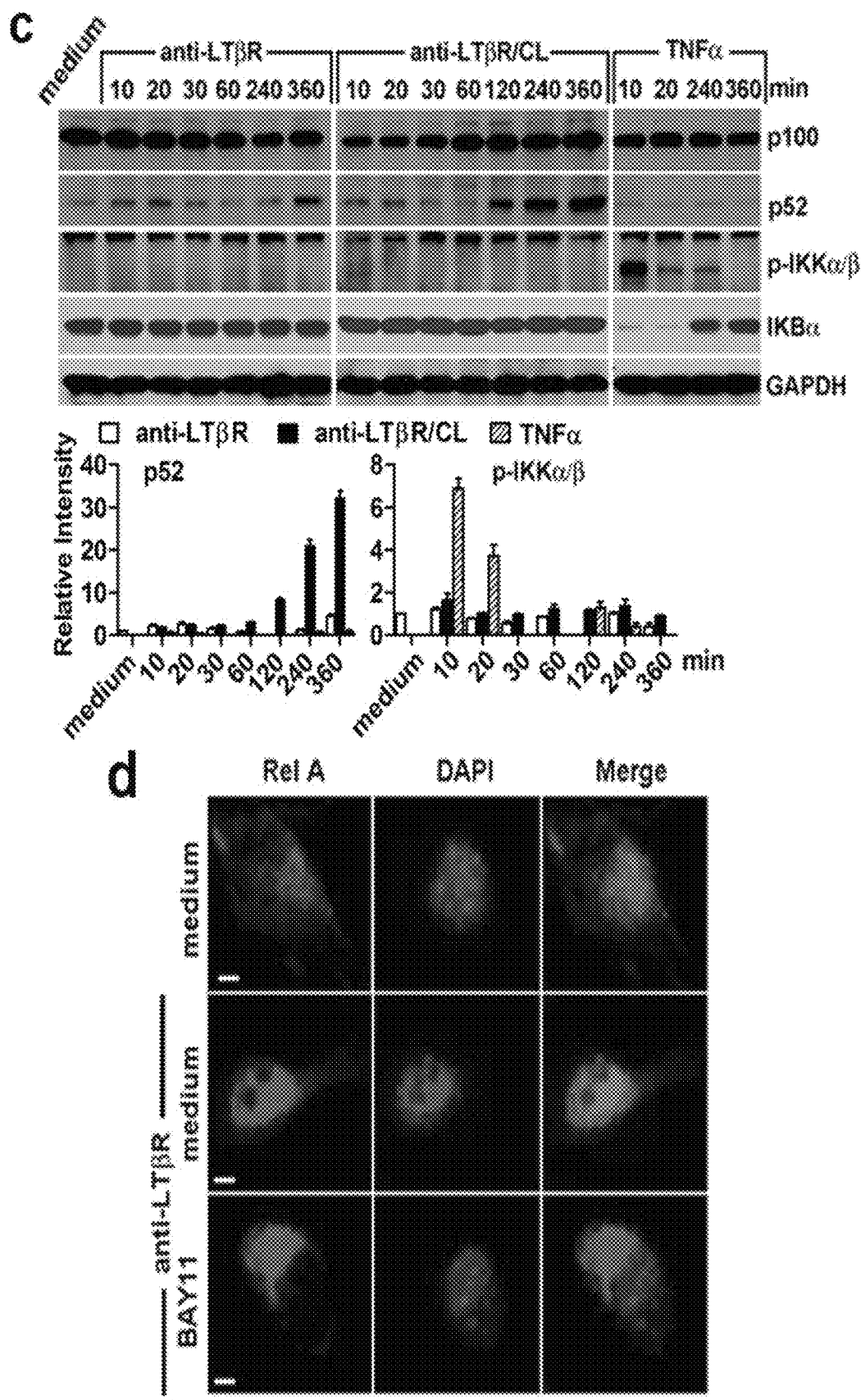
Figures 1E, 1F:
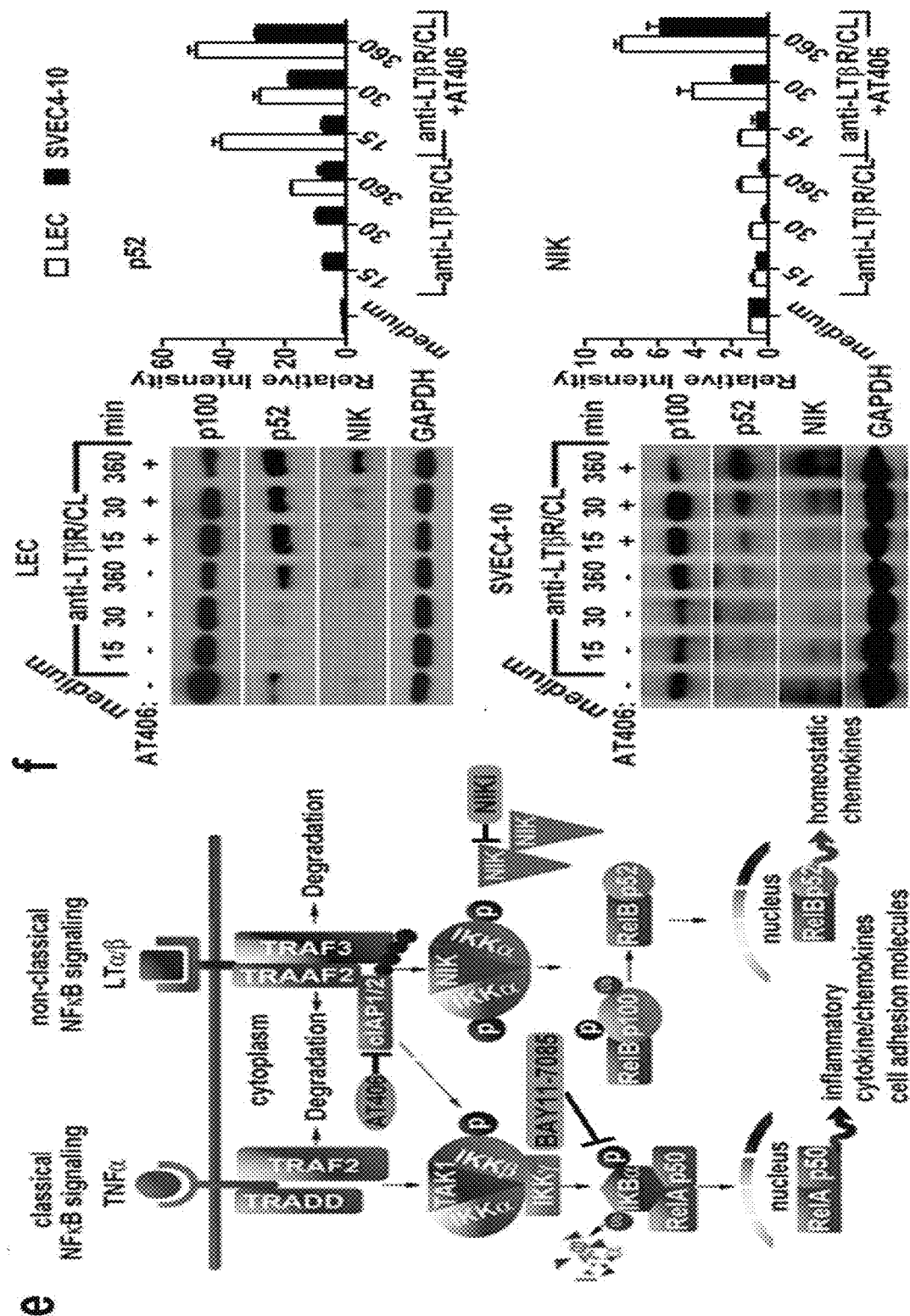

LTβR Mediates Predominantly Non-Classical NFκB Signaling In Murine Lymphatic Endothelial Cells Flow cytometry, immunohistochemistry, and western blot analysis of murine primary LEC, the SVEC4-10 LEC line, and lymphatic vessels in vivo confirmed that LEC express high levels of the LTβR (FIG. 1A, FIG. 1B, and FIG. 3B). LTβR reportedly activates the early classical NFκB pathway followed by the alternative pathway in certain cells (Muller, J. R. et al., 2003, J Biol Chem., 278:12006-12012). However, in LEC early classical NFκB activation induced by an anti-LTβR agonist mAb, such as phosphorylation of IKKα/β or NFκBα degradation, was weak or absent. In contrast, TNFα induced strong IKKα/β phosphorylation and IκBα degradation in the same cells (FIG. 1C), showing that classical NFκB signaling was intact.

LTβR activation has also been reported to proceed preferentially through the non-classical NFκB, or NIK pathway (Basak, S. et al., 2007, Cell, 128:369-381) (FIG. 1E). Indeed, LTβR activation in LEC induced strong NIK signaling as noted by increased p100 processing into p52, and p100 processing was further promoted by cross-linking the agonist antibody (anti-LTβR/CL) (FIG. 1C). NIK signaling in response to LTβR stimulation was also noted in the SVEC4-10 LEC line (FIG. 1F). AT406, an inhibitor of cIAP1/2, the E3 ubiquitin ligase which targets NIK for proteasome-mediated degradation in resting cells, promoted more LTβR-mediated NIK accumulation and p100 processing in LEC and SVEC4-10 (FIG. 1F), further confirming the activation of the NIK signaling pathway by LTβR activation. It was noteworthy that NIK expression was observed in resting primary LEC and SVEC4-10 and in Lyve-1 expressing LEC of mouse ear pinnae in vivo (FIG. 1B), and at baseline there were low levels of p52 present in the LEC and SVEC4-10 (FIG. 1C, FIG. 1F). Furthermore, both LTβR and NIK co-localized in LEC confocal images (FIG. 1B). Together these data suggested that there was low-level constitutive activation of the non-classical pathway in LEC both in vivo and in vitro, and preferential use of the non-classical pathway by LTβR signaling.

Figures 2A, 2B:
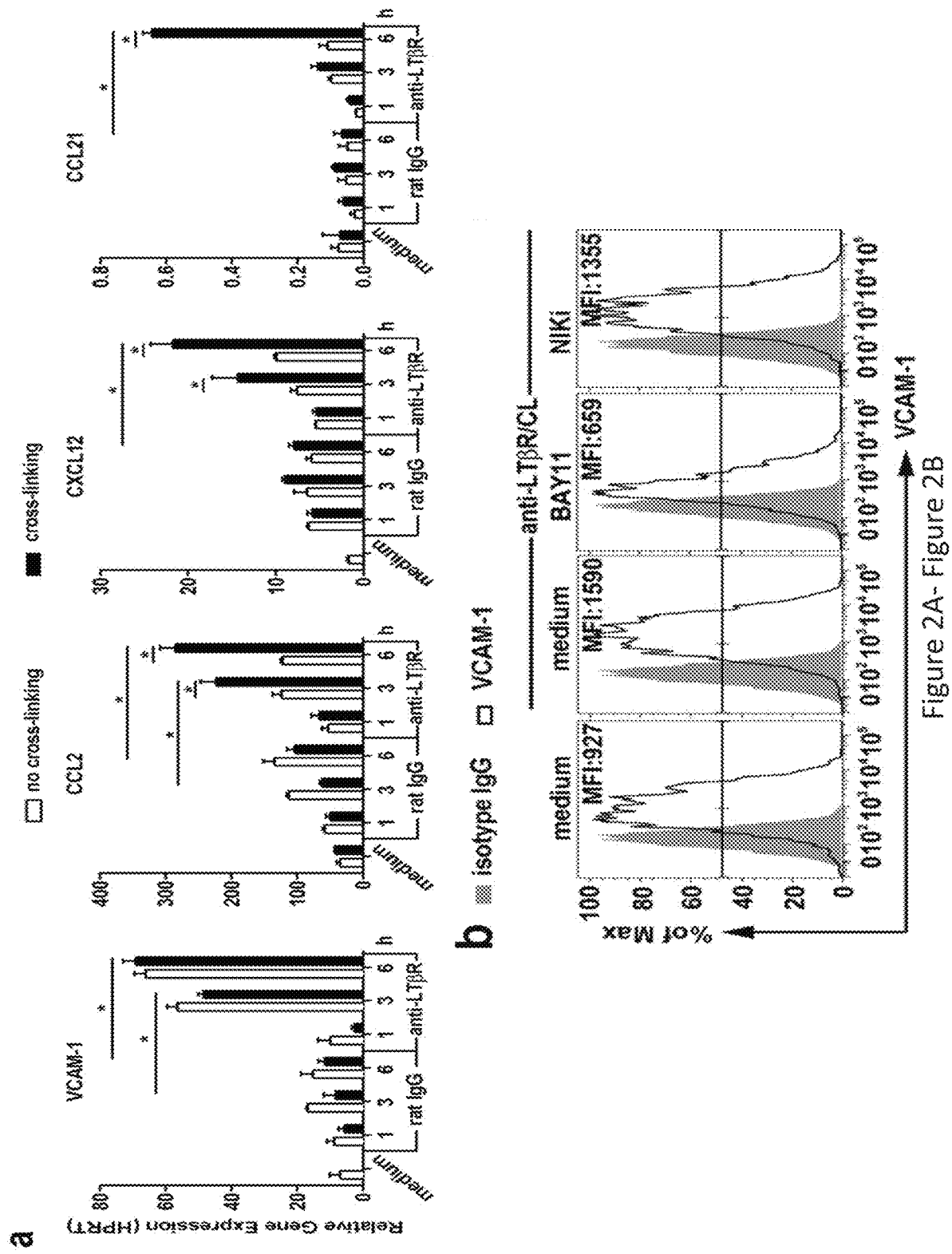
FIG. 2A through FIG. 2D, depicts the results of example experiments demonstrating that agonistic anti-LTβR mAb induces inflammatory and homeostatic chemokines and cell adhesion molecules in LEC.
Figures 2C, 2D:
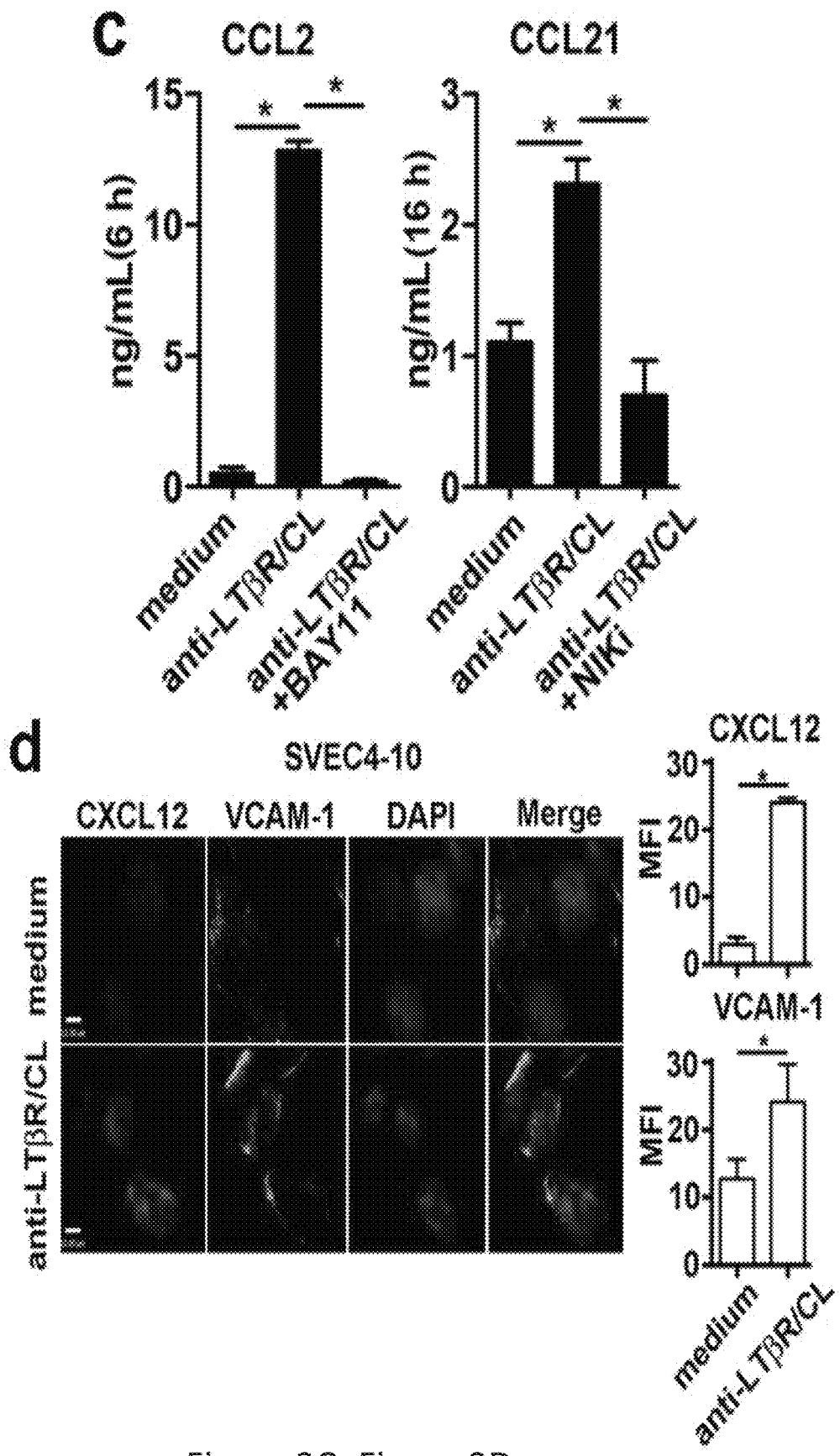

LTβR Stimulation Induces Chemokines and Cell Adhesion Molecules In LEC By Classical and Non-Classical Pathways LTβR stimulation induces classical NFκB-dependent genes, such as the inflammatory chemokines CCL4 and CXCL2, and the adhesion molecule VCAM-1 in diverse cell types (Madge, L. A. et al., 2008, J Immunol., 180:3467-3477). LTβR stimulation also induces non-classical NIK-dependent genes, including the homeostatic chemokines CCL19, CCL21, and CXCL12 (Dejardin, E. et al., 2002, Immunity, 17:525-535; Madge, L. A. et al., 2008, J Immunol., 180:3467-3477; Schneider, K. et al., 2004, Immunol Rev., 202:49-66). LTβR ligation on LECs induced VCAM-1 and the inflammatory chemokine CCL2 transcription as early as 3 hours after stimulation (FIG. 2A), along with increasing cell surface VCAM-1 (FIG. 2B, FIG. 2D) and CCL2 secretion (FIG. 2C). Cross-linking anti-LTβR mAb on the cell surface to potentiate receptor signaling further enhanced CCL2 transcription (FIG. 2A). LTβR-mediated CCL2 production and VCAM-1 expression were suppressed by BAY11-7085, an irreversible inhibitor of IκBα phosphorylation. (FIG. 2B, FIG. 2C). In contrast, the NIK inhibitor 4H-isoquinoline-1,3-dione (NIKi) did not affect VCAM-1 expression on LEC. These results confirm the dependence of the expression of these molecules on the classical NFκB pathway.

The transcription of the homeostatic chemokines CXCL12 and CCL21 gradually peaked 6 hours after strong LTβR stimulation induced by cross-linking the agonist mAb (FIG. 2A). Increased CCL21 secretion in culture was detectable after 16 hours (FIG. 2C). Increased intracellular expression of CXCL12 could also be demonstrated after stimulation (FIG. 2A, FIG. 2D). CCL21 transcription and production induced by LTβR activation were inhibited by the NIKi (FIG. 2C), confirming the non-classical pathway dependence of the expression of these genes. Together these results showed that LTβR stimulation on LEC resulted in the earlier expression of genes regulated by the classical NFκB pathway followed by the later expression of genes regulated by the non-classical NIK pathway.

Figure 8:
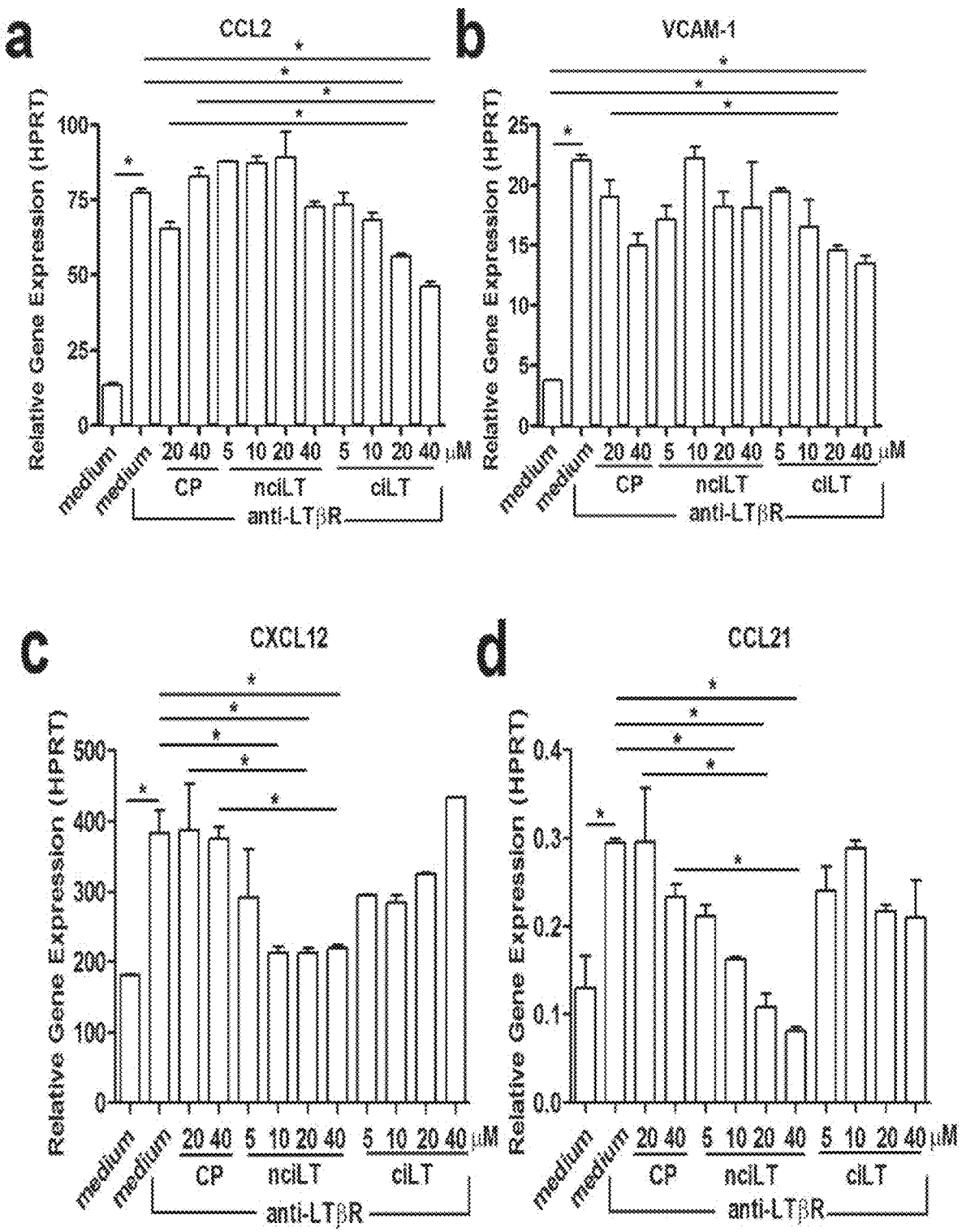
FIG. 8, comprising

Design and Evaluation of LTβR-Derived Peptides That Target Separate NFκB Pathways LTβR recruits TNF receptor-associated factors (TRAFs) 2, 3, and 5 via its intracellular domain. Mutagenesis studies indicate that TRAF binding to specific motifs in LTβR bifurcates the two arms of NFκB signaling (FIG. 3A) (Ganeff, C. et al., 2011, Mol Cell Biol., 31:4319-4334; Force, W. R. et al., 2000, J Biol Chem., 275:11121-11129). Decoy peptides comprised of the N-terminal cell-penetrating sequence of the Drosophila antennapedia peptide (RQIKIWFQNRRMKWKK; SEQ ID NO:1) plus one of the TRAF-binding motifs in LTβR were designed to specifically target the separate arms of the NFκB pathway (TGNIYIYNGPVL; SEQ ID NO:2, and PEEGAPGP; SEQ ID NO:3) (FIG. 3A). nciLT (RQIKIWFQNRRMKWKKTGNIYIYNGPVL; SEQ ID NO:4) harbored the sequence required for TRAF3 recruitment into the activated, non-classical LTβR complex and p100 processing (Ganeff, C. et al., 2011, Mol Cell Biol., 31:4319-4334). ciLT (RQIKIWFQNRRMKWKKPEEGAPGP; SEQ ID NO:5) included the (P/S/A/T)X(Q/E)E TRAF-binding motif required for TRAF2 and TRAF3 binding to LTβR in the classical pathway (Ganeff, C. et al., 2011, Mol Cell Biol., 31:4319-4334; Ye, H. et al., 1999, Mol Cell., 4:321-330). The effective doses and incubation periods for the peptides were determined by cytokine responses of SVEC4-10 activated with anti-LTβR mAb and treated with various doses of nciLT and ciLT (FIG. 8C). The results showed that 20 μM of each peptide gave optimal results, similar to previous experience with peptides of different specificities (Piao, W. et al., 2015, Cell Rep., 11:1941-1952; Piao, W. et al., 2013, Proc Natl Acad Sci USA., 110:19036-19041).

To evaluate their blocking activities in signaling responses, LEC were incubated with these blocking peptides prior to activation with anti-LTβR mAb, and compared to conventional, receptor nonselective inhibitors of the separate NFκB signaling pathways. With respect to classical signaling in LEC and SVEC4-10 cells, TRAF3 constitutively bound to the LTβR, and LTβR activation induced rapid TRAF2 recruitment to the receptor after 10 minutes (FIG. 3B) followed by later TRAF2 degradation after 6 hours (FIG. 3E). Immunoprecipitation showed that ciLT but not BAY11-7085 was sufficient to inhibit both TRAF2 and TRAF3 recruitment to the LTβR complex (FIG. 3B). ciLT but not BAY11-7085 also prevented TRAF2 degradation (FIG. 3E). These results indicated that ciLT acted as an inhibitor of the LTβR upstream classical NFκB pathway, while BAY11-7085 acted as a post-receptor/TRAF complex downstream classical NFκB inhibitor. In keeping with the low level of classical NFκB activities by the LTβR (FIG. 1C); there was no observed LTβR-induced rapid phosphorylation of IKKα/β or IκB, or IκB degradation in LEC and SVEC4-10 (FIG. 3C). Nonetheless, early response genes of the classical pathway (CCL2, VCAM-1) were induced by LTβR activation and their expression specifically inhibited by ciLT (FIG. 3D and FIG. 8C).

With respect to the non-classical pathway, activation of LTβR in LEC and SVEC4-10 induced rapid and strong NIK accumulation after 10 minutes followed by p100 processing to p52 (FIG. 3E). Notably, there was TRAF3 binding to LTβR in unstimulated LECs (FIG. 3B) suggesting, as noted above (FIG. 1B, FIG. 1C, FIG. 1E), low level constitutive activation of the non-classical pathway via the LTβR. Immunoprecipitation showed that nciLT blocked TRAF3 but not TRAF2 binding to the LTβR complex (FIG. 3B) and prevented p100 processing to p52 (FIG. 3E). In comparison, NIKi blocked both TRAF2 and TRAF3 recruitment to the receptor, prevented downstream p100 processing to p52, and inhibited TRAF2 degradation. These results showed that nciLT specifically sequestered TRAF3 from the receptor complex, and did not prevent TRAF2 degradation, but did prevent NIK accumulation for non-classical NFκB signaling. In contrast, NIKi prevented TRAF2 degradation, which is required for classical NFκB activation, suggesting nciLT was a more specific NIK pathway inhibitor than NIKi. In fact, NIKi had a partial inhibitory effect on CCL2 transcription activated by the classical pathway (FIG. 27). Late response genes of the non-classical pathway (CCL21, CXCL12) were induced by LTβR activation and their expression specifically inhibited by nciLT (FIG. 8C).

Figures 3F, 3G:
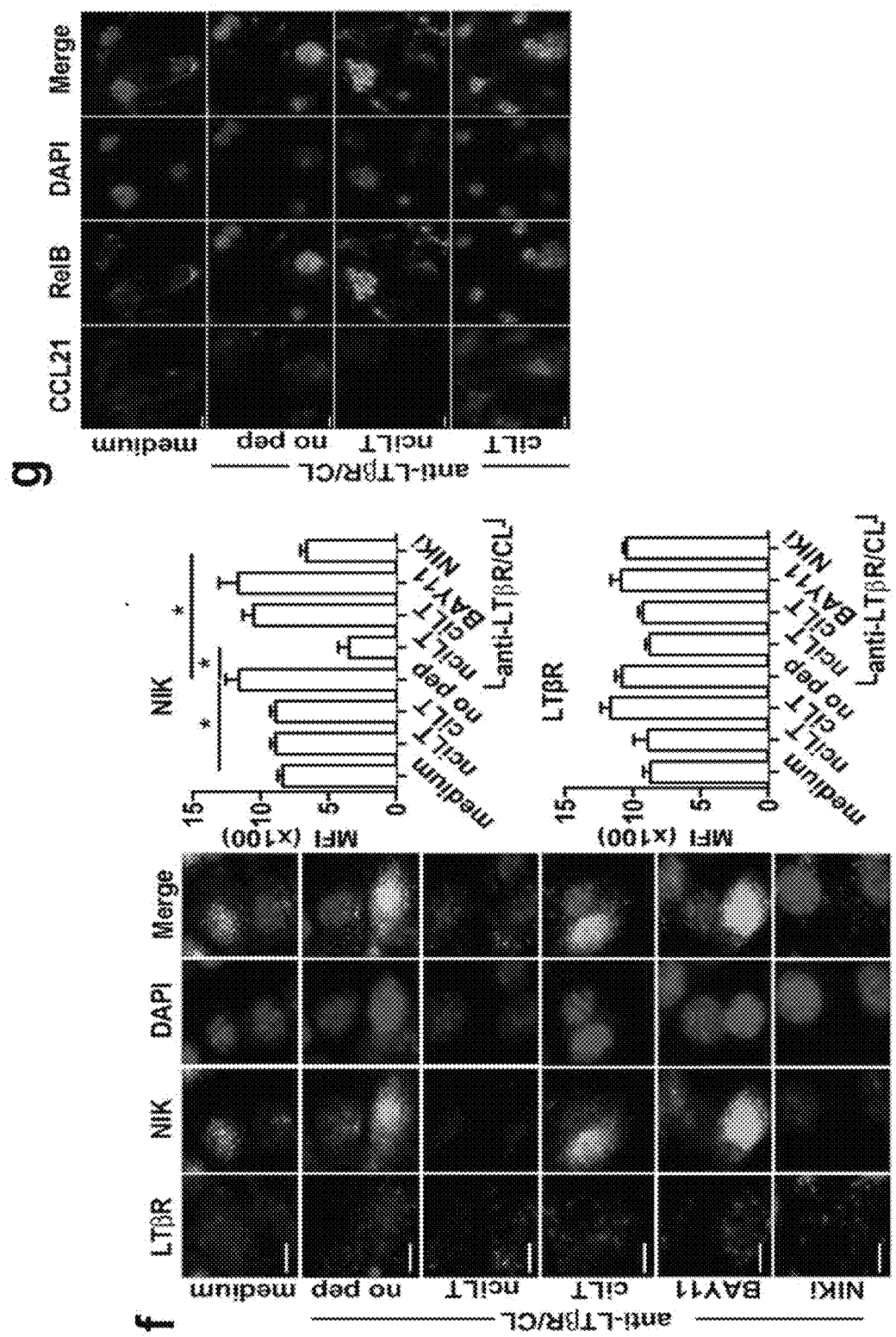

Immunohistochemistry showed co-expression of LTβR and NIK on LEC and SVEC4-10, with co-localization of the two molecules in confocal images (FIG. 1B, FIG. 3F). nciLT inhibited NIK expression and its co-localization with LTβR, without affecting LTβR expression (FIG. 3F). In contrast, neither ciLT, BAY11-7085, nor NIKi affected NIK expression or co-localization with LTβR. In addition, LTβR activation induced RelB nuclear translocation which was suppressed by nciLT but not ciLT (FIG. 3G). Together, these data confirmed the specificity and mechanism of activity of nciLT in comparison to the other molecules.

Differential Gene Profiles Are Regulated By The LTβR-NFκB Blocking Peptides

Figure 4D:
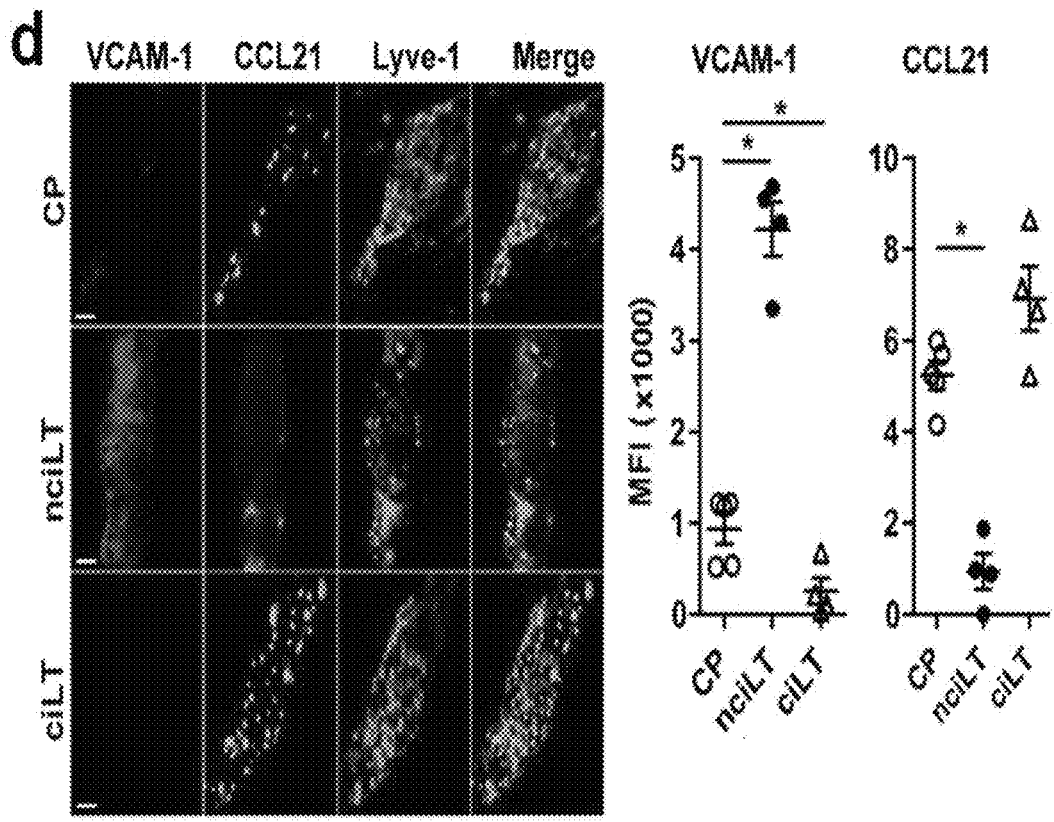
Figures 4E, 4F, 4G:
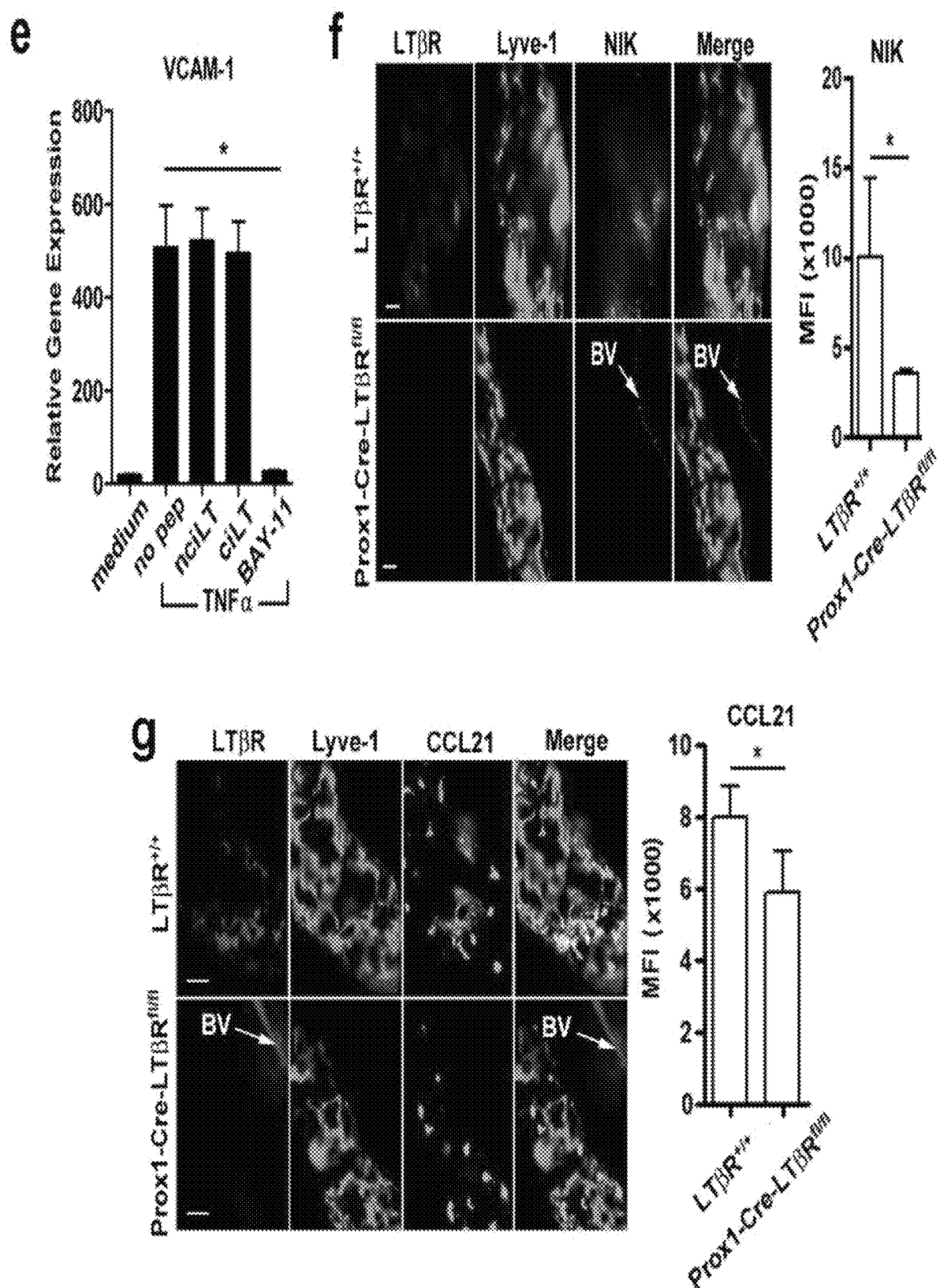

To further validate the peptide inhibitor specificities and mechanisms, their actions were related to the separate LTβR signaling pathways and specific gene activation. The blocking peptides were assessed for their effects on early classical pathway and later non-classical pathway gene activation and expression in LEC. nciLT, which blocked LTβR-non-classical NFκB signaling, enhanced early classical pathway CCL2 and VCAM-1 expression and inhibited homeostatic CXCL12, CCL19, and CCL21 chemokine production via the non-classical pathway, as measured by RT-PCR (FIG. 4A), ELISA (FIG. 4B), and immunohistochemistry (FIG. 4C). nciLT was also effective in vivo and significantly decreased the expression of CCL21 on Lyve-1+lymphatic vessels (FIG. 4D). Conversely, ciLT blockade of the LTβR-classical NFκB pathway suppressed classical pathway induced CCL2 and VCAM-1 and enhanced non-classical homeostatic chemokines CXCL12, CCL19, and CCL21 (FIG. 4A, FIG. 4B, FIG. 4C, and FIG. 4D). In vivo, ciLT significantly enhanced expression of CCL21 on Lyve-1+ lymphatics. Both peptides showed LTβR-specific inhibition since TNFR1-mediated VCAM-1 expression was not affected by either nciLT or ciLT, yet was significantly inhibited by BAY11-7085 (FIG. 4E). Thus, these peptides specifically inhibited gene expression regulated by the classical and non-classical pathways engaged by LTβR. Selective deletion of LTβR in Prox-1-expressing lymphatics 10 days after tamoxifen treatment of Prox-1-Cre-LTbR$^{fl}$ mice also diminished NIK and CCL21 expression (FIG. 4F, and FIG. 4G), confirming the importance of LTβR and NIK signaling.

Figure 9:
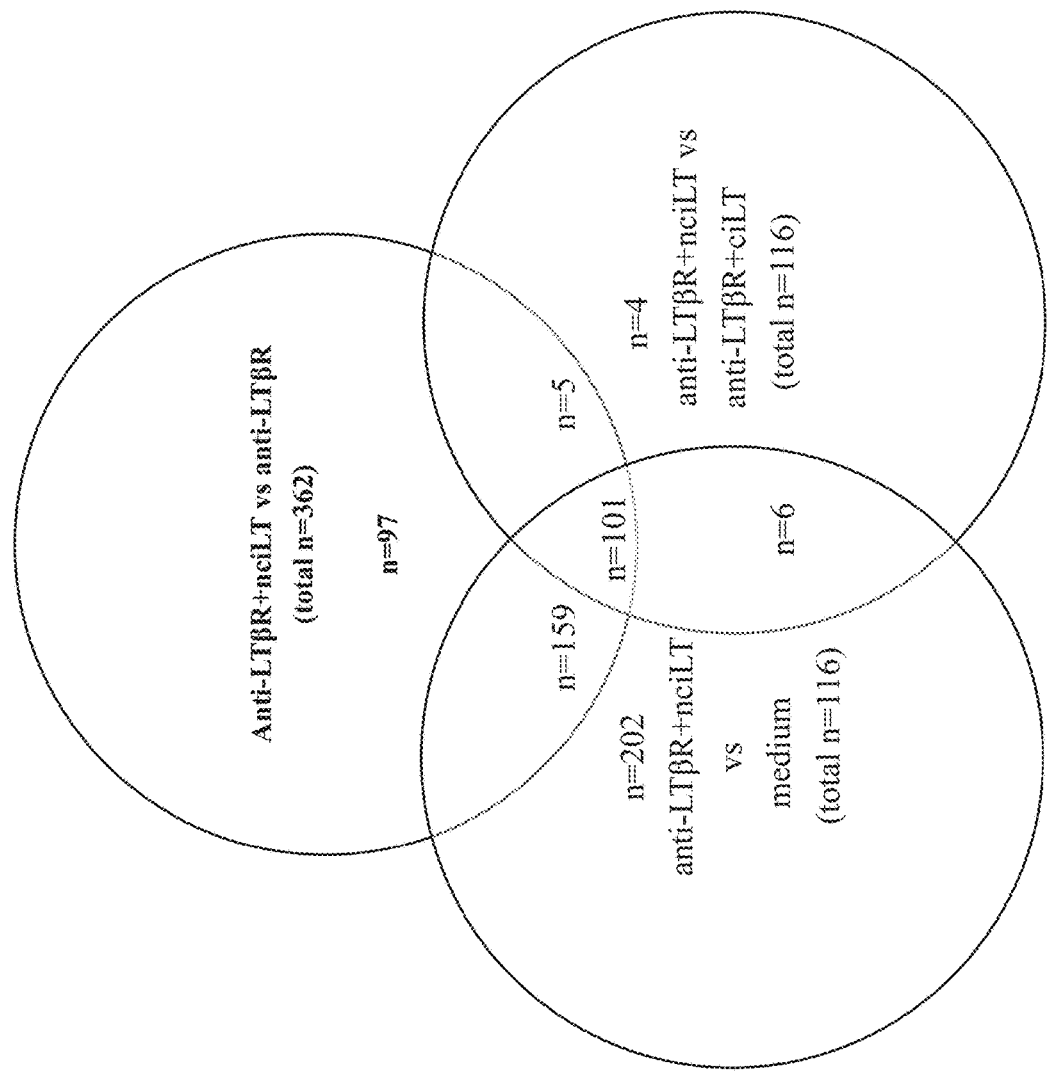
FIG. 9 depicts the results of example experiments, a summary of genes regulated by LTβR signaling along with blockade of signaling pathways with nciLT or ciLT.

To further investigate the role of the separate NFκB signaling pathways, LEC were again stimulated with anti-LTβR plus cross-linking along with blockade of the individual signaling pathways with nciLT or ciLT. After 4 hours, the cells were harvested and transcriptional profiling with Affymetrix gene array and Ingenuity Pathway Analysis (IPA) were conducted. The results showed that LTβR stimulation induced modest global gene activation compared to unstimulated cells. When fold changes in gene expression were corrected for the large number of analyzed genes there were no statistically significant differences between groups treated with medium alone, anti-LTβR mAb alone, or anti-LTβR mAb plus ciLT (data not shown). In contrast nciLT, by blocking the NIK pathway, resulted in more changes in gene expression (data not shown). Anti-LTβR mAb+nciLT vs. medium resulted in significant changes in 468 out of 34,473 transcripts; anti-LTβR mAb+nciLT vs. anti-LTβR resulted in 362 changes; and anti-LTβR mAb+nciLT vs. anti-LTβR mAb+ciLT resulted in 116 changes (FIG. 9). Ingenuity Pathway Analysis showed that the changes in gene expression resulting from nciLT blocking NIK were related to a variety of so-called canonical pathways and upstream regulators, related to endothelial cell adhesion and the response to cytokines and growth factors (FIG. 10, FIG. 11, FIG. 12). Along with the Western and immunoblot data, these results were again consistent with constitutive LTβR activation with little activity in the classical NFκB pathway. Specific activation of the LTβR resulted in increased signaling and downstream responses, without large numbers of changes in early gene expression. The major signaling module was via the non-classical NIK pathway for both constitutive and anti-LTβR mAb driven activation.

Figures 5A, 5B:
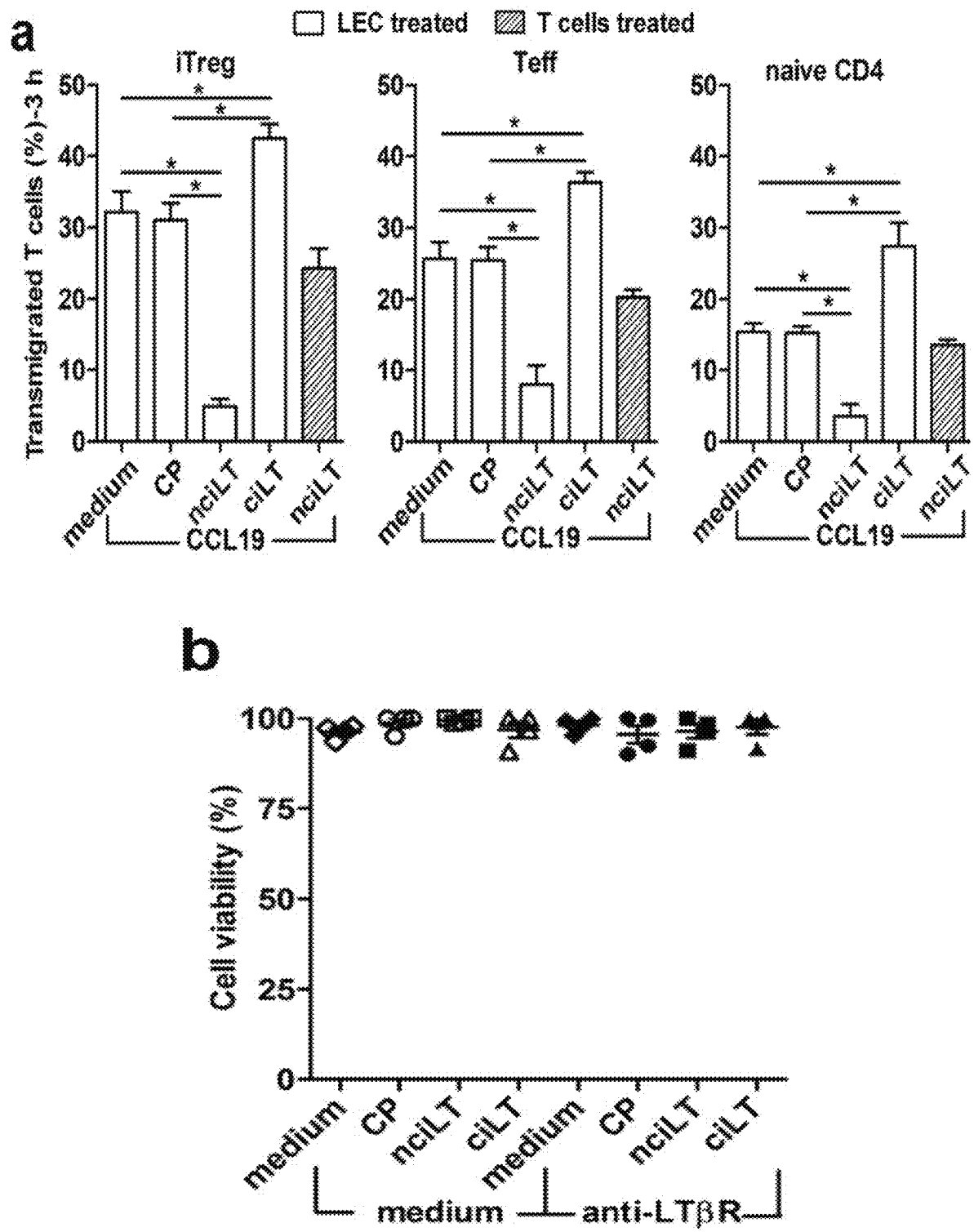
FIG. 5A through FIG. 5G, depicts the results of example experiments demonstrating that LTβR peptides that block non-classical NF-κB signaling pathway inhibit CD4 T cell migration across LEC.
Figures 5C, 5D, 5E:
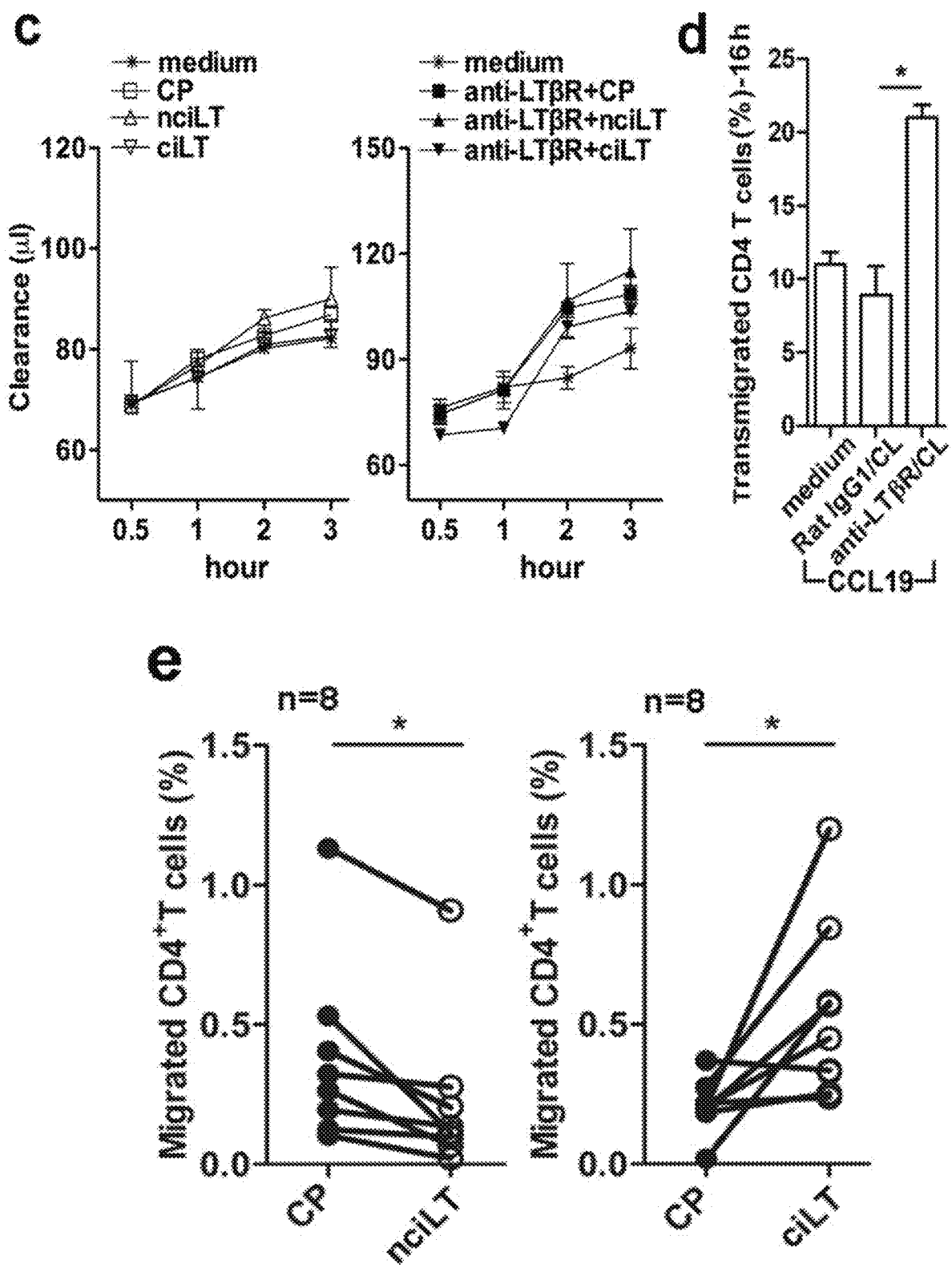

Targeting LTβR-Mediated Non-Classical NFκB Signaling Inhibits T Cell Migration Across LEC It was previously demonstrated that CD4$^+$ Treg but not CD4$^+$ non-Treg utilized cell surface LTαβ to engage LTβR on LEC to migrate across the afferent lymphatic endothelium in vitro and in vivo. Treg expressed higher levels of LTαβ than non-Treg, and modulated membrane and cytoskeletal structure of LECs via LTβR-mediated NIK signaling (Brinkman, C. C. et al., 2016, Nat Commun., 7:12021). To further investigate the roles of the separate signaling pathways, the functional efficacy of the blocking peptides on Treg migration was evaluated. In vitro transmigration assays showed that when LEC but not Treg were pretreated with blocking peptides, that nciLT prevented Treg TEM across LEC (FIG. 5A, left panel; "ciLT1" is synonymous with "ciLT"). In contrast pretreatment of LEC with ciLT, the classical pathway blocking peptide, enhanced Treg migration, likely by modulating the expression of migration molecules regulated by the non-classical pathway, such as increased CCL21 and CXCL12 expression (FIG. 4A, FIG. 4B, FIG. 4C, and FIG. 4D). The peptides did not affect LEC viability or permeability as shown by the MTT viability and Evans Blue barrier assays, respectively (FIG. 5B, FIG. 5C). Thus, migration inhibition was not due to non-specific effects on LEC.

nciLT also inhibited TEM of activated and naïve CD4$^+$ non-Treg T cells across LEC (FIG. 5A, middle and right panels). Our previous worked demonstrated that additional engagement and activation of LTβR was required for TEM of Treg but not other T cells. The biochemical and immunohistochemical analyses in FIG. 1 and FIG. 3 showed that there was partial constitutive LTβR-NIK expression and activation in LEC, with TRAF2 and TRAF3 occupancy along with low levels of p52. The current results showed that other T cells required the constitutive activation of LEC LTβR and LTβR-NIK signaling for TEM. Thus, while not wishing to be bound by any particular theory, nciLT likely inhibited constitutive receptor activity required for all CD4 T cell TEM. When LEC were specifically activated for 12 hours with anti-LTβR mAb plus cross-linking, this resulted in increased migration of naïve CD4 T cells (FIG. 5D), showing that receptor signaling and migration could be enhanced beyond constitutive receptor activation.

Figures 5F, 5G:
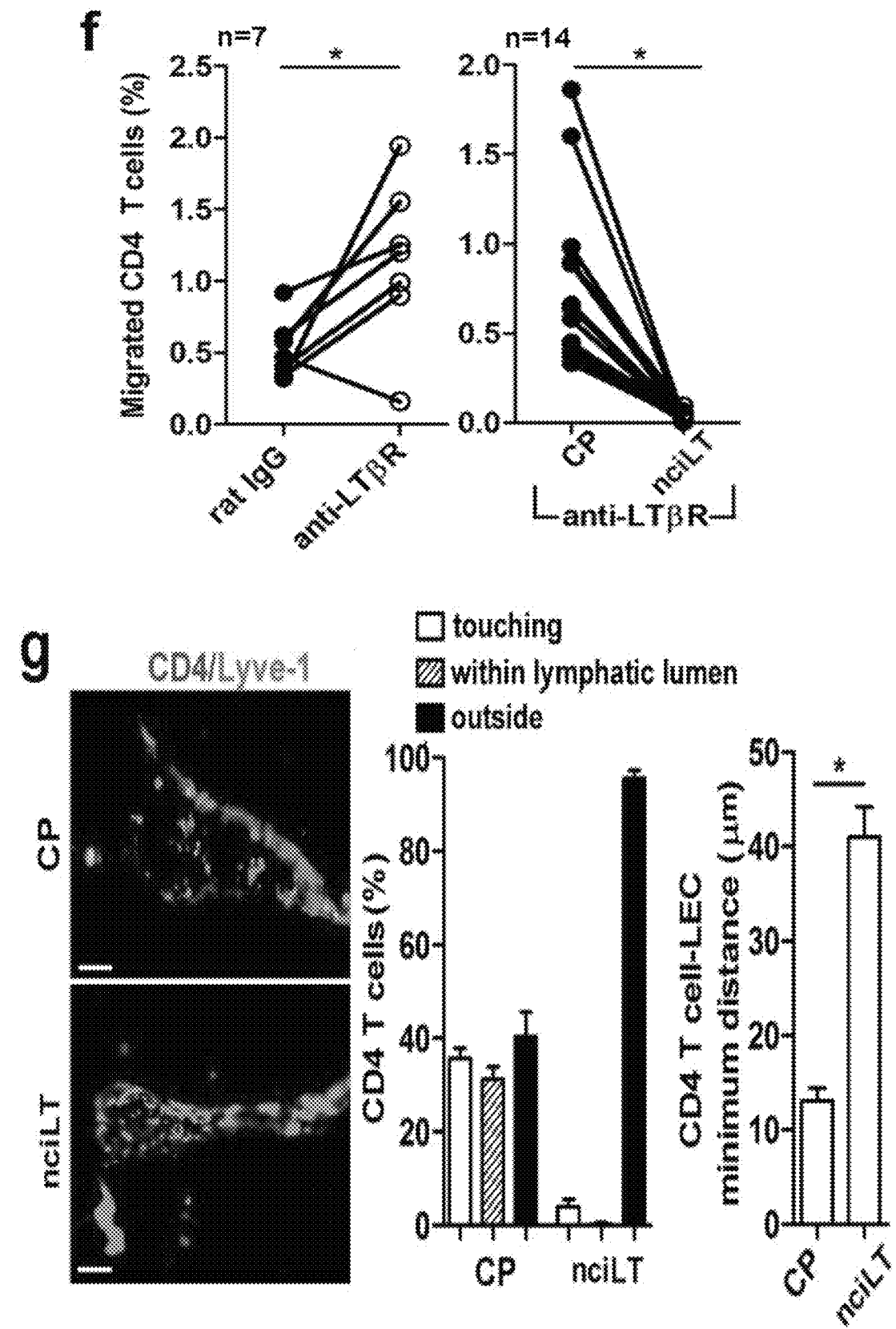

Similar effects on T cell migration were observed in vivo. Injection of nciLT but not ciLT into the footpad inhibited naïve CD4 T cell homing into local draining LNs (FIG. 5E). Injection of anti-LTβR mAb into the footpad enhanced migration, and this enhanced migration was blocked by nciLT (FIG. 5F). Injection of nciLT also inhibited CD4 T cells from entering into the lymphatic vessels in the ear pinna assay (FIG. 5G). These results confirm the role for LTβR signaling and the NIK pathway for afferent lymphatic migration in vivo in both basal and stimulated conditions.
Inhibition of NIK Pathway Enhances T Cell Binding to LEC Through Integrin β4 and VCAM-1

Figures 6A, 6B, 6C:
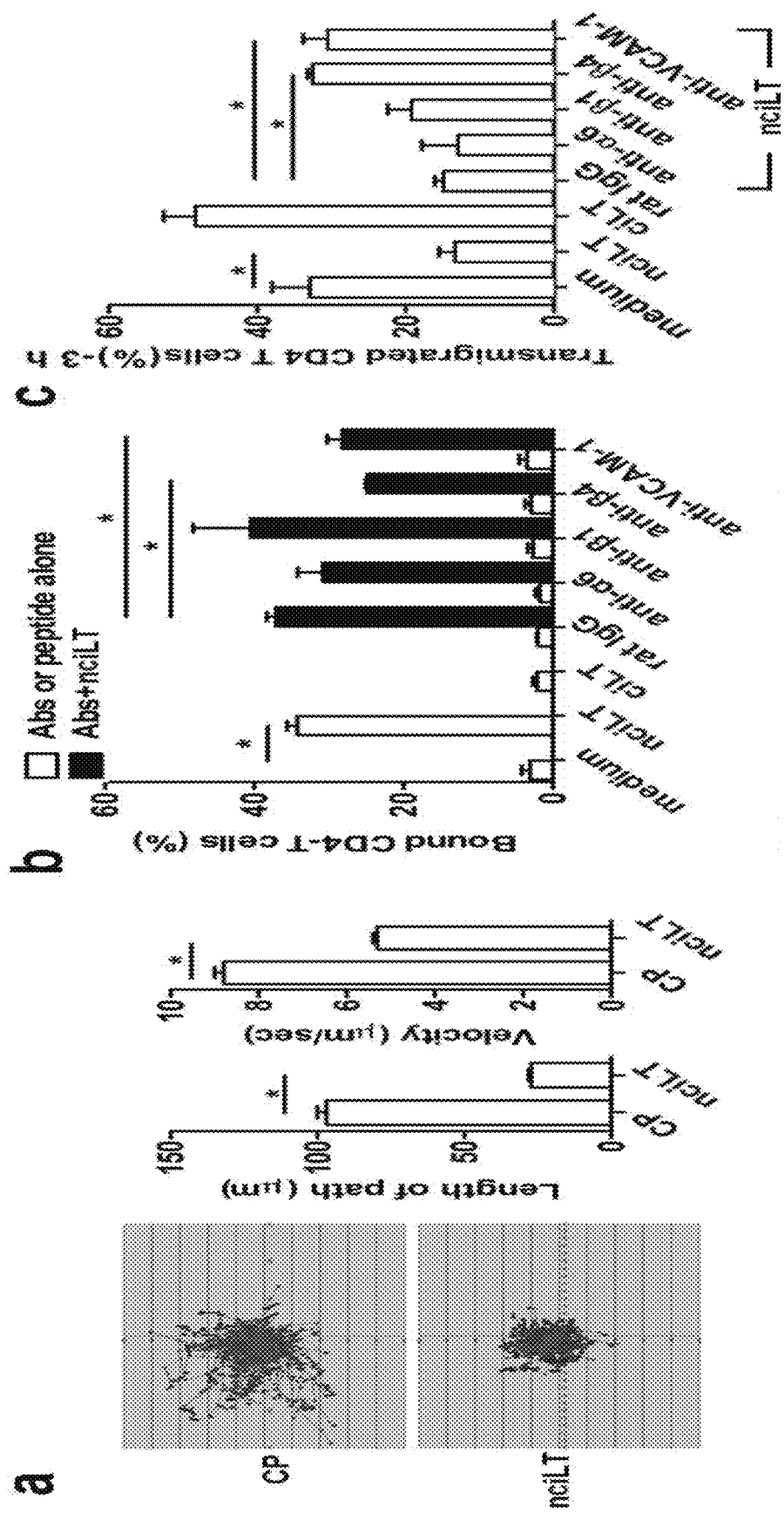

It was also noted that treatment of LEC with nciLT resulted in markedly increased firm attachment of the LEC to the culture surfaces compared to untreated, control peptide treated, or ciLT-treated LEC. This was true both for resting LEC and LEC in which the LTβR was stimulated with the agonist mAb, again showing that LTβR-NIK constitutive and induced signaling were important for LEC layer structure. Given the observation of increased LEC adhesion, and the decreased T cell migration noted above (FIG. 5A, FIG. 5E, FIG. 5F), it was questioned whether there were also alterations in T cell adhesion to LEC. Live 2-D migration imaging showed that the CD4 T cells were tethered on nciLT-treated LEC, with significantly lower motility compared to CD4 T cells on control peptide treated LEC (FIG. 6A). Decreased mobility was accompanied by increased binding of CD4 T cells to nciLT but not ciLT or control peptide treated LEC (FIG. 6B).

Figure 6D:
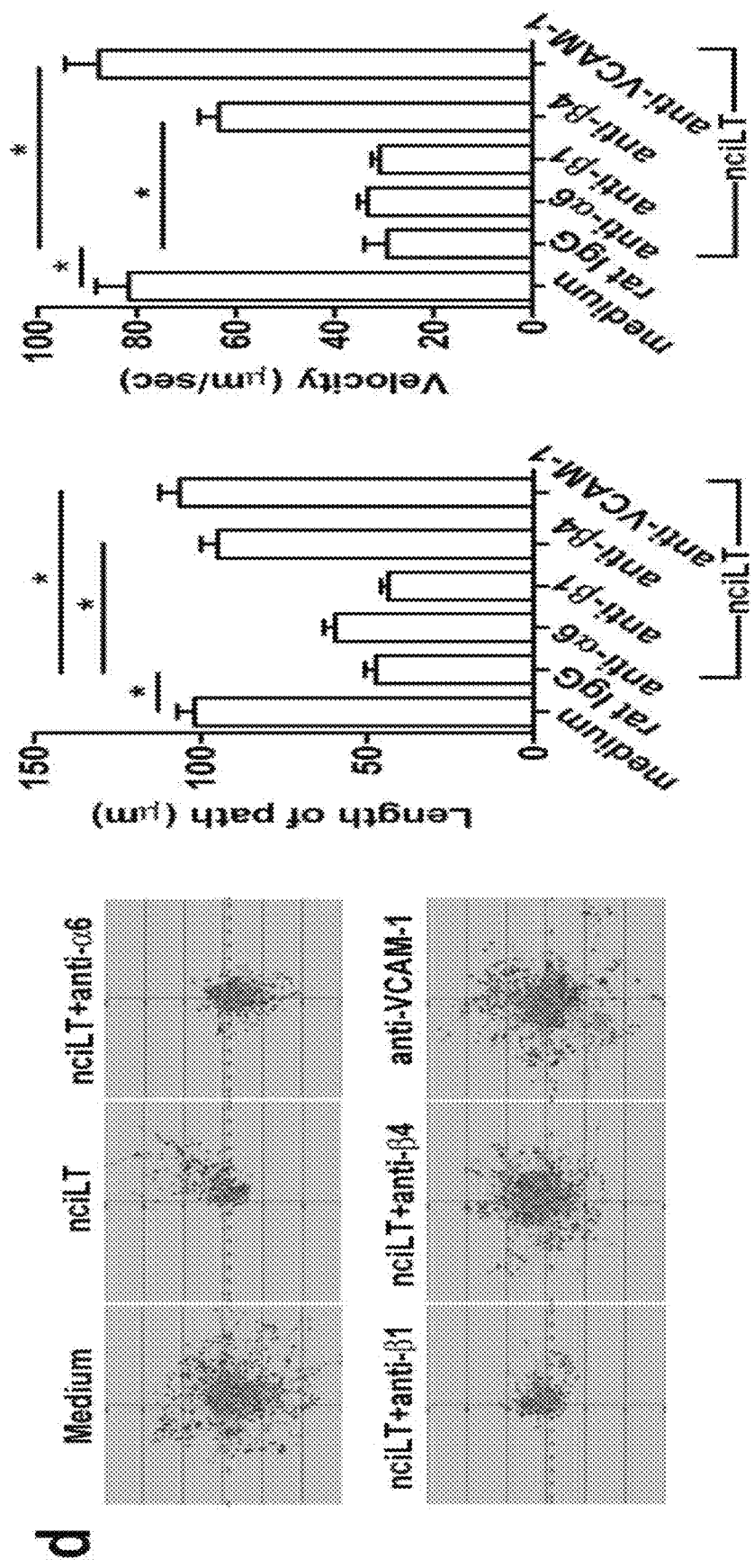
Figures 6E, 6F:
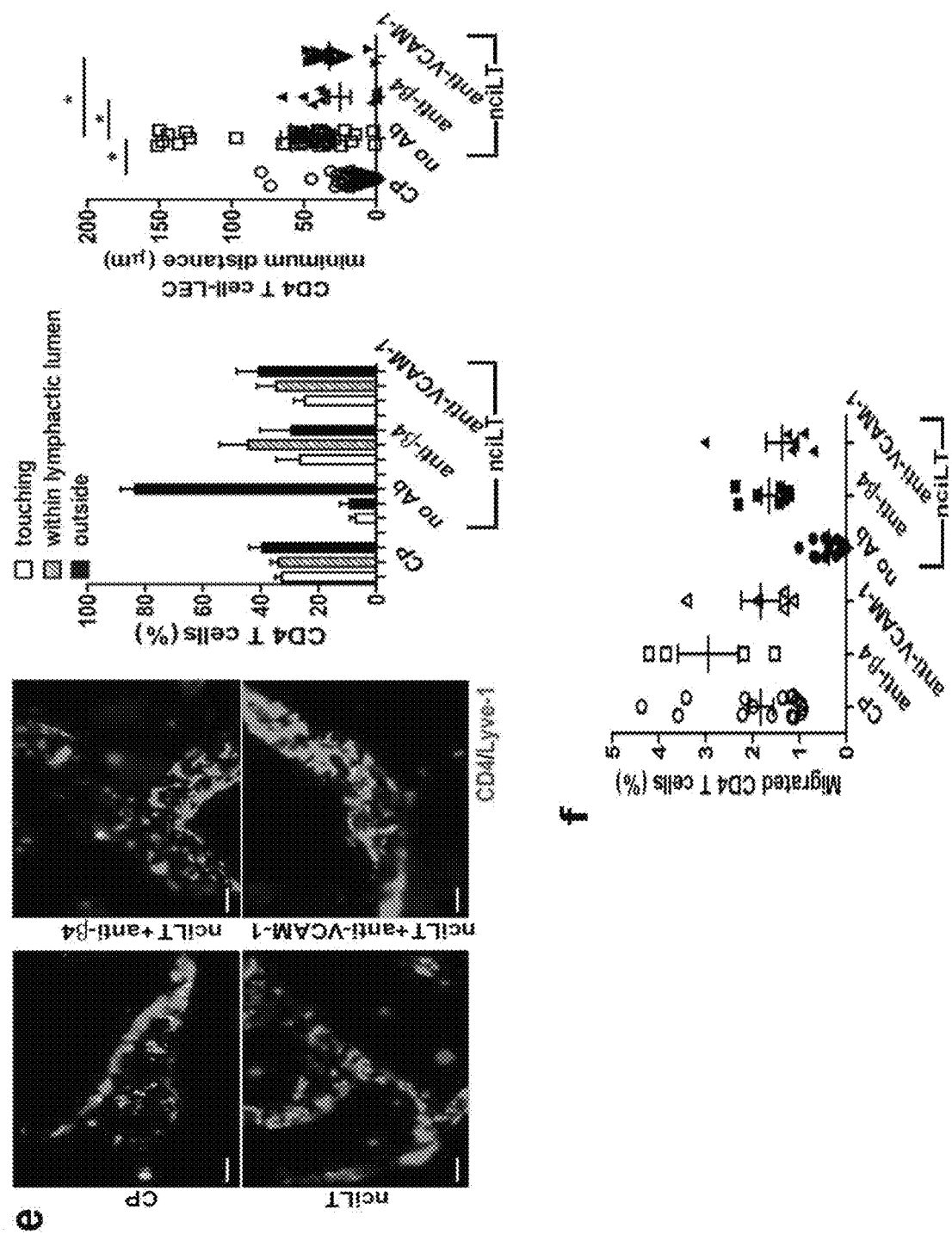
Figure 6G:
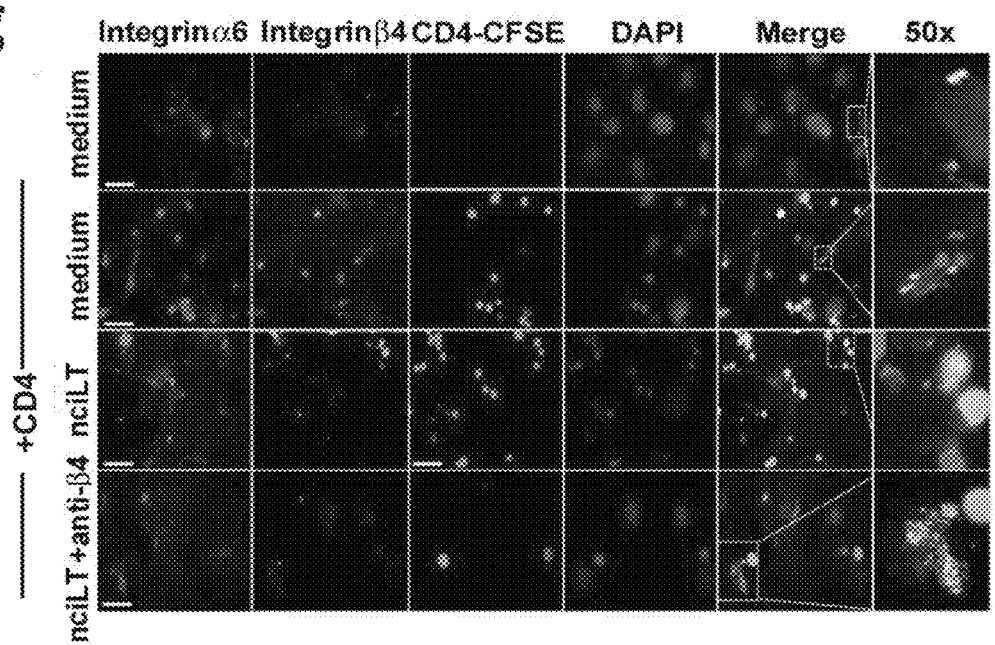
Figure 6H:
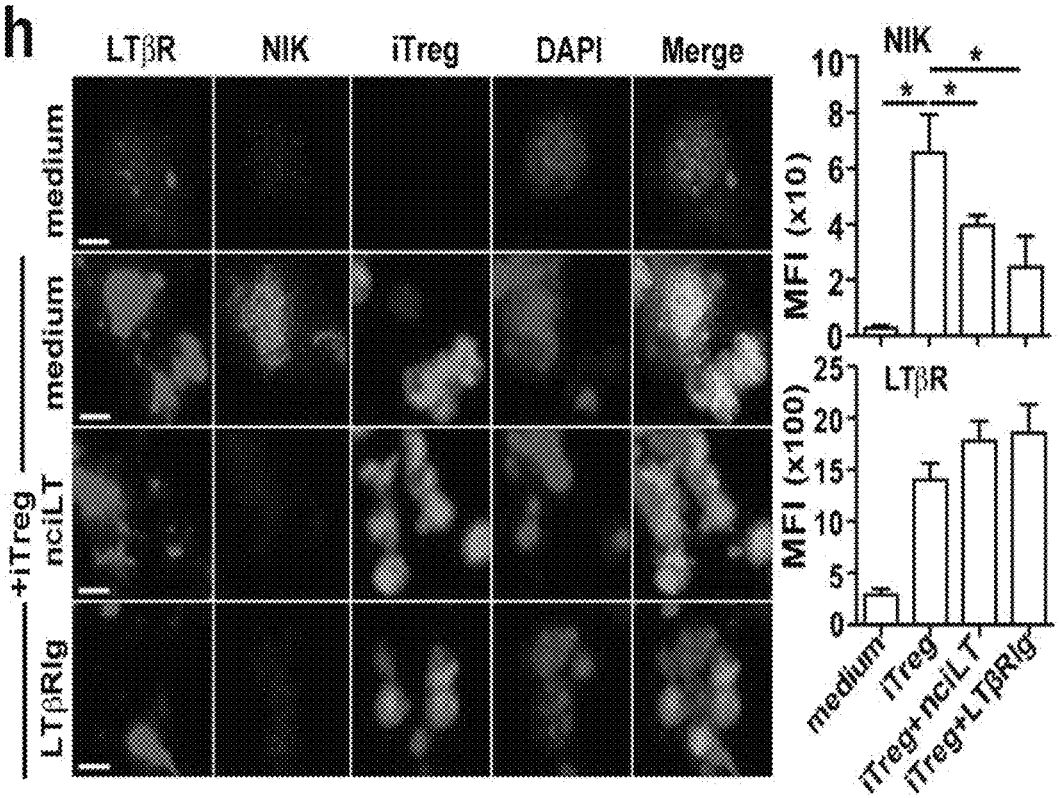
Figures 23A, 23B, 23C:
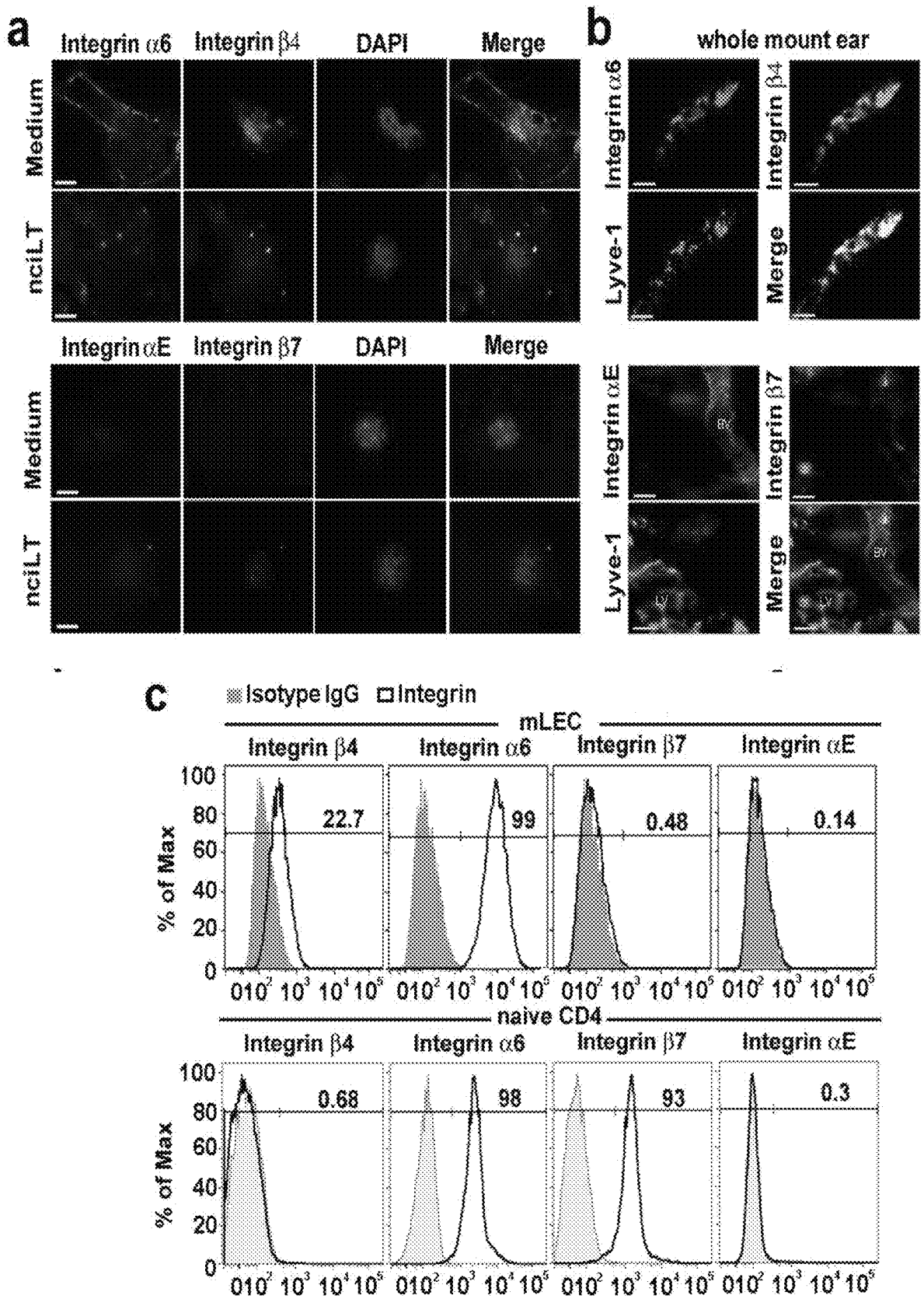
FIG. 23A through FIG. 23F, depicts the results of example experiments demonstrating that LEC and lymphatic vessels express integrins α6 and β4.
Figures 23D, 23E, 23F:
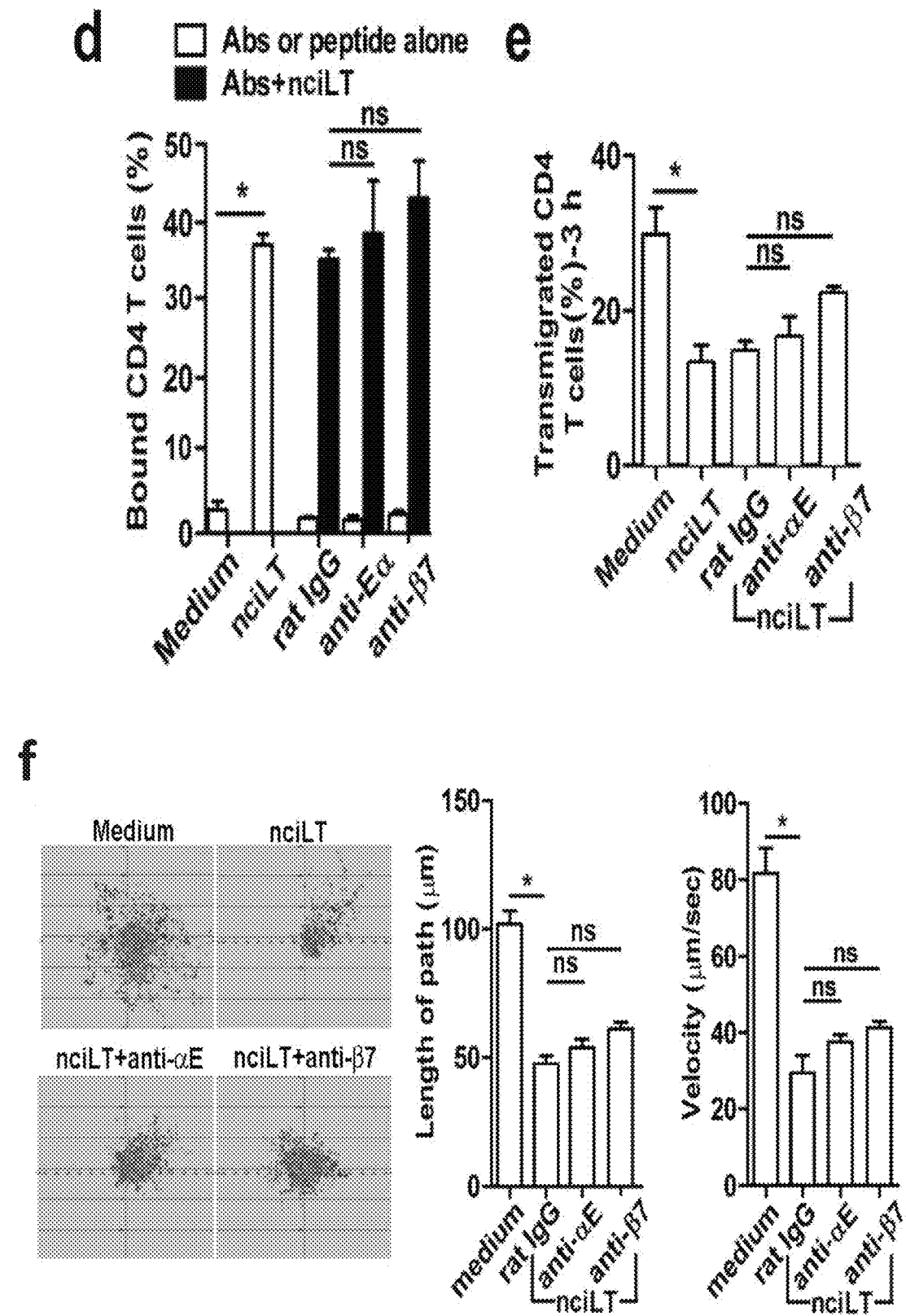

Since T cells bind endothelial cells through a variety of integrins and their receptors, blocking antibodies to several of these specificities (Berlin, C. et al., 1993, Cell, 74:185-195; DeNucci, C. C. et al., 2010, J Immunol, 184:2458-2467) were tested for their activity in the binding, migration, and motility assays. Notably, the enhanced binding of CD4 T cells was diminished when the nciLT treated LEC were pre-incubated with anti-integrin β4 or anti-VCAM-1, but not a variety of other antibodies (FIG. 6B). Concordantly, CD4 T cell migration across the nciLT-treated LECs, and CD4 T cell motility on nciLT-treated LECs, were restored by these antibodies, but not antibodies to a variety of other integrins (FIG. 6C, FIG. 6D, and FIG. 23D). As noted in FIG. 5E through FIG. 5G, nciLT inhibited migration into lymphatic vessels and the draining LN in vivo. Anti-integrin β4 restored these migration events (FIG. 6E, FIG. 6F). The importance of VCAM-1 for leukocyte TEM across lymphatic endothelium has previously been reported (Brinkman, C. C. et al., 2016, Nat Commun, 7:12021; Johnson, L. A. et al., 2006, J Exp Med, 203:2763-2777). Integrin β4 is involved in endothelial cell integrity (Niessen, C. M. et al., 1996, J Cell Sci, 109(Pt 7):1695-1706). Unlike other integrin β chains which can bind multiple α chain partners, the β4 chain only pairs with the α6 chain, while integrin α6 also pairs with β1 (Sonnenberg, A. et al., 1990, J Cell Sci, 96(Pt 2):207-217). The anti-β4 mAb used herein (346-11A) recognizes the ectodomain of integrin β4, and has been suggested to dissociate the α6β4 complex (Sonnenberg, A. et al., 1990, J Cell Sci, 96(Pt 2):207-217). The anti-α6 mAb used herein (GoH3) inhibits integrin binding to laminin, but has not previously been shown to alter functional assays of migration or motility. The ability of anti-β4 and the failure of anti-α6 mAb to alter T-LEC interactions herein is likely due to the precise epitope specificity of the mAbs.

To investigate if nciLT altered integrins and thereby T cell movements, integrin surface expression and distribution was examined. As noted above (FIG. 2A, FIG. 2B, FIG. 2D, FIG. 4A, FIG. 4C, FIG. 4E, FIG. 27A), LTβR signaling and nciLT each caused a significant increase in the expression of VCAM-1 on LEC and SVEC4-10 via stimulation of classical NFκB signaling. Flow cytometric and immunohistochemical analysis of primary LEC in vitro and Lyve-1-expressing lymphatic vessels in vivo demonstrated the co-expression of integrins α6β4 but not other integrins (FIG. 23A, FIG. 23B, FIG. 23C). nciLT did not alter the expression of integrins α6β4, suggesting that NIK inhibition resulted in integrin conformational changes and activation, the stereotyped integrin response to cell signaling to regulate adhesion.

Figure 7:
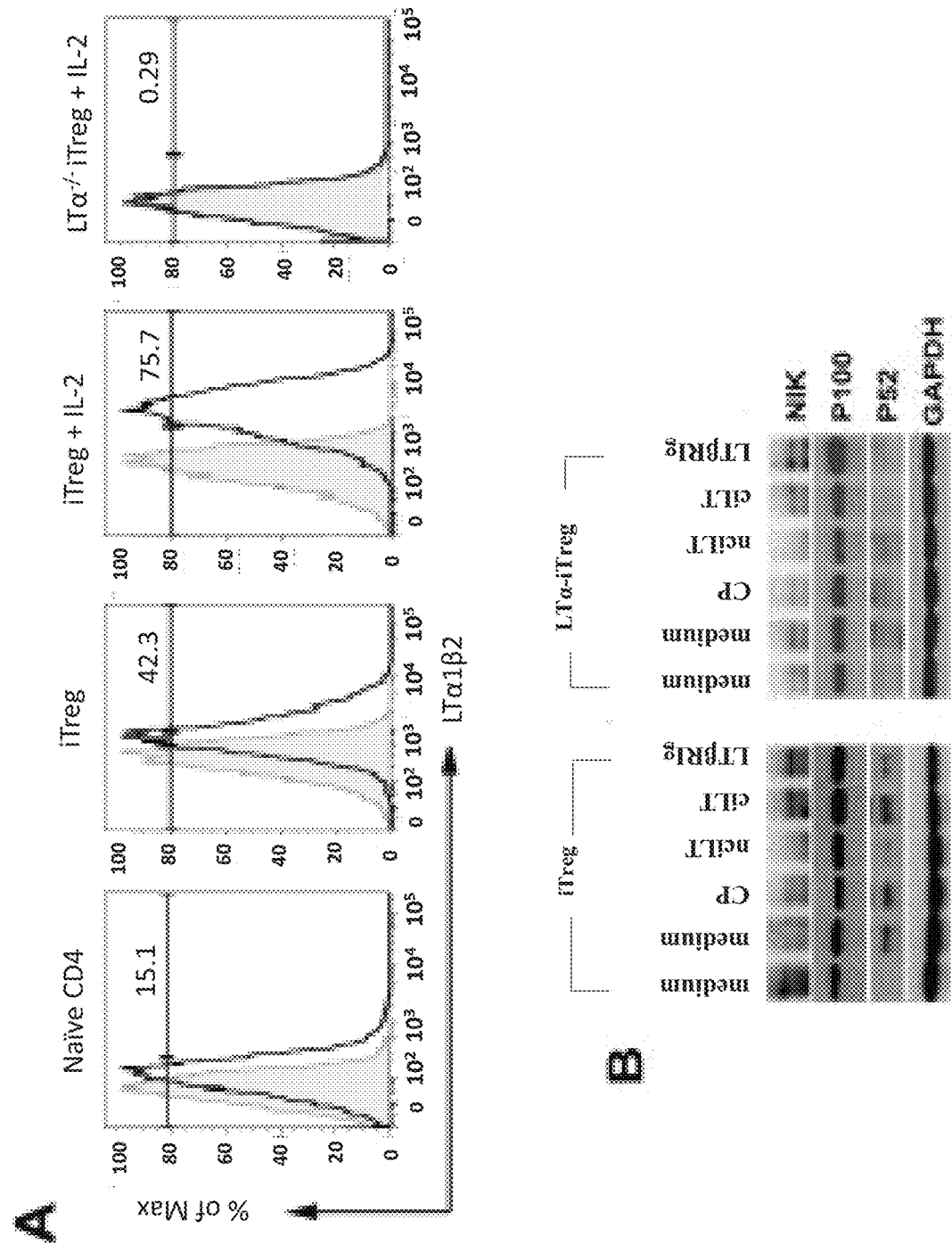
FIG. 7 depicts the results of example experiments demonstrating T lymphocytes engage LTαβ-LTβR NIK pathway and activate cell adhesion molecules and homing chemokines in LEC, as well as the dose-response for nciLT and ciLT.
Figure 24A:
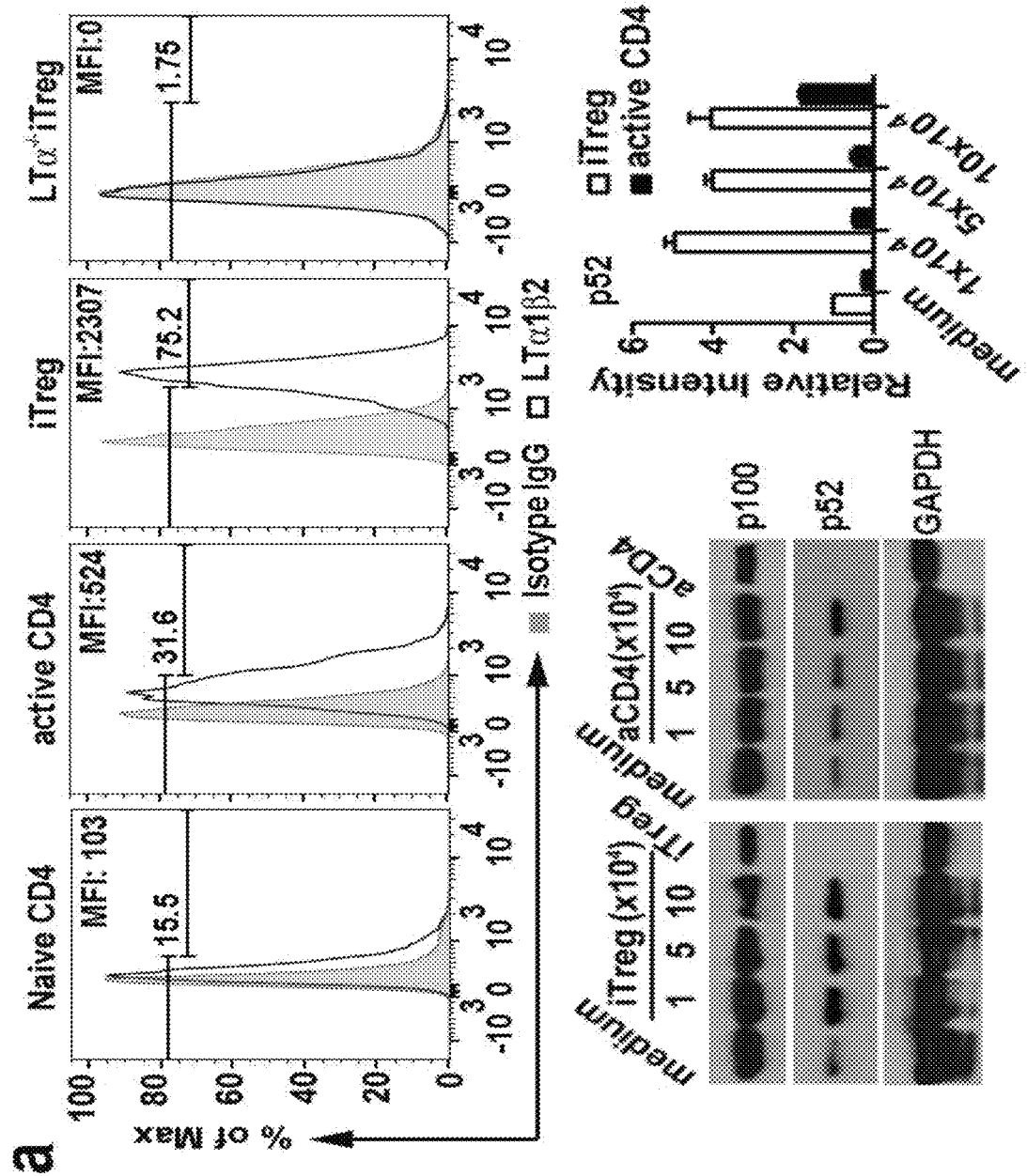
FIG. 24A through FIG. 24B, depicts the results of example experiments demonstrating that T lymphocytes engage LTαβ-LTβR NIK pathway and activate cell adhesion molecules and homing chemokines in LEC.
Figure 24B:
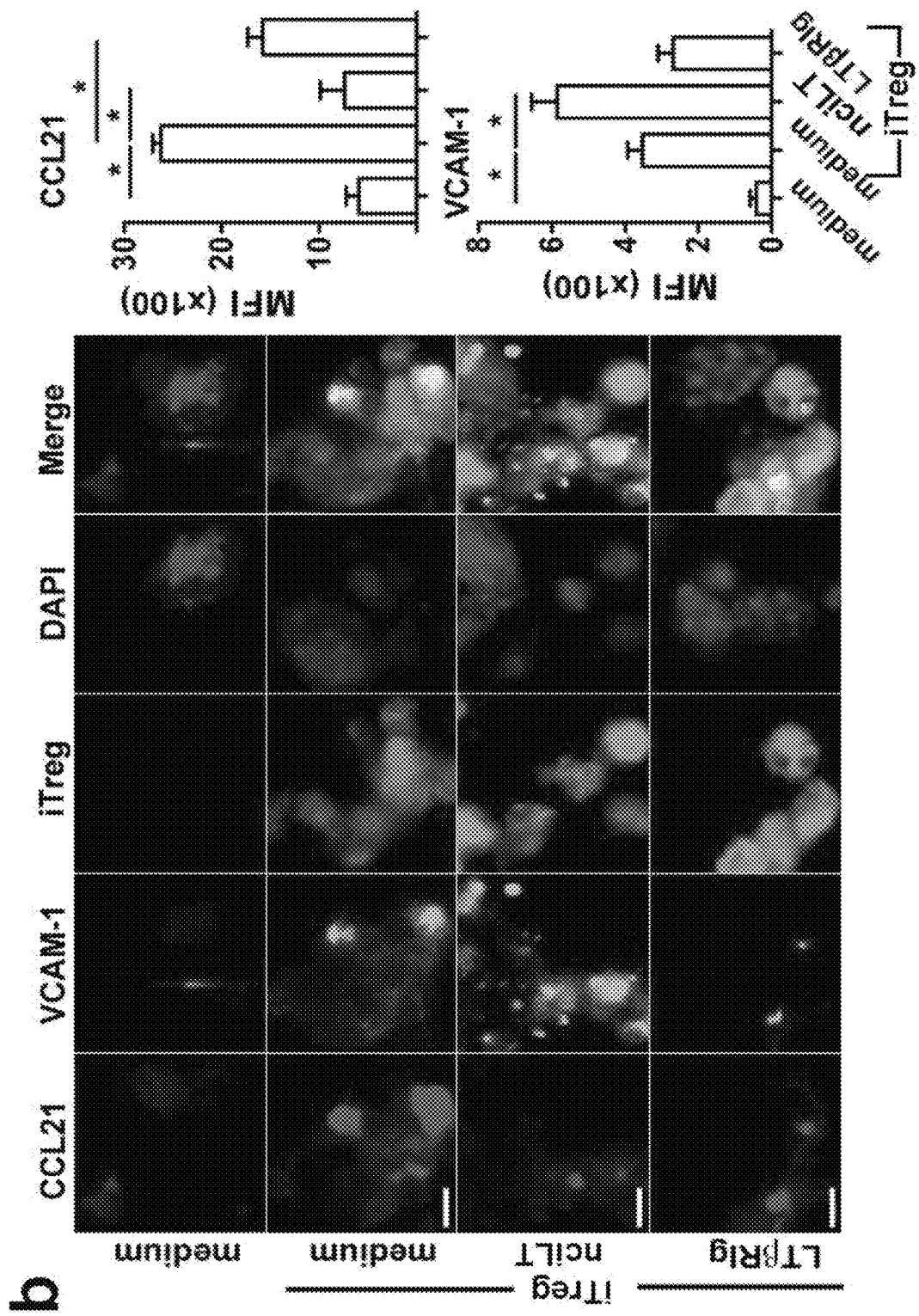

Naïve CD4 T cells were exposed to primary LEC to examine their integrin interactions. These T cells did not express integrin β4, but did express β7 and α6 (FIG. 6I). There was co-localization of the integrin α6 expressing T cells with the β4 expressing LEC under control conditions (FIG. 6J, top row). When the LEC were pretreated with nciLT there was markedly more co-localization of the cells and markers, suggesting clustering of the integrins on both the T cell and LEC cell surfaces (FIG. 6J, middle row). This clustering was inhibited by anti-integrin β4 (FIG. 6J, lower row), commensurate with the binding and motility assays (FIG. 6A through FIG. 6F). Overall, these results demonstrated that NIK regulated LEC integrin β4 and VCAM-1 dependent adhesion, motility, and migration of CD4 T cells.
T Lymphocytes Engage LTαβ-LTβR NIK Pathway To Activate Cell Adhesion Molecules and Homing Chemokines In LEC Recently it was demonstrated that Treg but not non-Treg use LTαβ to engage the LTβR NIK pathway on LEC for afferent TEM to LN (Brinkman, C. C. et al., 2016, Nat Commun., 7:12021). The regulation of the LTβR NIK pathway on LEC and the consequences for T cell migration was further investigated. Flow cytometry showed that Treg specifically expressed higher levels of cell surface LTαβ (FIG. 24A), and expression was markedly increased by IL-2 (FIG. 7A) (Brinkman, C. C. et al., 2016, Nat Commun., 7:12021). IL-2-activated iTreg were incubated with primary LEC, and the activation of the NIK pathway was tested by immunoblot of LEC lysates after the T cells were removed. IL-2 activated iTreg induced p100 processing to p52 in LEC, while LTα-deficient Treg failed to do so (FIG. 7B). Moreover, nciLT but not treated LEC had decreased NIK expression and inhibition of p100 processing to p52.
nciLT and ciLT Nlock LTβR Signaling As mentioned above, Treg cell surface LT binds to and activates the LTβ receptor (LTβR) expressed on lymphatic endothelial cells (LEC), causing changes in LEC morphology that accompany Treg migration. Heretofore it was not known which specific arm of LTβR signaling was responsible for this accompaniment. Herein are presented two novel peptide molecules, nciLT and ciLT, for selectively blocking the two distinct arms of LTβR signaling, which may be useful for modulating T cell migration to prolong allograft survival.

nciLT sequestered TNF receptor-associated factor-3 (TRAF3) but not TRAF2 from the LTβR complex, while ciLT prevented both TRAF3 and TRAF2 binding to the receptor complex in LTβR-activated LEC. nciLT inhibited LTβR/NIK-mediated p100 processing to p52, and suppressed expression of the homeostatic chemokines CXCL12, CCL19, and CCL21 in LEC. In contrast, ciLT inhibited NFκB-mediated IκBα phosphorylation and degradation, and inhibited expression of the inflammatory molecules CCL2 and the VCAM-1. The peptide-mediated effects were highly specific, as TNFR1-mediated NFκB signaling was unaltered by nciLT or ciLT. nciLT prevented CD4 T cell transmigration across the LEC, while suppressing CCL21 and CXCL12 secretion and β-catenin expression, and promoting VCAM-1 expression in LEC. In contrast, ciLT increased CCL21 and CXCL12 secretion, decreased VCAM-1 expression in LEC, and promoted T cell transmigration. LEC expressed high levels of LTβR and had low level constitutive activation of LTβR, as shown by binding of TNF receptor-associated factor-3 (TRAF3) to the LTβR signaling complex. Stimulation of LTβR on LEC resulted in full receptor activation, with TRAF2 and TRAF3 binding to the receptor complex; and preferentially induced non-classical NFκB activation of the NIK pathway, shown by NIK accumulation, p100 processing to p52, and absence of rapid IKKα/β phosphorylation and IκB degradation. LTβR-induced NIK accumulation was further enhanced by inhibiting cIAP, an enzyme that degrades NIK. LTβR stimulation also resulted in the early up-regulation of the inflammatory molecules VCAM-1 and CCL2, mediated by classical NFκB signaling; followed by a later increase in homeostatic lymphocyte homing chemokines CCL19, CCL21, and CXCL12 mediated by non-classical NIK signaling. Specific interruption of NIK pathway by blocking TRAF3, but not TRAF2, binding to LTβR prevented T cell migration across LEC in vitro and in vivo. In contrast, blocking the classical LTβR-TRAF2/3-NFκB pathway promoted T cell transmigration by increasing CCL21 and CXCL12 secretion and decreasing VCAM-1 expression in LEC. Selective targeting of LTβR-mediated non-classical NIK signaling in LEC efficiently prevented T cell migration across LEC, suggesting the essential role of LTβR-TRAF3-NIK-p100/p52 pathway in LEC during T cell migration. nciLT is a potent LTβR-TRAF3-NIK signal blocking agent and migration inhibitor. ciLT specifically targets LTβR-mediated TRAF2-classical NFκB signaling, and promotes Treg transmigration across LEC. LTβR is highly expressed on LEC and is constitutively activated. LTβR preferentially engages non-classical NIK signaling over the classical NFκB pathway. LTβR-TRAF3-NIK signaling regulates homeostatic chemokine production and migration of T cells. Blockade of NIK signaling alters T cell afferent lymphatic migration. These novel pathways regulate lymphatic function and the ability of effector and suppressor T cells to respond to inflammation. The molecular entities presented herein are novel for immune modulation in immunity and tolerance, and these peptides may act as novel therapeutic interventions to promote allograft survival.

Example 2

Treatment of Cancer Cells With the Novel Therapeutic Peptide nciLT Prevented Trans-Endothelial Migration (TEM) in vitro The in vitro TEM assay described above was employed using cancer cells (FIG. 13) to determine whether the therapeutic peptides nciLT and/or ciLT could prevent cancer cell trans-endothelial migration in vitro.

Cancer Cell Migration In Vitro

Figure 13:
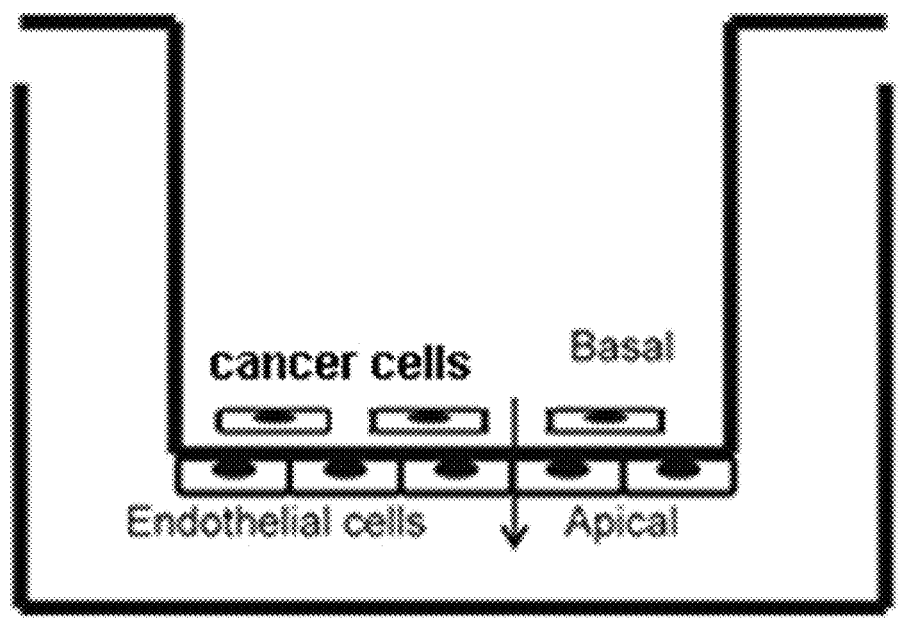
FIG. 13 depicts a diagram for the cancer cell in vitro migration assay.
Figure 16:
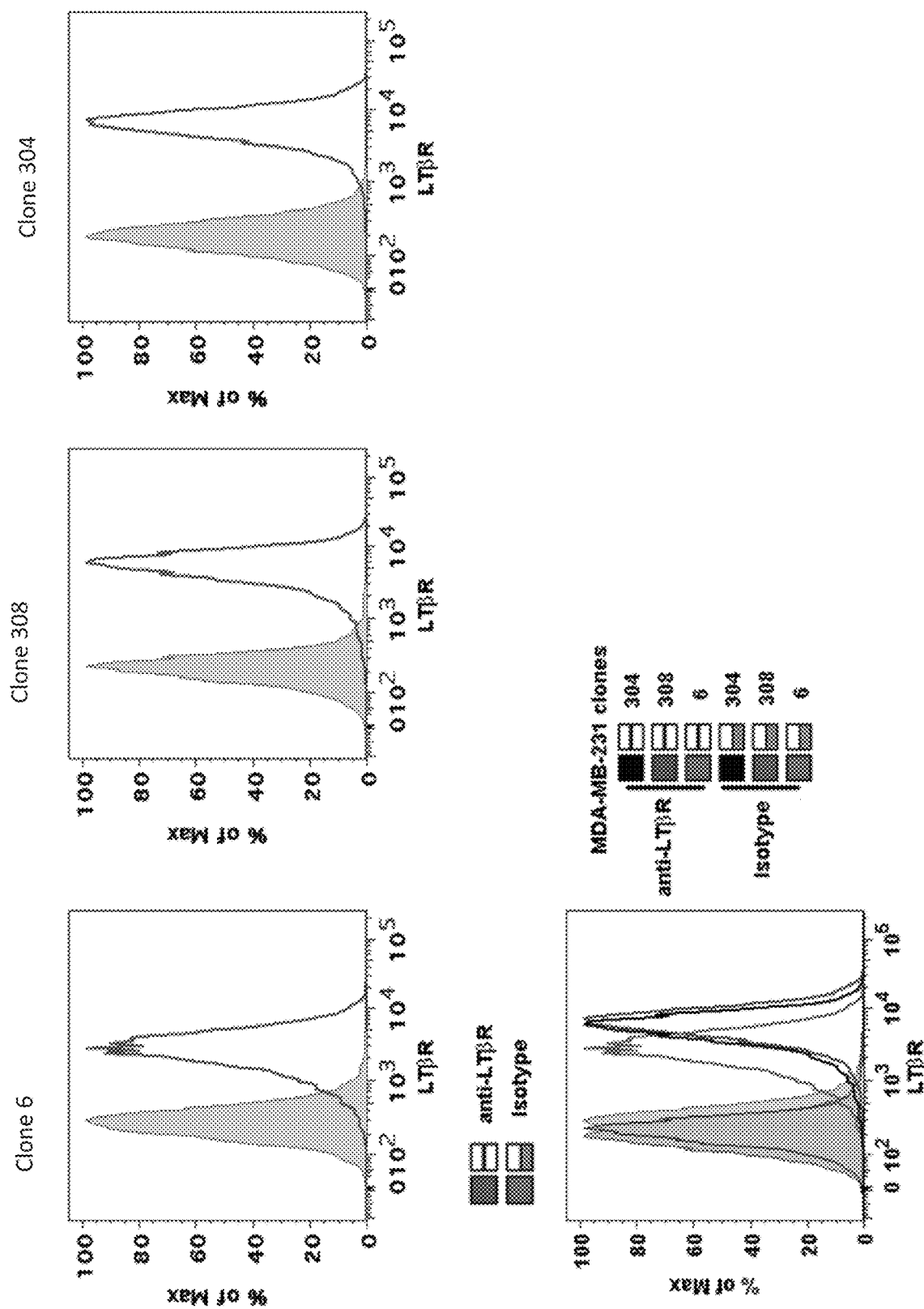
FIG. 16 depicts the results of example experiments demonstrating LTβR expression by human breast cancer MDA-MB-231 clones 6, 308, and 304.
Figure 18:
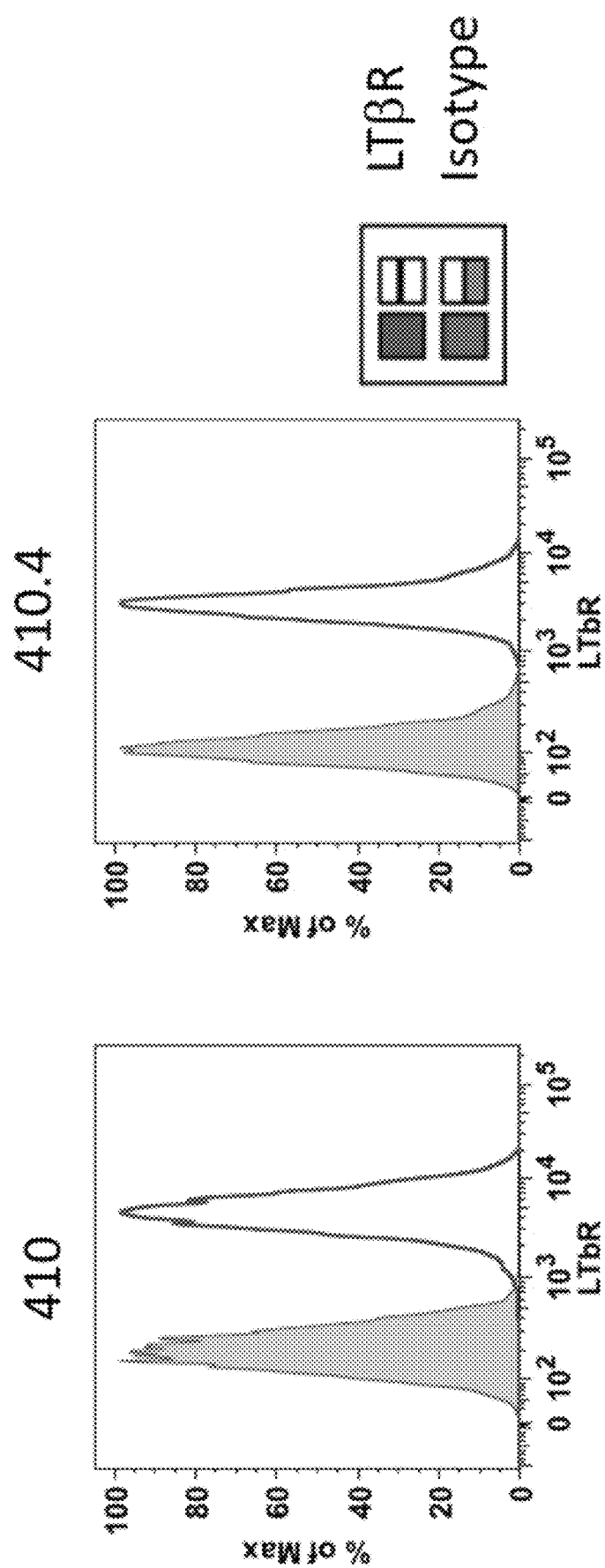
FIG. 18 depicts the results of example experiments demonstrating LTβR expression by mouse breast cancer cell lines 410 and 410.4.
Figure 21:
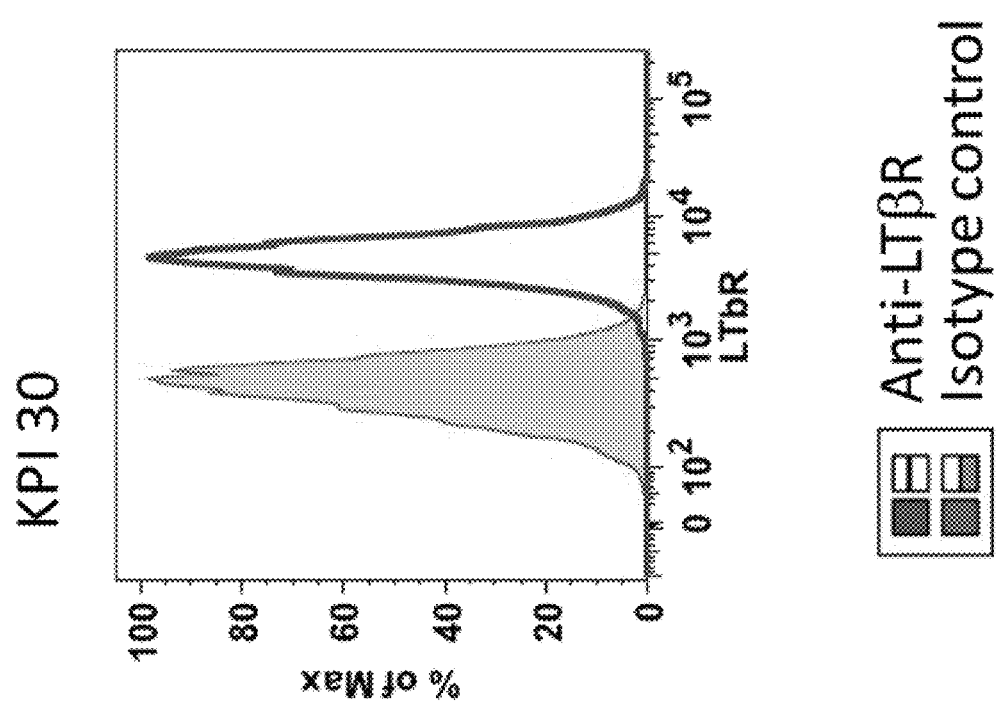
FIG. 21 depicts the results of example experiments demonstrating LTβR expression by mouse sarcoma cell line KPI30.

Human or mouse cancer cell lines were stained with the dye CFSE, then treated with 20 μM control peptide, nciLT peptide, or ciLT peptide for 30 minutes without washing. The cells were allowed to migrate across human iLEC/iSVEC toward SIP or CXCL10 overnight. After the migration step, the cells which migrated into the lower (apical) chamber were counted using flow cytometry (FIG. 13). Abbreviations: Human iLEC-inverted human lymphatic endothelial cells; iSVEC-inverted mouse immortalized LEC line; SIP-sphingosine-1 phosphate.

nciLT Inhibited Cancer Cell Migration Through An Endothelial Cell Layer in vitro To determine whether treatment with nciLT or ciLT could reduce or prevent cancer cell migration through an endothelial cell layer in vitro, three cancer cell lines were chosen and expression of LTβR was confirmed in human breast cancer MDA-MB-231 clones 6 (low metastasis), 308 (metastasis), and 304 (FIG. 16), mouse breast cancer cell lines 410 and 410.4 (FIG. 18), and the mouse sarcoma cell line KPI30 (FIG. 21).

Figure 14:
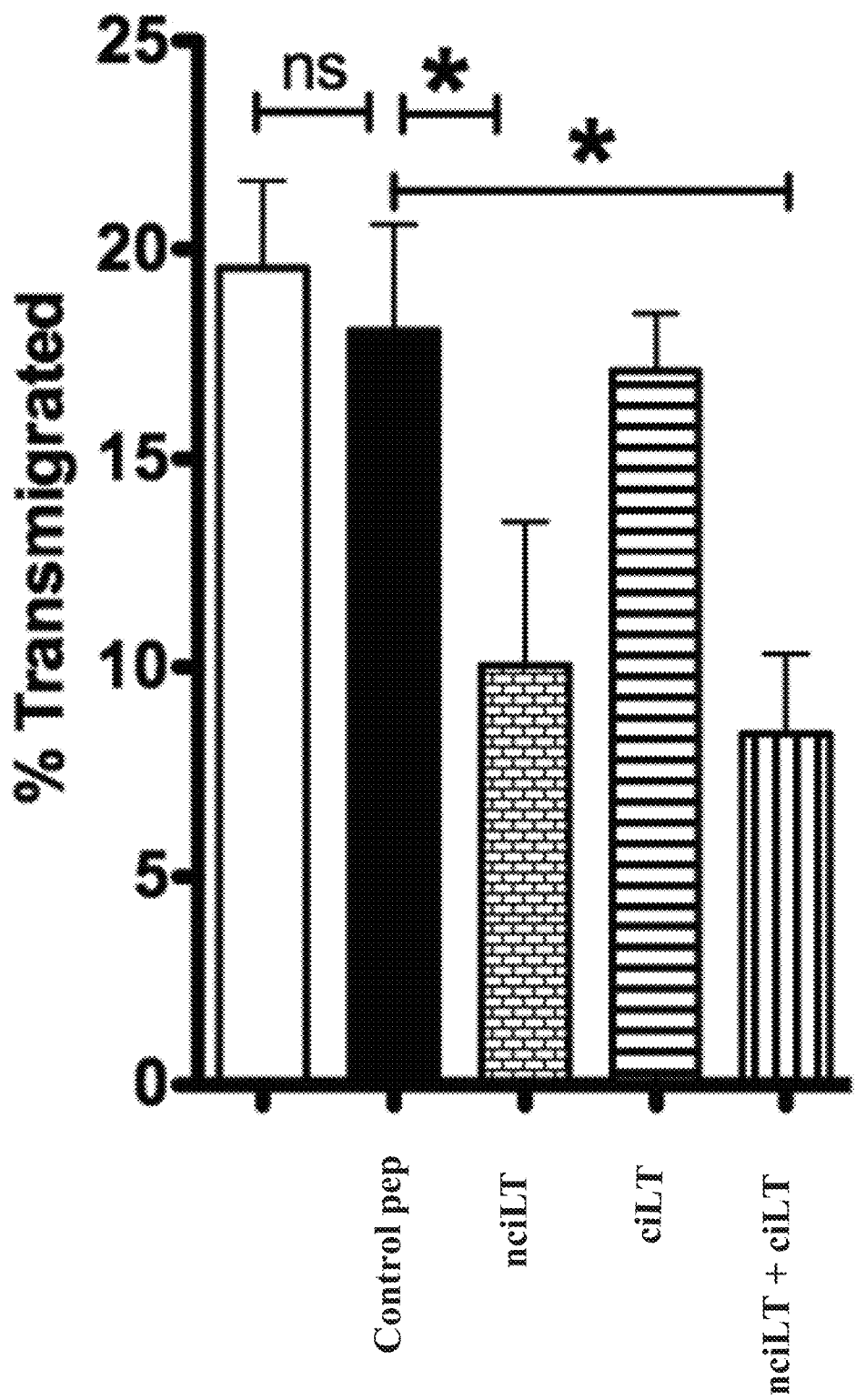
FIG. 14 depicts the results of example experiments demonstrating that nciLT inhibited human breast cancer cell line MDA-MB-231 (parent cell line) migration toward SIP across human iLEC.
Figure 15:
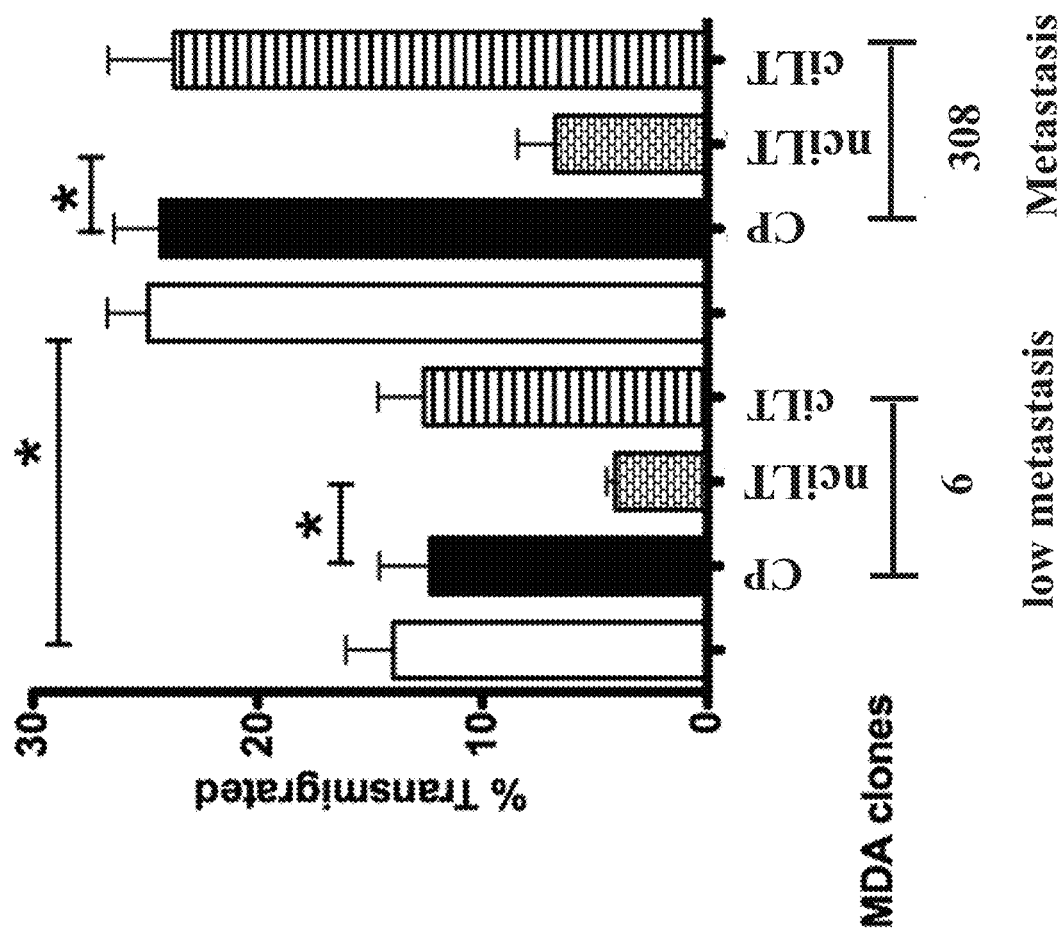
FIG. 15 depicts the results of example experiments demonstrating that nciLT inhibited human breast cancer cell line MDA-MB-231 (clones 6, 308) migration toward SIP across human iLEC.
Figure 17:
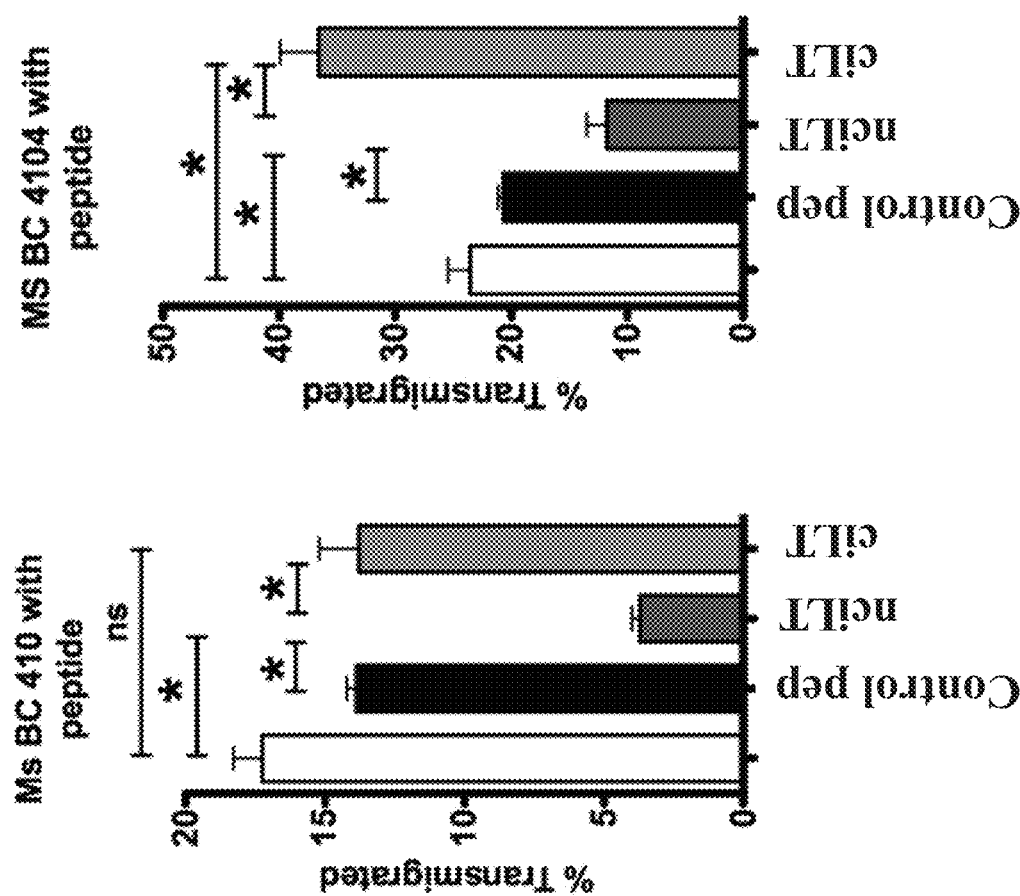
FIG. 17 depicts the results of example experiments demonstrating that nciLT inhibited mouse breast cancer cell lines 410 and 410.4 migration toward SIP across iSVEC.
Figure 19:
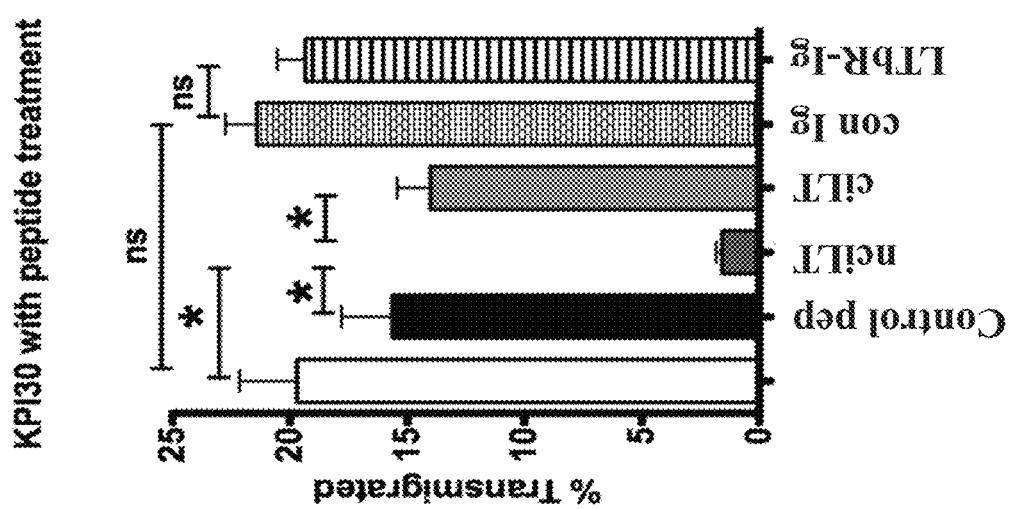
FIG. 19 depicts the results of example experiments demonstrating that nciLT inhibited mouse sarcoma cell line KPI30 migration toward CXCL10 across iSVEC.
Figure 20:
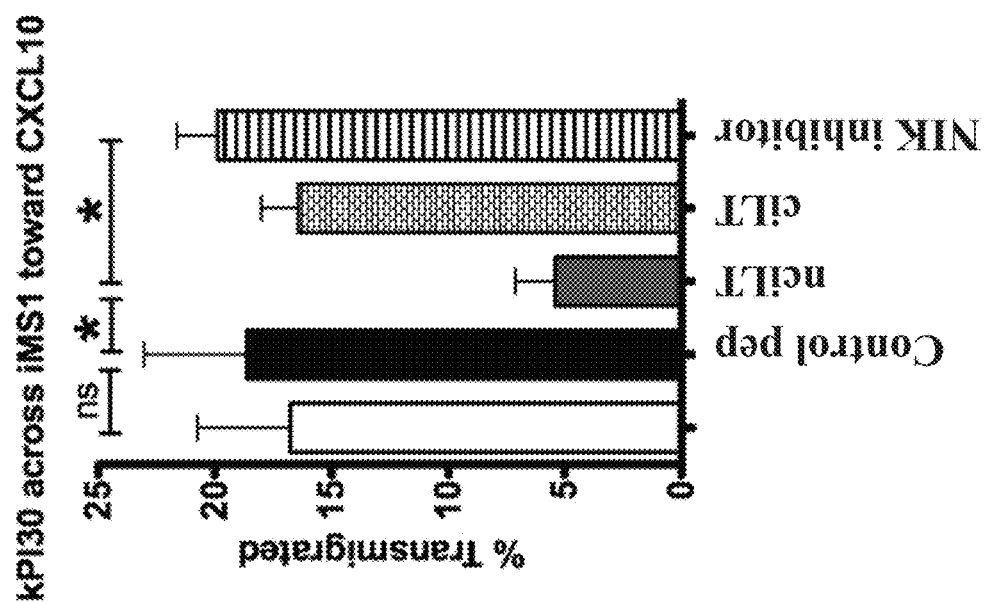
FIG. 20 depicts the results of example experiments demonstrating that nciLT inhibited mouse sarcoma cell line KPI30 migration toward CXCL10 across iMS (blood endothelial cell line).

Treatment of the human breast cancer cell line MDA-MB-231 (parent cell line) with nciLT, but not ciLT, inhibited migration toward SIP across human iLEC (FIG. 14). To confirm this effect, MDA-MB-231 clones were isolated and tested in the TEM in vitro assay. nciLT inhibited human breast cancer cell line MDA-MB-231 (clones 6 and 308) migration toward SIP across human iLEC (FIG. 15). nciLT also inhibited mouse breast cancer cell lines 410 and 410.4 migration toward SIP across iSVEC (FIG. 17). nciLT also inhibited mouse sarcoma cell line KPI30 migration toward CXCL10 across iSVEC (FIG. 19), and inhibited mouse sarcoma cell line KPI30 migration toward CXCL10 across iMS (blood endothelial cell line) (FIG. 20).

nciLT and ciLT for Treatment of Cancer

Tumor invasion of lymphatics is an important step in metastasis (Alitalo, A. et al., 2012, Oncogene, 31:4499-4508). Herein it has been demonstrated by a non-limiting example that treatment of cancer cells with a novel peptide, nciLT, which selectively blocks the NIK-p100 arm of the LTβR signaling pathway, reduces cancer cell migration in the TEM in vitro migration assay. The peptides presented herein, nciLT and ciLT, which selectively inhibit either of the two arms of the LTβR signaling pathway, represent novel approaches for the treatment of various diseases and disorders, including cancer.

Example 3

Targeting LTβR-Signaling Alters Contact Hypersensitivity (CHS) During Sensitization, Elicitation, and Resolution Phases Contact hypersensitivity (CHS) is a T cell-mediated inflammatory response. Hapten sensitization induces migration of dermal DC (dDC) to dLNs for T cell priming (Engeman, T. M. et al., 2000, J Immunol., 164:5207-5214; Fukunaga, A. et al., 2008, J Immunol., 180:3057-3064). Hapten challenge induces another round of dDC migration from skin to dLNs, stimulation of primed T cells, and recruitment of activated T cells to the site of challenge (Piguet, P. F. et al., 1991, The Journal of Experimental Medicine, 173:673-679). During resolution of inflammation, egress of the inflammatory cells out of the CHS site is required (Ortega-Gomez, A. et al., 2013, EMBO Molecular Medicine, 5: 661-674). To test the ability of selective NF-κB-blocking peptides to also regulate DC migration, it was determined that, as for T cells, DC TEM in vitro was inhibited by nciLT and enhanced by ciLT (FIG. 22A). nciLT also inhibited DC migration from skin to dLN in vivo in response to skin painting with FITC (FIG. 22B).

Contact Hypersensitivity and FITC Painting

Figures 22A, 22B, 22C, 22D:
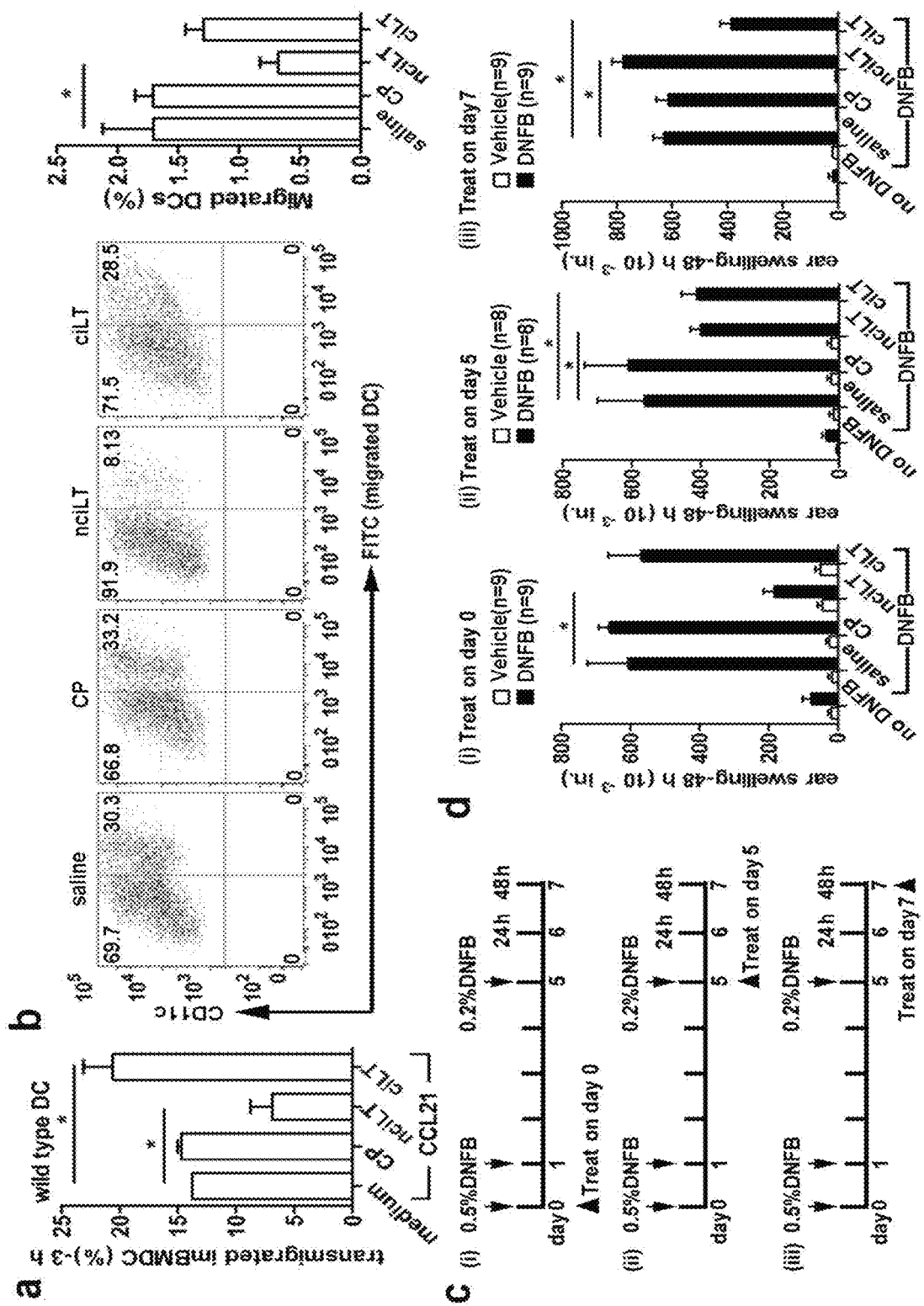
FIG. 22A through FIG. 22E, depicts the results of example experiments demonstrating that inhibition of LTβR signaling alters CHS and leukocyte migration.
Figure 22E:
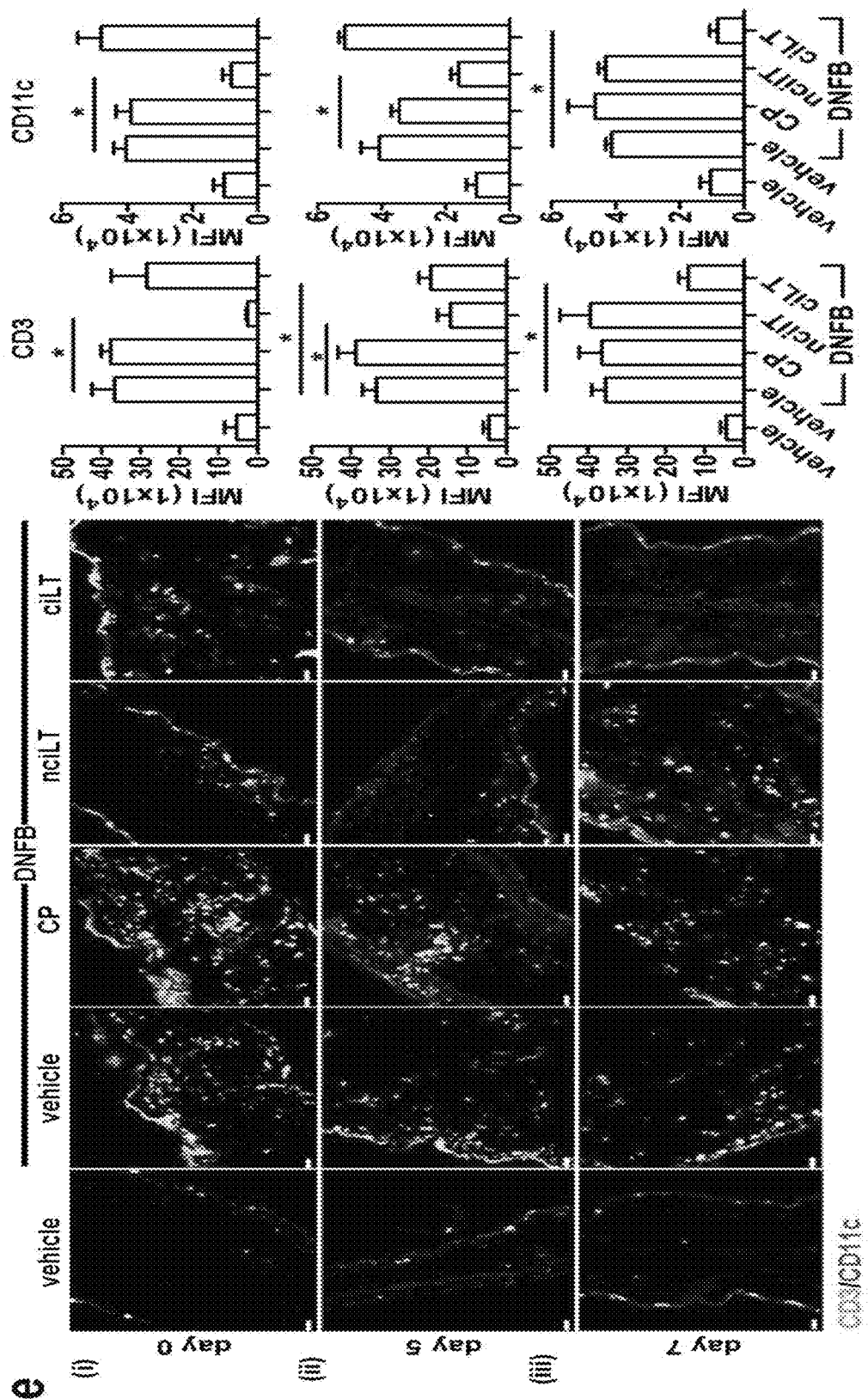

25 μL of 0.5% (v/v) DNFB in acetone/olive oil (4:1) solution was applied onto the shaved abdomen of the mice on days 0 and 1 (sensitization phase). On day 5, the right ear was treated with 20 μL, 0.2% DNFB (10 μL on each side of the pinna), and the same for the left ear with 20 μL acetone/olive oil (challenge phase). Ear swelling was measured with a digimatic thickness gauge (Mitsutoyo, Kanagawa-ken, Japan) before and after 24 to 48 hours DNFB challenge. The contact hypersensitivity (CBS) response (ear swelling) was calculated by subtracting pre-challenge ear thickness for each animal. After euthanasia at the indicated days, the ears were removed and fixed with 10% formaldehyde in PBS and embedded in paraffin for hematoxylin and eosin staining, or were unfixed and embedded in OTC compound (Sakura Finetek, Torrance, Calif.), and processed for immunohistochemistry staining. In vivo DC migration was performed on shaved abdomen as described (Moussion, C. et al., 2011, Nature 479:542-546). Briefly, fluorescein isothiocyanate (FITC, Sigma) 4 mg/mL was dissolved in 1:1 acetone;dibutyl phthalate (Sigma.) and 50 μl applied to the abdominal skin. Recovered inguinal and axillary LNs were digested in 2 mg/mL collagenase D (Roche) for 30 minutes at 37° C. Cells were then passed through a 100 μm cell strainer, and stained for flow cytometry.

nciLT Prevents Contacts Hypersensitivity in vivo At Both the Sensitization and Elicitation Stages By Inhibiting Leukocyte Migration To test the in vivo ability of selective NF-κB-blocking peptides to regulate the stages of the CHS response, the peptides were administered at the time of DNFB sensitization (day 0), challenge (day 5, elicitation phase), or 48 hours after challenge (day 7, resolution phase) (FIG. 22C). Administration of nciLT to the shaved abdomen by i.d. injection 30 minutes before sensitization, inhibited CHS 24 hours after challenge, with fewer T cells and DC infiltrating the ear compared with controls (FIG. 22D(i) and FIG. 22E(i)). Inhibition by nciLT of dDC migration to the dLNs likely reduced T cell priming. Additionally, CCL21 production by LEC has a critical role for DC afferent lymphatic migration (Engeman, T. M. et al., 2000, J Immunol., 164:5207-5214; Russo, E. et al., 2016, Cell Reports, 14:1723-1734), and was suppressed by nciLT (FIG. 4D). Treatment with nciLT or with ciLT in the ear pinna at the time of DNFB challenge and elicitation on day 5 inhibited CHS with reduced T cell infiltration (FIG. 22D(ii) and FIG. 22E(ii) and FIG. 25(ii)). nciLT at this stage may have again interfered with dDC migration to the dLN and stimulation of primed T cells ciLT may have blocked classical-NFκB-driven inflammatory cytokine or chemokine production (e.g., CCL2) by LEC, and CCL2 is upregulated and important during CHS (Vigl, B. et al., 2011, Blood, 118:205-215; Ishimoto, T. et al., 2008, The Journal of the American Society of Gene Therapy, 16: 387-395). ciLT may have also enhanced egress of inflammatory cells out of the ear. By administration of the peptides on day 7, at the start of the resolution stage, nciLT sustained CHS, likely by preventing egress of the inflammatory infiltrate as shown by enhanced T cell and DC infiltration in the ear (FIG. 22E(iii)). In contrast, ciLT enhanced resolution (FIG. 22D(iii) and FIG. 25(iii)), probably by inhibiting cytokines and promoting the egress of the inflammatory cells, as fewer CD3 and CD11c cells were present (FIG. 22E(iii)).

In vivo targeting of T cell and DC migration by the LTβR blocking peptides in CHS showed that these peptides and signaling pathways are relevant for disease; that individual kinetic components of immune responses, such as sensitization, elicitation, and resolution, can be precisely targeted; and that both lymphocytes and myeloid cells are equally influenced by these pathways. These findings open up the possibility for other applications and investigations of how lymphatic signaling and trafficking regulate immunity. These peptides may act as novel therapeutic interventions to regulate immune responses, and serve as a foundation for compound screening and drug discovery.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for inhibiting cell motility of a cell selected from the group consisting of a T regulatory cell, a dendritic cell and a cancer cell, comprising an inhibitor of the non-classical LTβR-NFκB signaling pathway, wherein the inhibitor comprises a polypeptide comprising the amino acid sequence of SEQ ID NO:4.

2. A method for inhibiting cell motility of a cell selected from the group consisting of a T regulatory cell, a dendritic cell and a cancer cell, comprising administering to a subject an effective amount of the composition of claim 1.

3. The method of claim 2, wherein the subject has, or is at risk of developing, at least one condition selected from the group consisting of tissue graft rejection, inflammation, contact hypersensitivity, and cancer.

* * * * *